(12) United States Patent
Takahashi

(10) Patent No.: US 7,241,349 B2
(45) Date of Patent: Jul. 10, 2007

(54) NONDESTRUCTIVE EVALUATING METHOD FOR AGED DETERIORATION IN AUSTENITIC STAINLESS STEEL

(75) Inventor: Seiki Takahashi, Morioka (JP)

(73) Assignee: Iwate University, Iwate Pref. (JP)

( * ) Notice: Subject to any disclaimer, the term of this patent is extended or adjusted under 35 U.S.C. 154(b) by 555 days.

(21) Appl. No.: 10/732,130

(22) Filed: Dec. 10, 2003

(65) Prior Publication Data

US 2004/0140020 A1    Jul. 22, 2004

(30) Foreign Application Priority Data

Dec. 19, 2002  (JP)  ............... 2002-368187
Jun. 20, 2003  (JP)  ............... 2003-176884

(51) Int. Cl.
*G01D 7/02*   (2006.01)
*G01R 33/00*  (2006.01)

(52) U.S. Cl. ......................... 148/509; 73/789
(58) Field of Classification Search ............... 148/508, 148/509; 73/789
See application file for complete search history.

(56) References Cited

U.S. PATENT DOCUMENTS

| | | | | |
|---|---|---|---|---|
| 5,059,903 A | * | 10/1991 | Otaka et al. | ............... 324/223 |
| 5,142,227 A | | 8/1992 | Fish | |
| 6,633,159 B1 | * | 10/2003 | Robar et al. | ............... 324/240 |
| 6,868,735 B2 | * | 3/2005 | Takahashi | ............... 73/789 |

FOREIGN PATENT DOCUMENTS

EP   1 098 194 A2   5/2001
WO   WO 99/24803    5/1999

OTHER PUBLICATIONS

S. Chifan, et al., Evaluation of Fatigue State of Ferromagnetic Steels by Magnetic Methods, 15 WCNDT, 'Online! 2000, pp. 1-4, Dec. 2000.
S. Takahashi, et al., Magnetization curves of plastically deformed Fe metals and alloys, Journal of Applied Physics vol. 87, No. 2, Jan. 15, 2000, pp. 805-813.

* cited by examiner

*Primary Examiner*—Scott Kastler
(74) *Attorney, Agent, or Firm*—Knobbe Martens Olson & Bear, LLP

(57)   ABSTRACT

A nondestructive evaluating method for aged deterioration in austenitic stainless steel comprises an information obtaining step for previously obtaining a relationship between an applied stress σ and the first ratio $Ms/\chi_H{}^*$ between a saturation magnetization Ms and a pseudo susceptibility $\chi_H{}^*$ based on reference minor hysteresis loops obtained by applying stresses σ, respectively, correspondingly to a result of a tensile test for the same kind of material as an evaluation target. In a measuring step, values of the first ratio $Ms/\chi_H{}^*$ are obtained as measured values from measured minor hysteresis loops obtained by measuring the evaluation target. In an evaluating step, the relationship between the applied stress σ and the first ratio $Ms/\chi_H{}^*$ is compared with the measured values, thereby evaluating aged deterioration of the evaluation target. The minor loops are obtained by stepwise changing a magnetic field amplitude $H_a$ within a range of a magnetic field intensity lower than a saturation magnetization.

6 Claims, 41 Drawing Sheets

NONDESTRUCTIVE EVALUATING METHOD FOR AGED DETERIORATION IN AUSTENITIC STAINLESS STEEL

BACKGROUND OF THE INVENTION

1. Field of the Invention

The present invention relates to a method for nondestructively evaluating and quantitatively finding deterioration of material strength due to aging of an austenitic stainless steel structural material or an austenitic stainless steel structure comprised of such structural materials.

2. Description of the Related Art

Since more than half a century ago, it has been known that austenitic stainless steel transforms from paramagnetic to ferromagnetic, due to plastic deformation. Further, nondestructive evaluating methods utilizing this phenomenon have been attempted in U.S.A., German, Japan and other countries. Thus, as methods for nondestructively evaluating "deterioration of material strength due to aged metal fatigue of an austenitic stainless steel structural material or an austenitic stainless steel structure comprised of such structural materials" (hereinafter called "aged deterioration of strength"), there have been resultingly and conventionally-known those methods which adopt a measuring device for measuring saturation magnetization of martensitic phase transformed from an austenitic stainless steel due to plastic deformation thereof, so as to evaluate aged deterioration in the austenitic stainless steel. Moreover, there has been known a method for evaluating fatigue of an evaluation-target material (i.e., aged deterioration of strength) based on a change of magnetic permeability of the material, because the magnetic permeability of the material changes with transformation from austenite phase to martensitic phase due to plastic deformation (see JP-A-8-248004, for example).

However, it has been impossible to uniquely obtain information of an internal factor (internal stress), by the conventional method for evaluating an aged deterioration in austenitic stainless steel based on magnetic characteristics such as saturation magnetization and magnetic permeability.

Namely, in the above-mentioned conventional nondestructive evaluating method for evaluating aged deterioration in an evaluation target, there are obtained reference data by performing magnetization measurement by changing the amount of external factors (external stress, temperature) which cause the martensitic transformation (for example, by changing the number of times of repeated load in the above-mentioned JP-A-8-248004) so as to change the amount of the martensitic phase deriving from austenite phase while utilizing a fact that the martensitic transformation is caused by a machining operation of the evaluation target, to thereby nondestructively evaluate the aged deterioration in the evaluation target based on the reference data.

The martensitic transformation is caused by various factors, and the martensitic transformation is caused by not only external factors (external stress, temperature) but also internal factors (internal stress, chemical composition).

However, those magnetic characteristics, such as saturation magnetization and magnetic permeability which have been conventionally used as parameters for evaluating aged deterioration, are changed in response to the amount of the martensitic phase which is changed by the amounts of external factors, and thus the magnetic characteristics are not necessarily brought into a one-to-one relationship with the internal factor (internal stress) which is a cause of the aged deterioration of strength. Thus, it has been impossible to precisely obtain information of lattice defects such as dislocations within a material by the above-mentioned conventional nondestructive evaluating method for aged deterioration in austenitic stainless steel based on magnetic characteristics such as saturation magnetization and magnetic permeability.

SUMMARY OF THE INVENTION

It is therefore an object of the present invention to propose an evaluating method for quantitatively and nondestructively evaluating lattice defects such as dislocations which cause aged deterioration in austenitic stainless steel, thereby making it possible to perform a nondestructive inspection during a period of time from the beginning of usage of austenitic stainless steel up to the initiation of cracks due to aged deterioration, and to detailedly specify the crack initiation time and the location of the crack initiation.

To achieve the object, the present invention provides a nondestructive evaluating method for quantitatively and nondestructively evaluating aged deterioration in austenitic stainless steel, comprising an information obtaining step, a measuring step, and an evaluating step.

The information obtaining step is to previously conduct a tensile test for the same kind of austenitic stainless steel as an evaluation target austenitic stainless steel, so as to obtain a relationship between stress and strain, and to apply a stress σ having a value changed correspondingly to the relationship between stress and strain to the same kind of austenitic stainless steel to thereby obtain reference minor hysteresis loops, thereby obtaining correlations (for example, the first relationship of the relationship between a pseudo coercive force Hc* which is a value of a magnetic field intensity H where the value of magnetic flux density B is zero and a magnetic field amplitude $H_a$ to be applied to the material; and the second relationship of the relationship between, the first ratio Ms/$\chi_H$* between a saturation magnetization Ms and a pseudo susceptibility $\chi_H$* which is a gradient of the reference minor hysteresis loop at the pseudo coercive force Hc*, and the magnetic field amplitude $H_a$; in which the first and second relationships will be described later) between physical quantities as evaluating information for aged deterioration of the evaluation target austenitic stainless steel.

The measuring step is to measure the evaluation target austenitic stainless steel to obtain subject minor hysteresis loops, thereby obtaining measured values of the physical quantities (for example, the pseudo coercive force Hc* which is a value of the magnetic field intensity H where the value of the magnetic flux density B is zero, and the first ratio Ms/$\chi_H$*; in which the physical quantities will be described later) from the subject minor hysteresis loops.

The evaluating step is to evaluate the aged deterioration in the evaluation target austenitic stainless steel from the measured values (values of the physical quantities such as the previously mentioned pseudo coercive force Hc* and the first ratio Ms/$\chi_H$*) obtained in the measuring step and based on the correlations (for example, the previously mentioned first relationship and the second relationship) between physical quantities obtained in the information obtaining step.

In the above steps, each of the minor hysteresis loops is obtained for each magnetic field amplitude $H_a$ to be applied to the material, based on a relationship between the magnetic field intensity H and the magnetic flux density B of the austenitic stainless steel obtained by measuring the magnetic flux density B while stepwise changing the magnetic field amplitude $H_a$ within a range of the magnetic field intensity H lower than a saturation magnetic field intensity.

BEST MODE FOR CARRYING OUT THE INVENTION

The evaluating method of the present invention will be described hereinafter, based on data of actually conducted tests. To clarify a correlation between a mechanical property and a magnetic property of austenitic stainless steels, there were conducted a tensile test followed by a minor hysteresis loop test, by adopting austenitic stainless steel SUS304 such as generally used in an atomic reactor piping and a chemical plant, concerning an austenitic stainless steel SUS304 (hereinafter called "H-SUS304") including a larger amount of nickel component and a standard austenitic stainless steel SUS304 (hereinafter called "S-SUS304"). Herein, there were used a stainless steel SUS304L prescribed in JIS G4305 as the H-SUS304, and a stainless steel SUS304 prescribed in JIS G4305 as the S-SUS304.

Figure 1A:
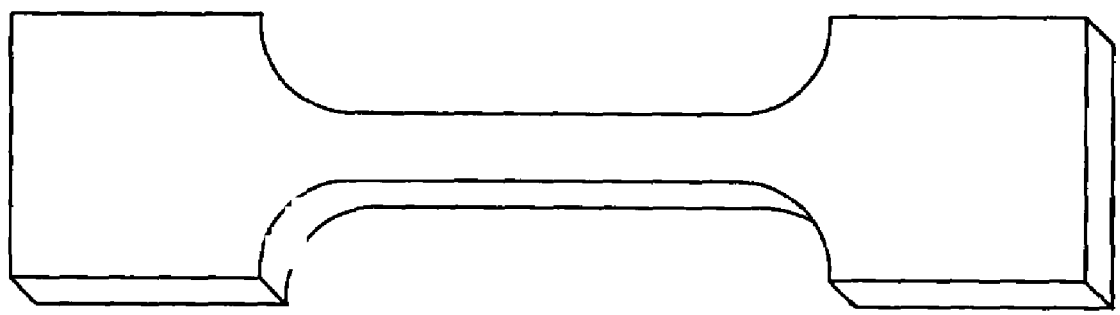
FIG. 1a is a perspective view showing a shape of a specimen for tensile deformation.
Figure 1B:
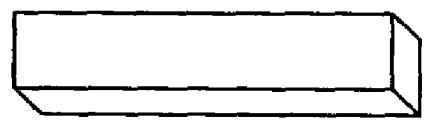
FIG. 1b is a perspective view showing a shape of a specimen upon measuring a minor hysteresis loop characteristic.
Figure 2:
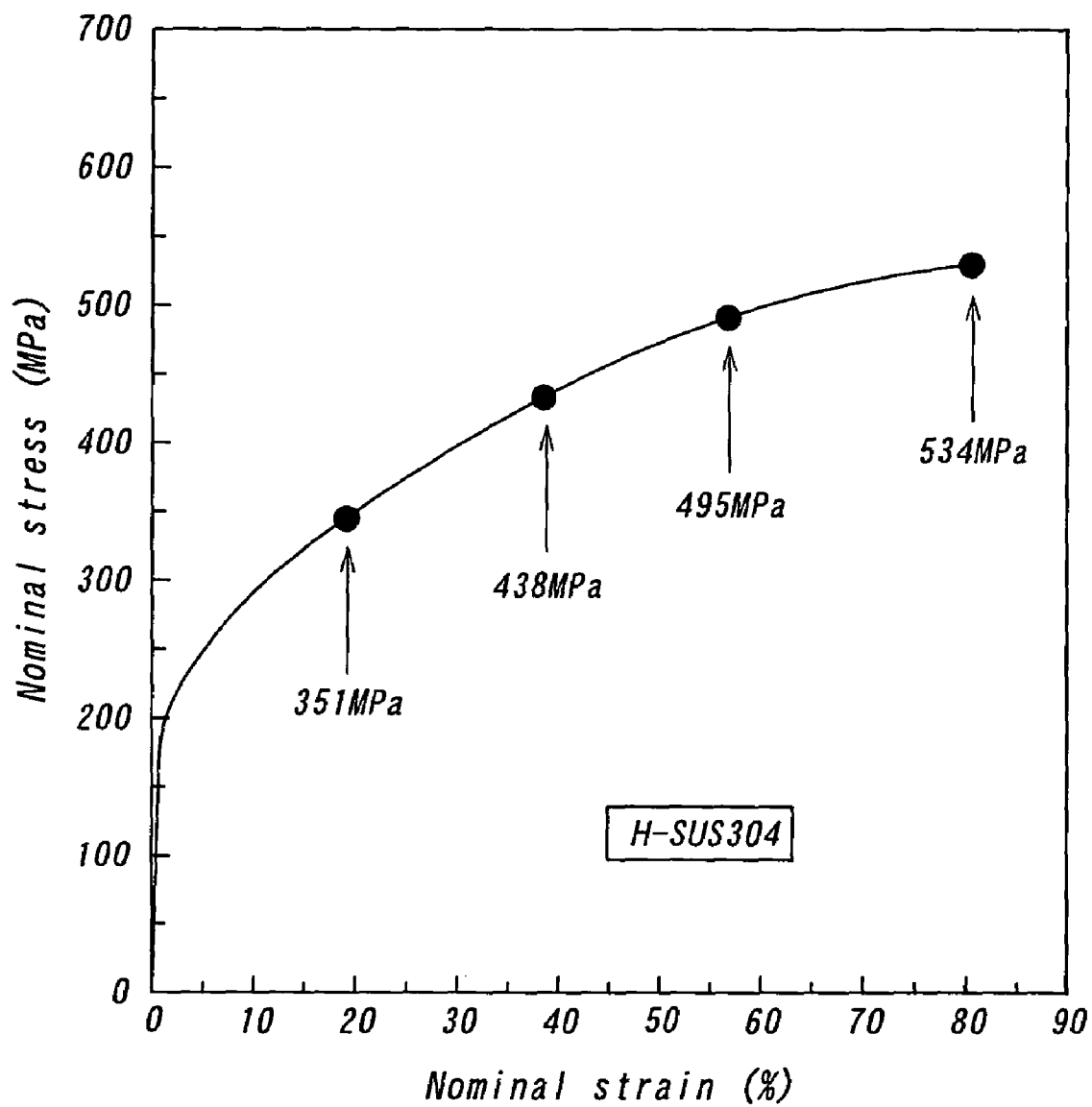
FIG. 2 is an explanatory view showing a stress-strain characteristic for exemplifying a result of tensile test in an austenitic stainless steel H-SUS304 including a larger amount of nickel component.
Figure 3:
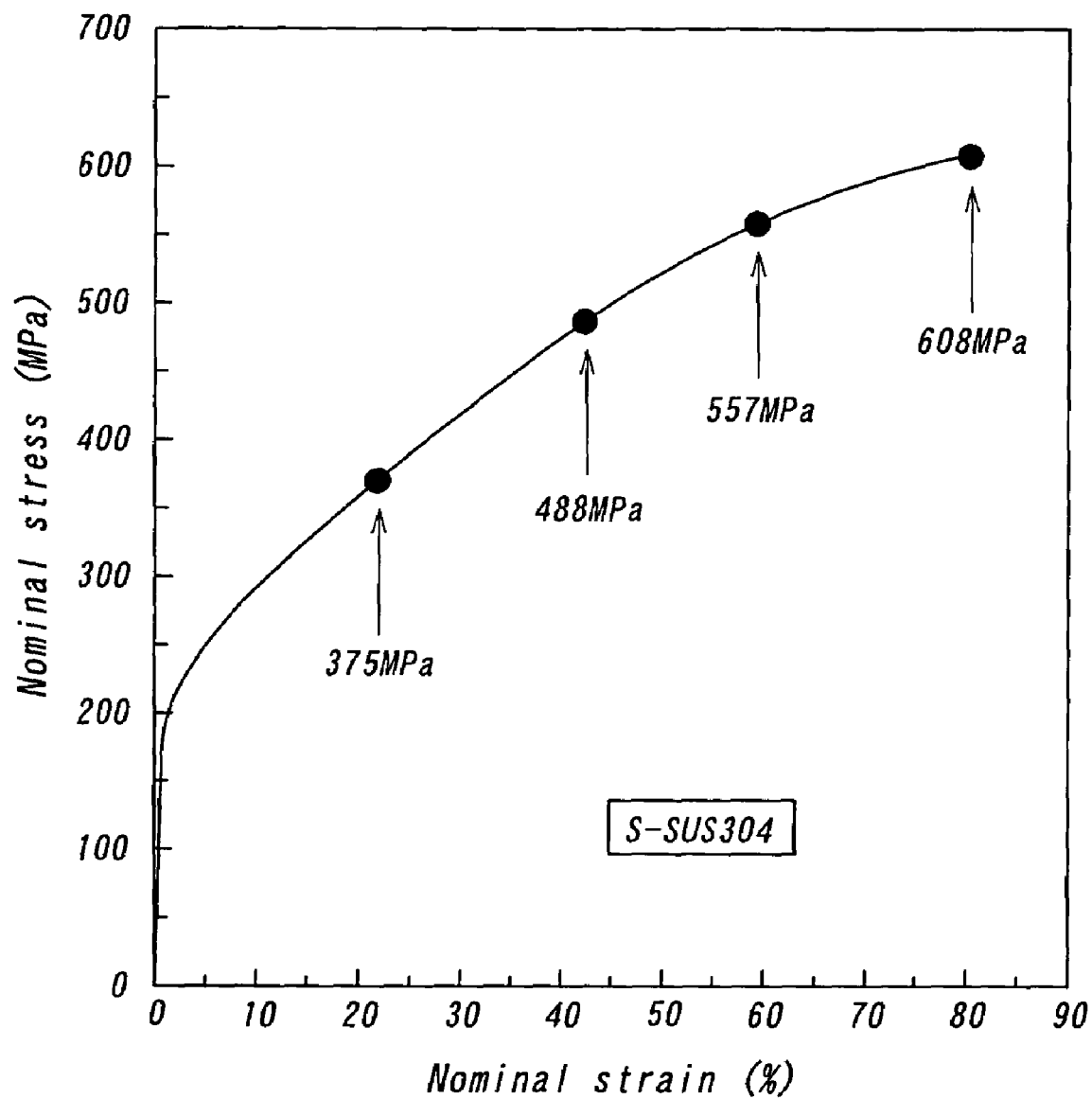
FIG. 3 is an explanatory view showing a stress-strain characteristic for exemplifying a result of tensile test in a standard austenitic stainless steel S-SUS304.

FIG. 1a shows a shape of a specimen used in the tensile test, and FIG. 1b shows a shape of a specimen used in the measurement of minor hysteresis loop characteristic. FIG. 2 is an explanatory view showing a stress-strain characteristic of the H-SUS304 obtained by conducting the tensile test for the specimen having the shape shown in FIG. 1a, and FIG. 3 is an explanatory view showing a stress-strain characteristic of the S-SUS304 obtained by conducting the tensile test for the specimen having the shape shown in FIG. 1a.

Further, the chemical compositions of the H-SUS304 and S-SUS304 used in the test are shown in Table 1. As a result of the tensile test, the specimens of H-SUS304 and S-SUS304 were broken when the applied stresses σ became larger than 534 [MPa] (see FIG. 2) and 608 [MPa] (see FIG. 3), respectively.

TABLE 1

| | (Wt %) | | | | | | | |
|---|---|---|---|---|---|---|---|---|
| | C | Cr | Ni | Mn | Si | P | S | Fe |
| H-SUS304 | 0.022 | 18.4 | 10.1 | 1.65 | 0.48 | 0.025 | 0.0009 | bal |
| S-SUS304 | 0.053 | 18.4 | 9.2 | 1.66 | 0.51 | 0.024 | 0.0009 | bal |

Figure 4:
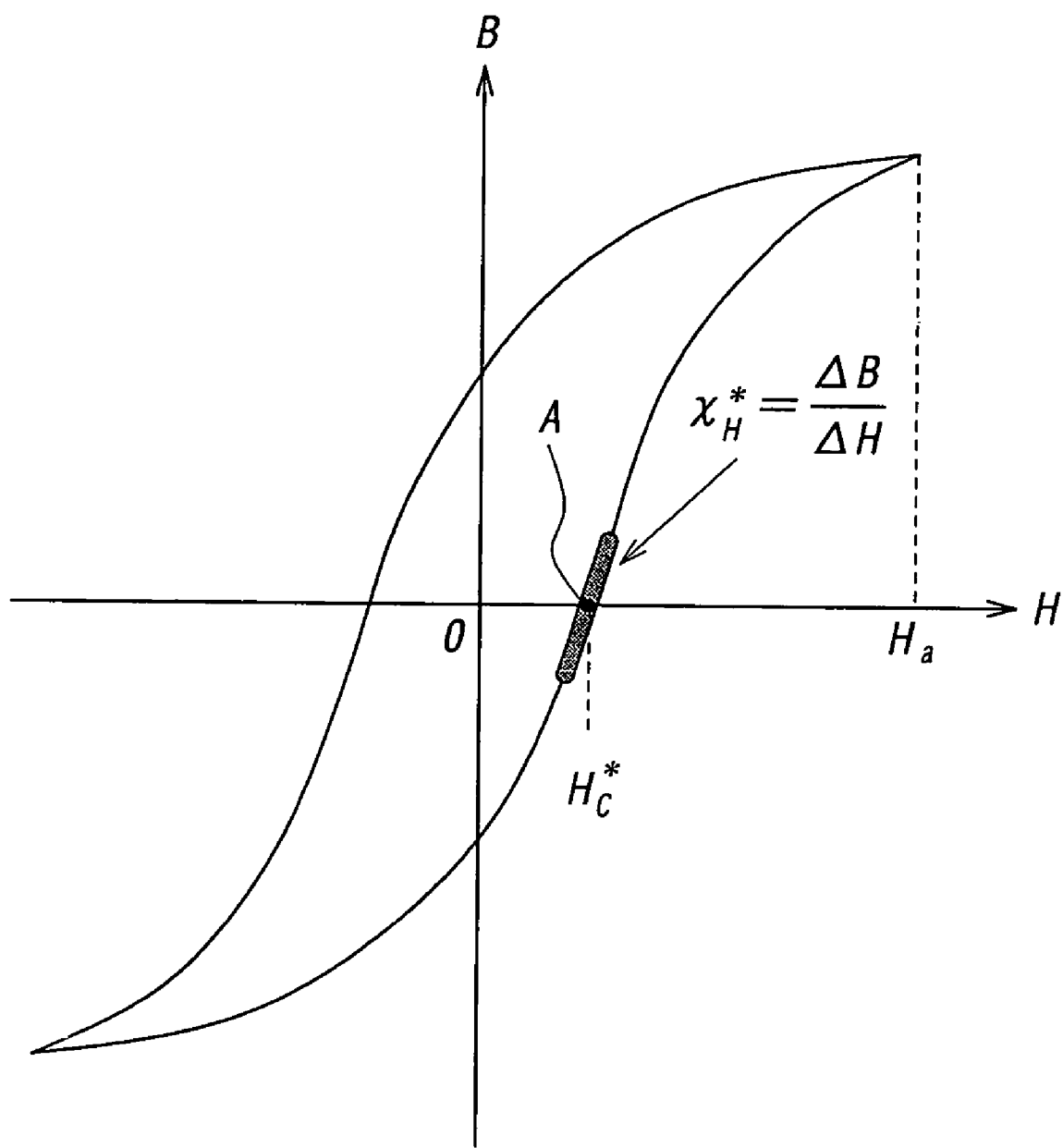
FIG. 4 is an explanatory view exemplifying and explaining a pseudo coercive force Hc*, a magnetic field amplitude $H_a$ and a pseudo susceptibility $\chi_H^*$.

Note, the above-mentioned minor hysteresis loop test is such one for conducting measurement by applying a magnetic field (having a magnetic field intensity on the order of two times the coercive force) to a material in which the magnetic field amplitude $H_a$ (i.e., the maximum value of the magnetic field intensity H) to be applied to the material is lower than the saturation magnetization, so as to obtain a curve (hereinafter called "minor hysteresis loop") corresponding to a hysteresis loop such as shown in FIG. 4.

This term "minor hysteresis loop test" is to be expediently used by the present inventor, so as to differentiate it from a hysteresis loop test to be generally conducted to obtain a major hysteresis loop by applying a magnetic field up to a saturating strength (i.e., magnetic field intensity on the order of several times to several tens times of the coercive force).

Concerning the minor hysteresis loop in the present specification, for differentiation from a coercive force and a susceptibility to be obtained from a major hysteresis loop, there are defined: a pseudo coercive force Hc* which corresponds to a coercive force, i.e., which is a value of a magnetic field intensity H where a value of a magnetic flux density B is zero; and a pseudo susceptibility $\chi_H^*$ (=ΔB/ΔH) which corresponds to a susceptibility, i.e., which is a gradient of the minor hysteresis loop at the pseudo coercive force Hc*; (see FIG. 4).

Note, the pseudo coercive force and the pseudo susceptibility are functions of the magnetic field intensity H, and match with the coercive force and the susceptibility obtained from the major hysteresis loop when the magnetic field intensity H is sufficiently high.

Figure 5:
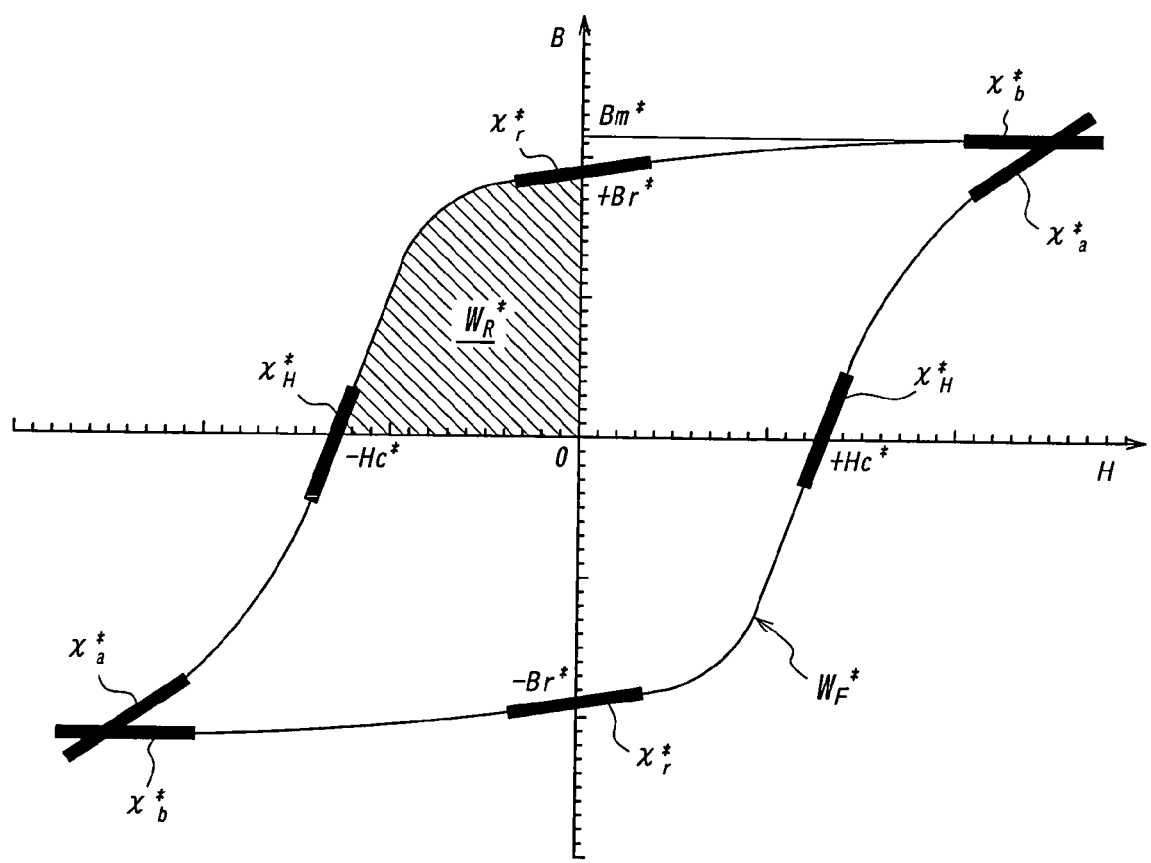
FIG. 5 is an explanatory view exemplifying and explaining a pseudo hysteresis loss $W_F^*$, a pseudo remanence work $W_R^*$, a pseudo remanence Br*, a pseudo magnetization Bm*, a pseudo remanence susceptibility $\chi_r^*$, a pseudo susceptibility $\chi_b^*$ and a pseudo susceptibility $\chi_a^*$ in a minor hysteresis loop.

Further, concerning the minor hysteresis loop in the present specification as shown in FIG. 5, there are defined: a pseudo hysteresis loss $W_F^*$ which is an area of portion surrounded by the minor hysteresis loop; a pseudo remanence work $W_R^*$ which is an area of the portion where the magnetic flux density B>0 and the magnetic field intensity H<0 within the area of the portion surrounded by the minor hysteresis loop; a pseudo remanence Br* which is a value of the magnetic flux density B where the value of the magnetic field intensity H is zero; a pseudo remanence susceptibility $\chi_r^*$ which is a gradient of the minor hysteresis loop at the pseudo remanence Br*; a pseudo magnetization Bm* which is a value of the magnetic flux density B at a magnetic field amplitude $H_a$; and a pseudo susceptibility $\chi_b{}^*$ and a pseudo susceptibility $\chi_a{}^*$ which are smaller and larger gradients, respectively, at the magnetic field amplitude $H_a$.

Further, based on the result of the above conducted tensile test, there is applied a predetermined stress to the specimen in the shape shown in FIG. 1b, the stress is then removed, and the minor hysteresis loop test is thereafter conducted for the thus deformed specimen while stepwise changing the magnetic field amplitude $H_a$ so as to obtain the minor hysteresis loop each time.

In this test, the magnetic field amplitude $H_a$ was stepwise increased within a range from 0 [Oe] to the order of 100 [Oe] so as to conduct measurement each time, thereby obtaining the minor hysteresis loop characteristics. Obtained from the resultant minor hysteresis loops are physical quantities to be described later, and these physical quantities are plotted to obtain correlations among physical quantities as shown in FIG. 6 through FIG. 32 to be described later.

Note, it will be described later that, more detailed information concerning aged deterioration in austenitic stainless steel is obtained by conducting measurement at the magnetic field amplitude $H_a$ on the order of 50 [Oe], according to the nondestructive evaluating method for aged deterioration in austenitic stainless steel of the present invention. Although the scale resolution of the magnetic field amplitude $H_a$ is set at 1 [Oe] in the measurement herein, it is natural that finer resolutions lead to increased amounts of information.

Among FIG. 6 through FIG. 32, FIGS. 6, 8, 10, 12, 15, 17, 19, 21, 23, 25, 27, 29 and 31 concerning H-SUS304 show those correlations (relationships obtained based on changes of minor hysteresis loop characteristics accompanying to deformation of specimens) among physical quantities obtained by conducting the minor hysteresis loop test for austenitic stainless steel after applying the applied stresses σ=351 [MPa], 438 [MPa], 495 [MPa] and 534 [MPa] to the austenitic stainless steel, and so do FIGS. 7, 9, 11, 13, 16, 18, 20, 22, 24, 26, 28, 30 and 32 concerning S-SUS304 after applying the applied stresses σ=375 [MPa], 488 [MPa], 557 [MPa] and 608 [MPa] thereto, respectively.

Note, the values of applied stress σ shown in the correlations of physical quantities have been selected within a range from absence of stress up to just before the breaking, based on the result of the previously conducted tensile test.

Thus, as shown in FIGS. 6, 8, 10, 12, 15, 17, 19, 21, 23, 25, 27, 29 and 31, the H-SUS304 is plotted by a black square, a white circle, an upward white triangle, and a downward black triangle in the order of stresses σ=351 [MPa], 438 [MPa], 495 [MPa] and 534 [MPa], respectively. Further, as shown in FIGS. 7, 9, 11, 13, 16, 18, 20, 22, 24, 26, 28, 30 and 32, the S-SUS304 is plotted by a black square, a white circle, an upward white triangle, and a downward black triangle in the order of stresses σ=375 [MPa], 488 [MPa], 557 [MPa] and 608 [MPa], respectively.

The reason, why the values of applied stress σ do not include the value σ=0 [MPa] before application of stress, is that the specimen of austenitic stainless steel before application of stress is not ferromagnetic but paramagnetic so that minor hysteresis loop characteristics are not obtained. As such, it is also impossible to obtain those values (such as the first ratio $Ms/\chi_H{}^*$, the second ratio $W_R{}^*/W_F{}^*$, the third ratio $Br^*/Bm^*$, the fourth ratio $\chi_r{}^*/\chi_H{}^*$ and the fifth ratio $\chi_b{}^*/\chi_a{}^*$ to be described later) to be obtained from the minor hysteresis loop characteristics, concerning the austenitic stainless steel before application of stress.

Figure 6:
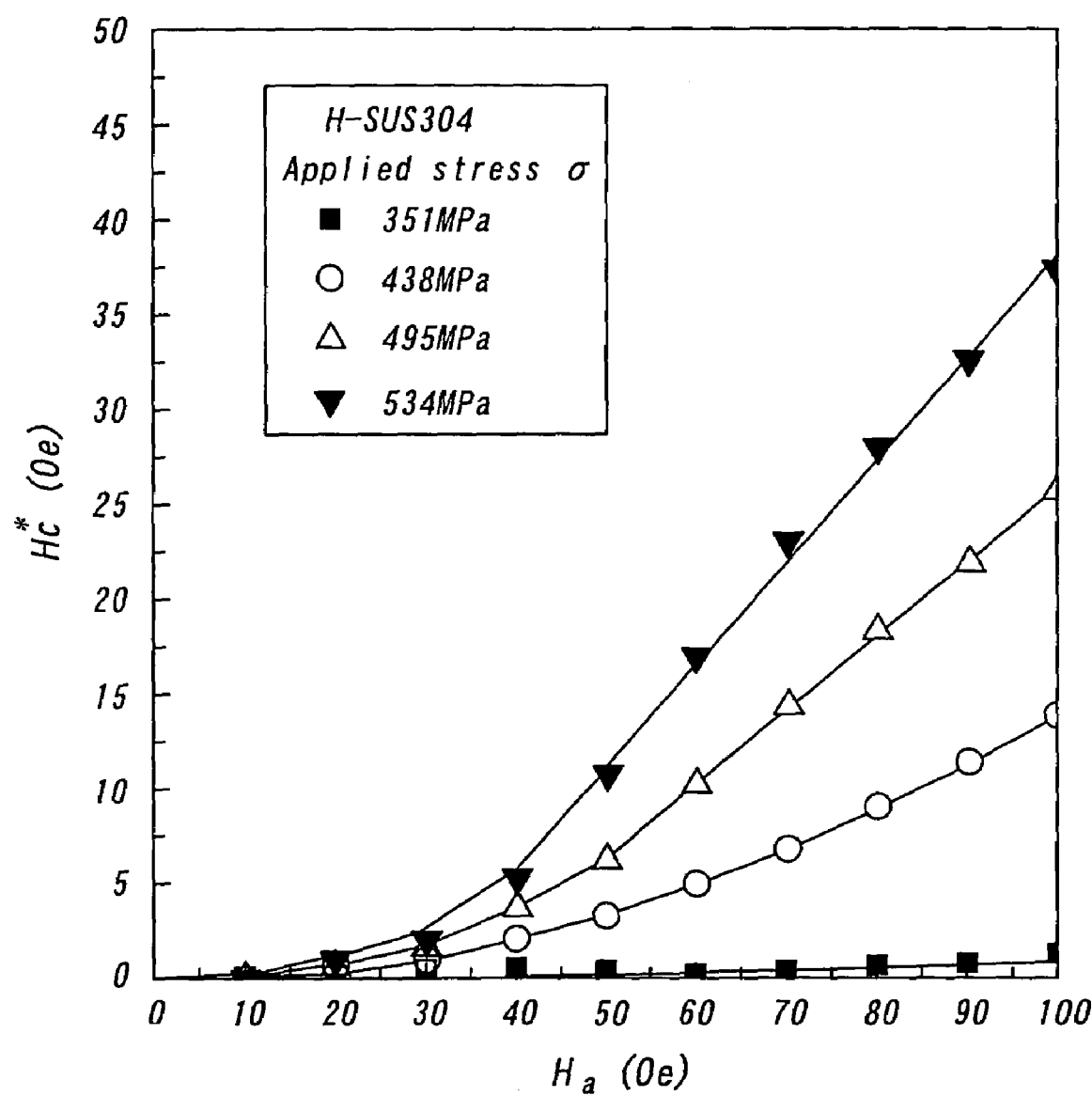
FIG. 6 is an explanatory view showing a relationship between the pseudo coercive force Hc* and the magnetic field amplitude $H_a$ obtained by a minor hysteresis loop test for H-SUS304 after applying the applied stresses σ=351, 438, 495 and 534 [MPa] thereto, respectively.
Figure 7:
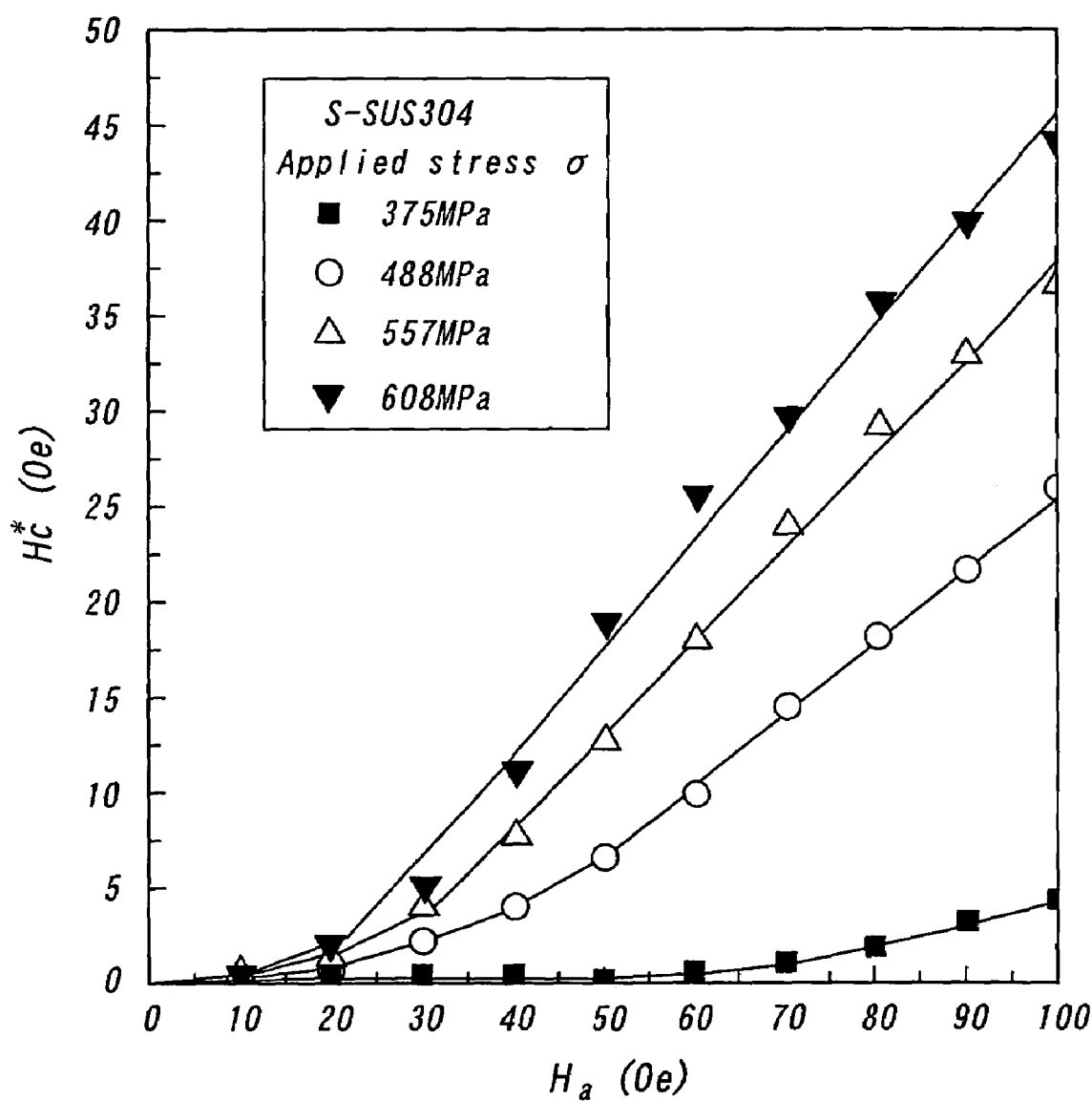
FIG. 7 is an explanatory view showing a relationship between the pseudo coercive force Hc* and the magnetic field amplitude $H_a$ obtained by the minor hysteresis loop test for S-SUS304 after applying the applied stresses σ=375, 488, 557 and 608 [MPa] thereto, respectively.
Figure 8:
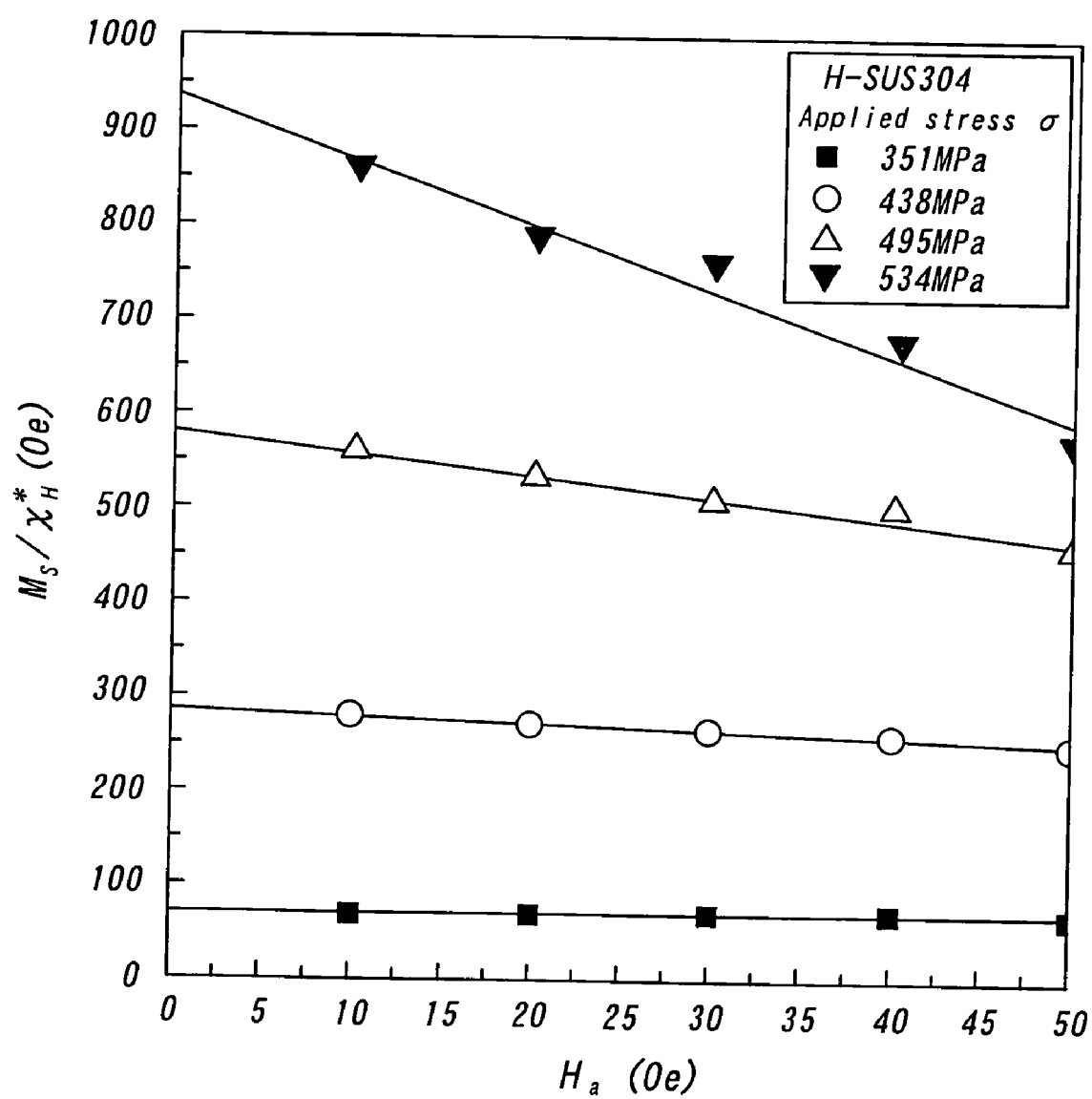
FIG. 8 is an explanatory view showing a relationship between the first ratio Ms/$\chi_H^*$ and the magnetic field amplitude $H_a$ obtained by the minor hysteresis loop test for H-SUS304 after applying the applied stresses σ=351, 438, 495 and 534 [MPa] thereto, respectively.
Figure 9:
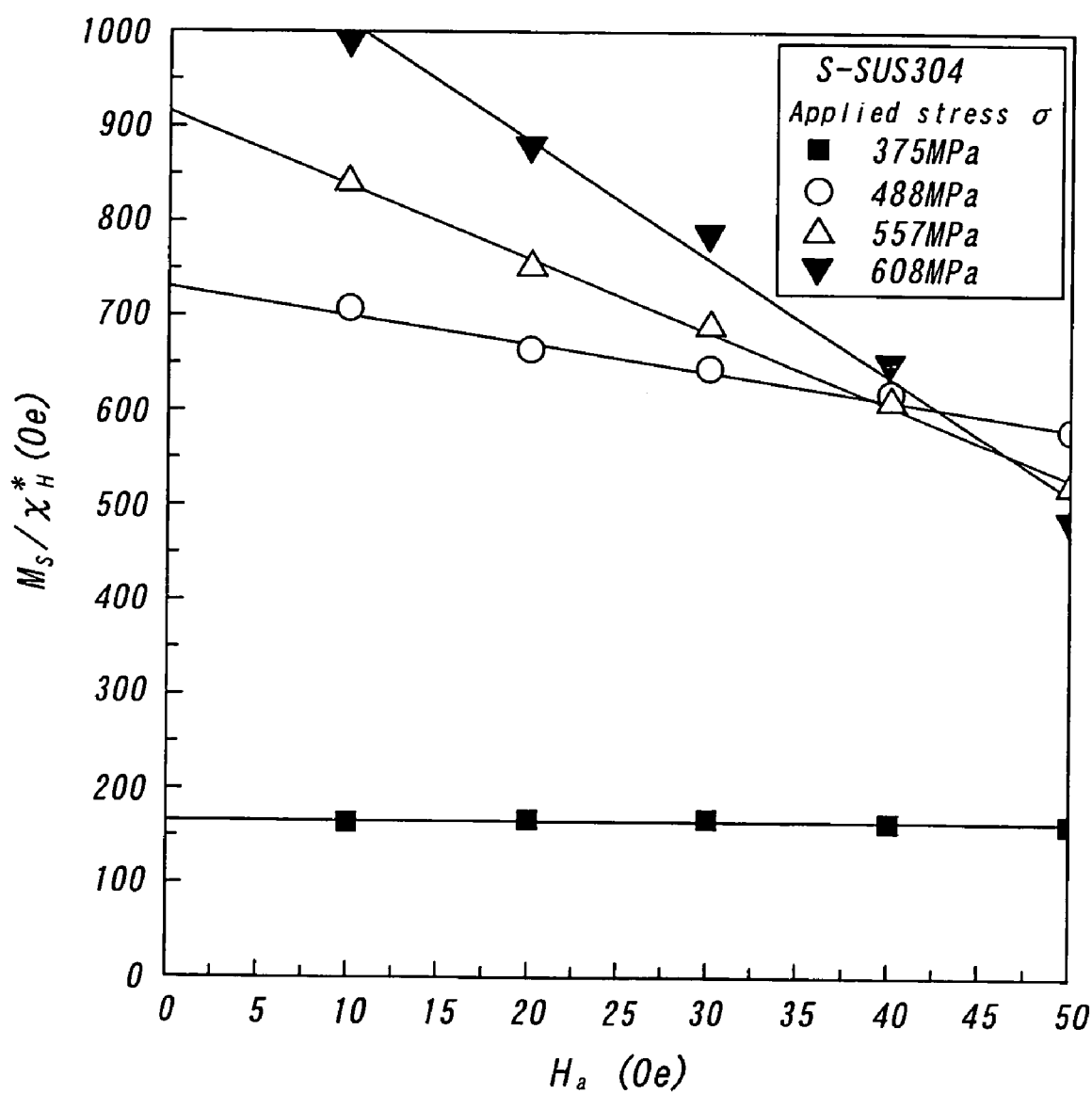
FIG. 9 is an explanatory view showing a relationship between the first ratio Ms/$\chi_H^*$ and the magnetic field amplitude $H_a$ obtained by the minor hysteresis loop test for S-SUS304 after applying the applied stresses σ=375, 488, 557 and 608 [MPa] thereto, respectively.

Herein, FIG. 6 and FIG. 7 show applied-stress dependencies concerning the relationships between the pseudo coercive force Hc* and the magnetic field amplitude $H_a$, respectively, and FIG. 8 and FIG. 9 show applied-stress dependencies concerning the relationships between the first ratio $Ms/\chi_H{}^*$ and the magnetic field amplitude $H_a$, respectively.

Figure 10:
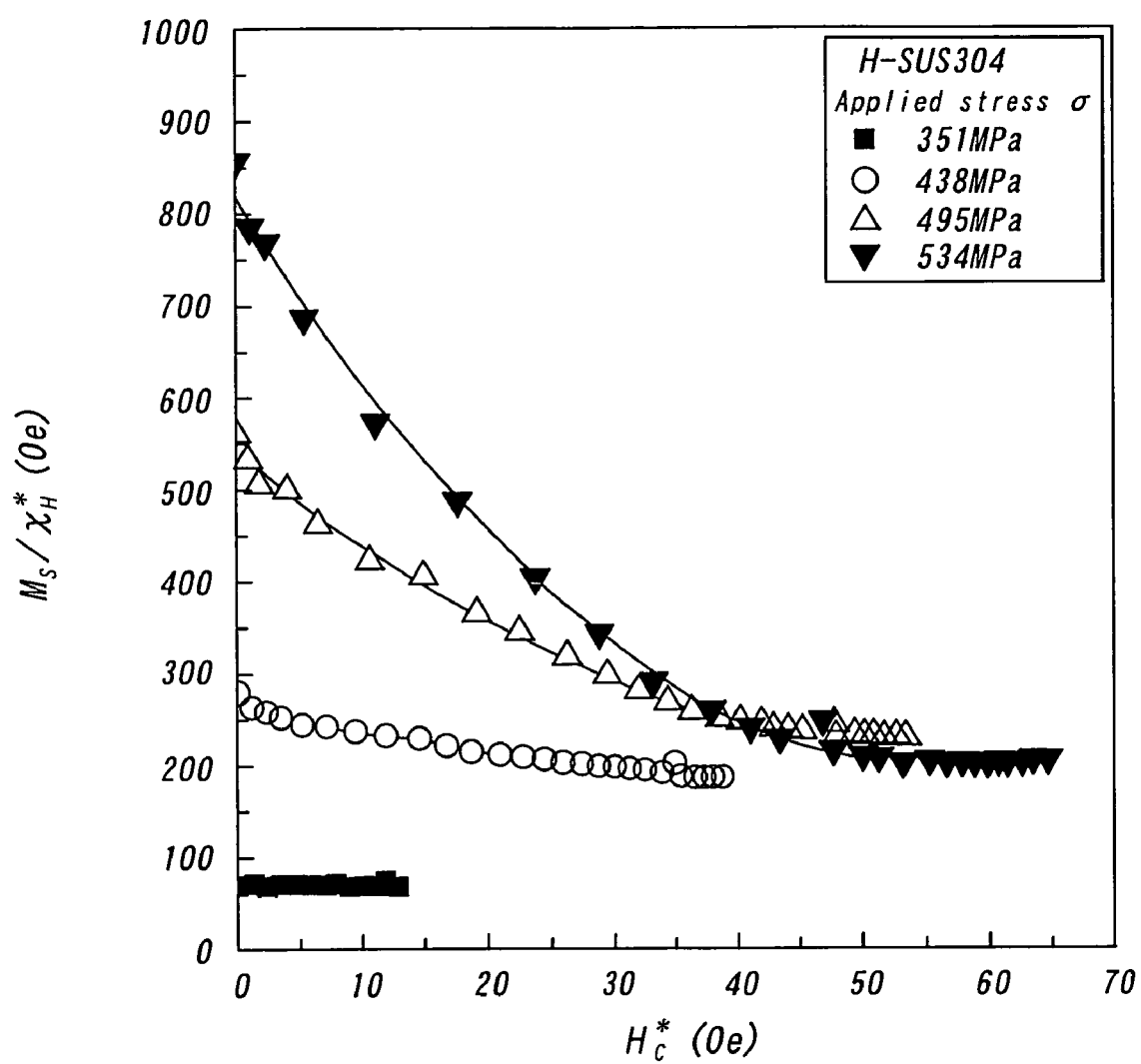
FIG. 10 is an explanatory view showing a relationship between the first ratio Ms/$\chi_H^*$ and the pseudo coercive force Hc* for H-SUS304, obtained from the relationships of FIG. 6 and FIG. 8.
Figure 11:
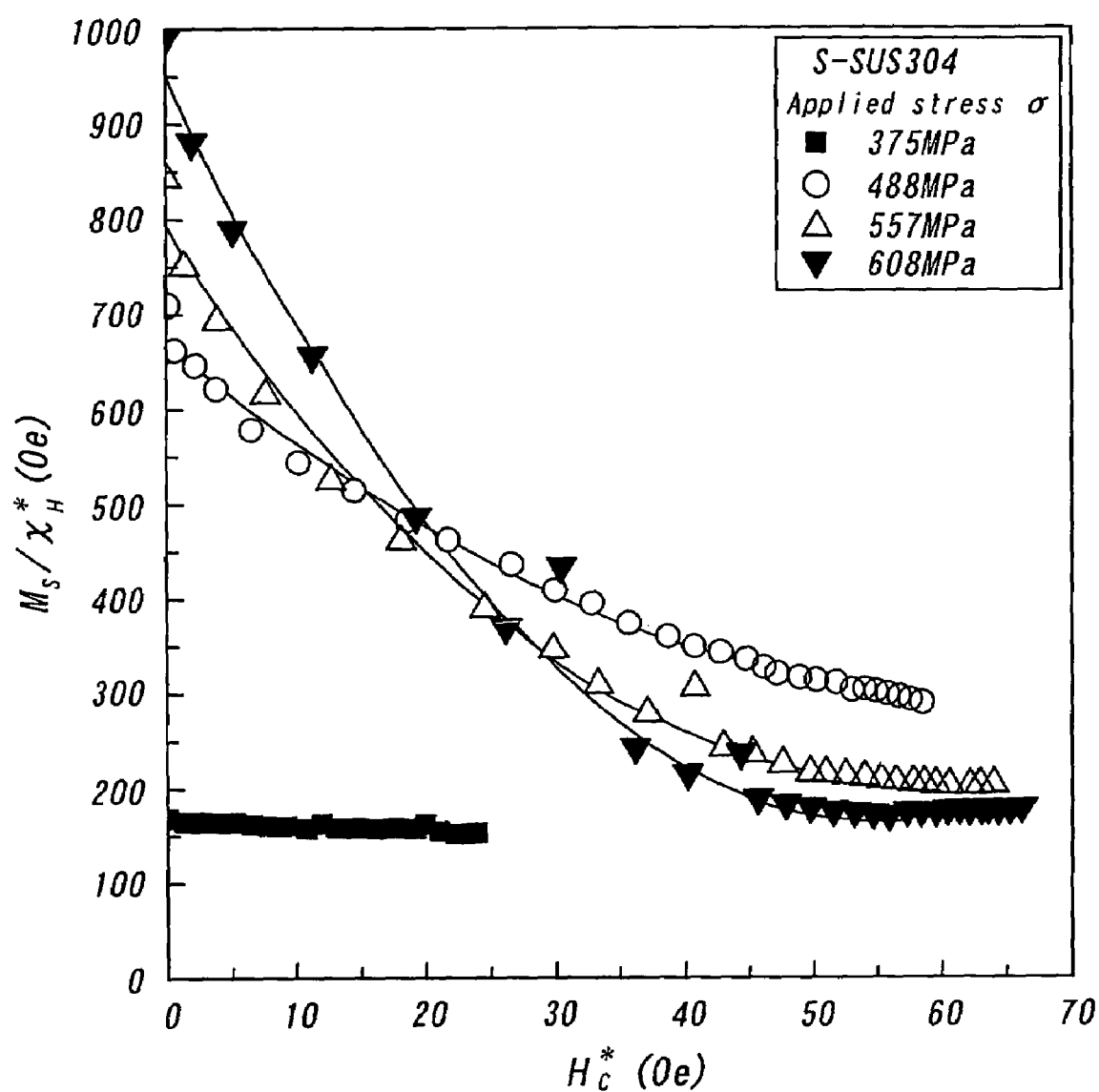
FIG. 11 is an explanatory view showing a relationship between the first ratio Ms/$\chi_H^*$ and the pseudo coercive force Hc* for S-SUS304, obtained from the relationships of FIG. 7 and FIG. 9.
Figure 12:
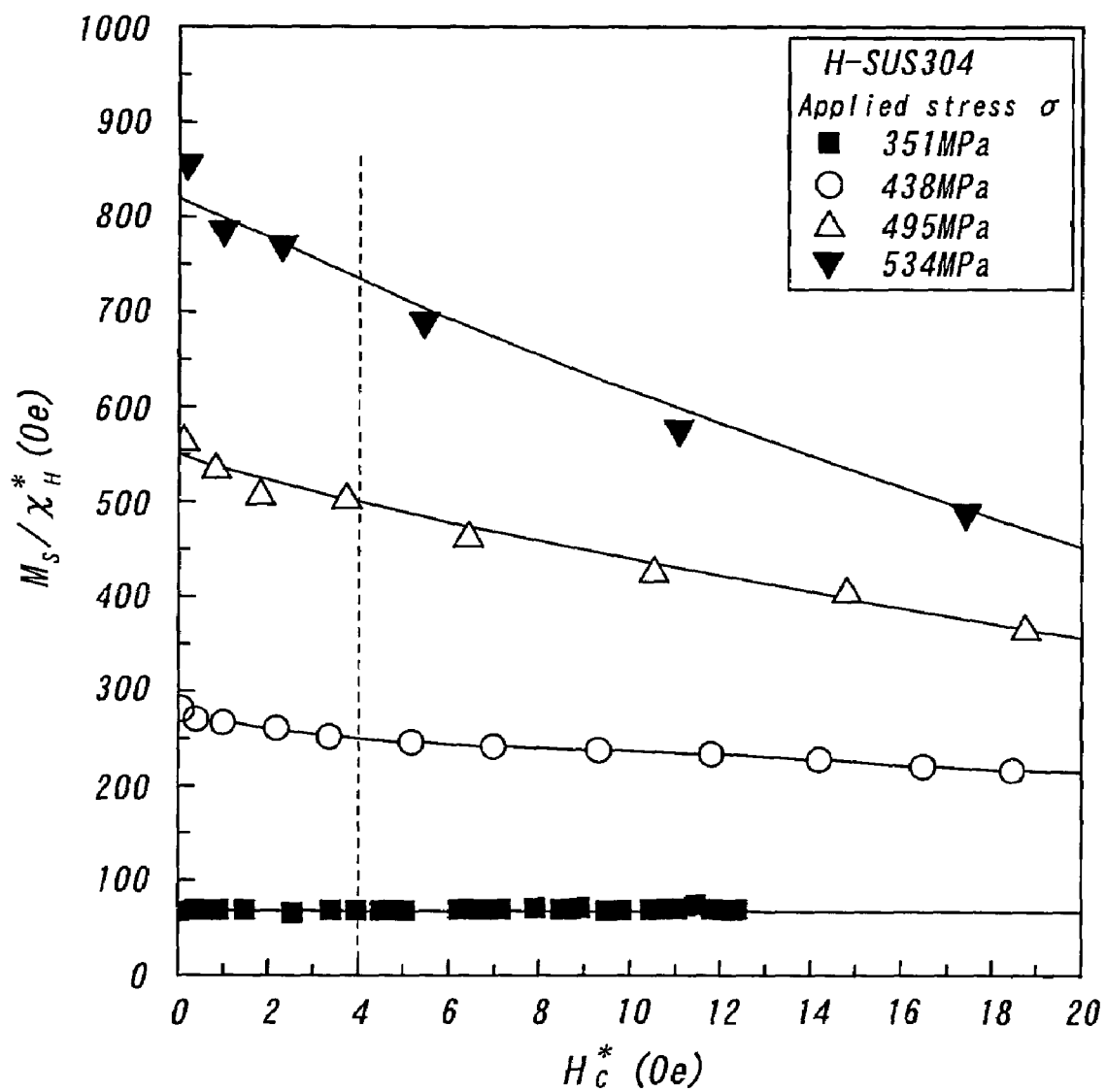
FIG. 12 is a partially enlarged view showing a relationship between the first ratio Ms/$\chi_H^*$ and the pseudo coercive force Hc* for H-SUS304 shown in FIG. 10, within a range of 0 to 20 [Oe] of the pseudo coercive force Hc*.
Figure 13:
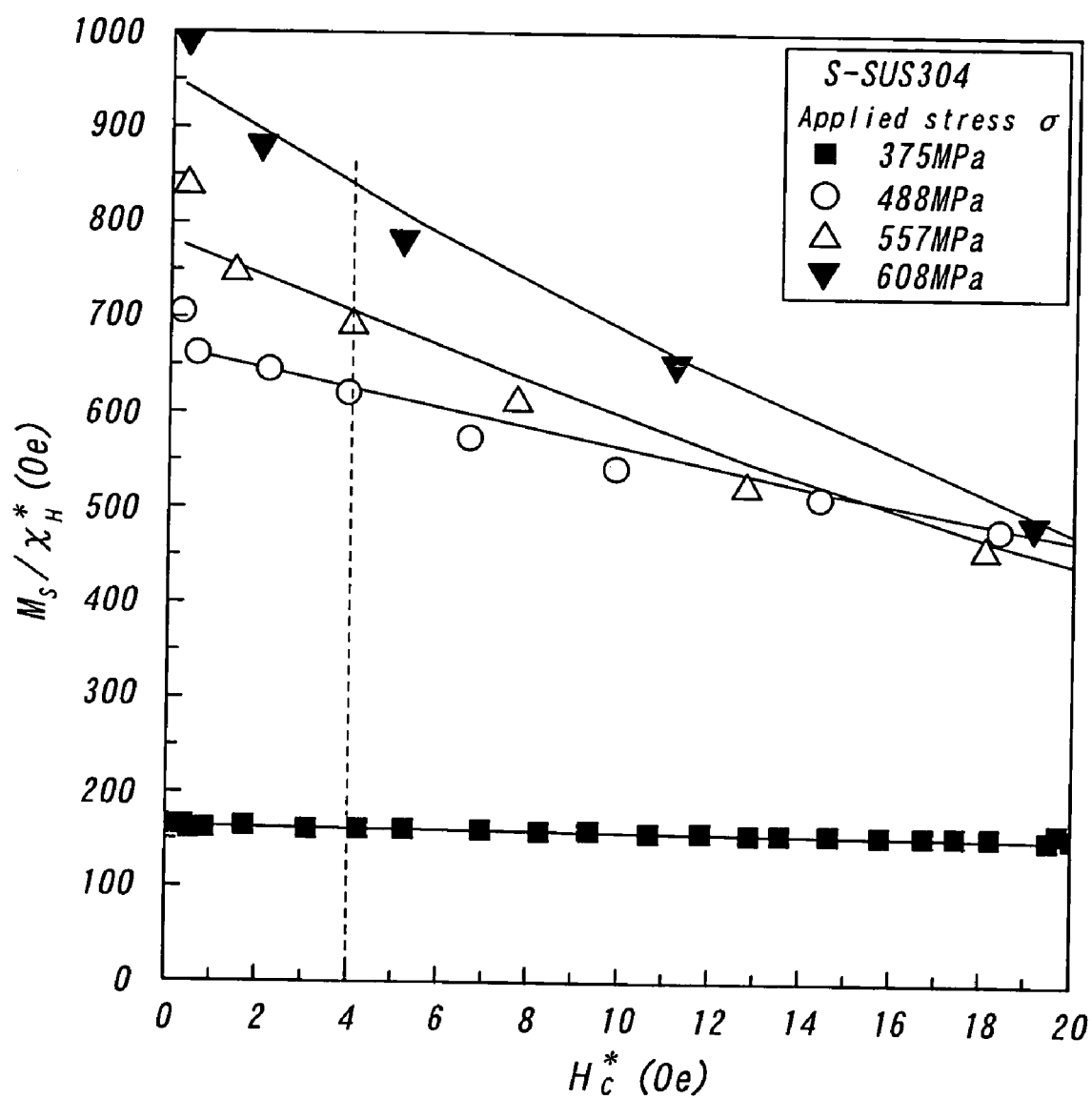
FIG. 13 is a partially enlarged view showing a relationship between the first ratio Ms/$\chi_H^*$ and the pseudo coercive force Hc* for S-SUS304 shown in FIG. 11, within a range of 0 to 20 [Oe] of the pseudo coercive force Hc*.

Further, FIG. 10 and FIG. 11 show relationships between the pseudo coercive force Hc* and the first ratio $Ms/\chi_H{}^*$ obtained from the relationships shown in FIG. 6 through FIG. 9, respectively, and FIG. 12 and FIG. 13 are partially enlarged views showing the relationships shown in FIG. 10 and FIG. 11 within ranges of 0 to 20 [Oe] of the pseudo coercive force Hc*, respectively.

As shown in the relational diagrams of FIG. 12 and FIG. 13, it is understood that the relationship between the pseudo coercive force Hc* and the first ratio $Ms/\chi_H{}^*$ is changed as the applied stress σ is increased. Note, the situations of the applied stress σ=534 [MPa] for H-SUS304 shown in FIG. 12 and the applied stress σ=608 [MPa] for S-SUS304 shown in FIG. 13 represent the relationships between the pseudo coercive force Hc* and the first ratio $Ms/\chi_H{}^*$ just before the breaking of the specimens, respectively.

Based on the above, it has become apparent from the study of the present inventor that the relationship between the pseudo coercive force Hc* and the first relationship has an intimate correlation with the internal factor (internal stress) which transforms the austenite phase to the martensitic phase, because the above applied stress σ can be substituted for the internal factor. Further, the first ratio $Ms/\chi_H{}^*$ does not depend on the amount of the martensitic phase, because the first ratio $Ms/\chi_H{}^*$ is normalized by the saturation magnetization Ms.

Note, to obtain the value of the first ratio $Ms/\chi_H{}^*$, it is required to obtain the value of the saturation magnetization Ms, and there is required a magnetic field intensity H on the order of 3T ($=3\times10^4$ [Oe]) to obtain the saturation magnetization Ms due to the martensitic phase introduced in an austenitic stainless steel by plastic deformation.

However, it is difficult to constitute a measuring apparatus for applying such a high magnetic field intensity H in an actual measurement of an austenitic stainless steel structural material. It is thus considered to be extremely difficult to apply the magnetic field of such the high magnetic field intensity H to an austenitic stainless steel structural material, and the limitation allowed for magnetization measurement is considered to be a magnetic field intensity H on the order of 100 [Oe] at the utmost. There will be thus explained hereinafter a method for expediently obtaining the saturation magnetization Ms by the magnetic field intensity H on the order of 100 [Oe].

Figure 14:
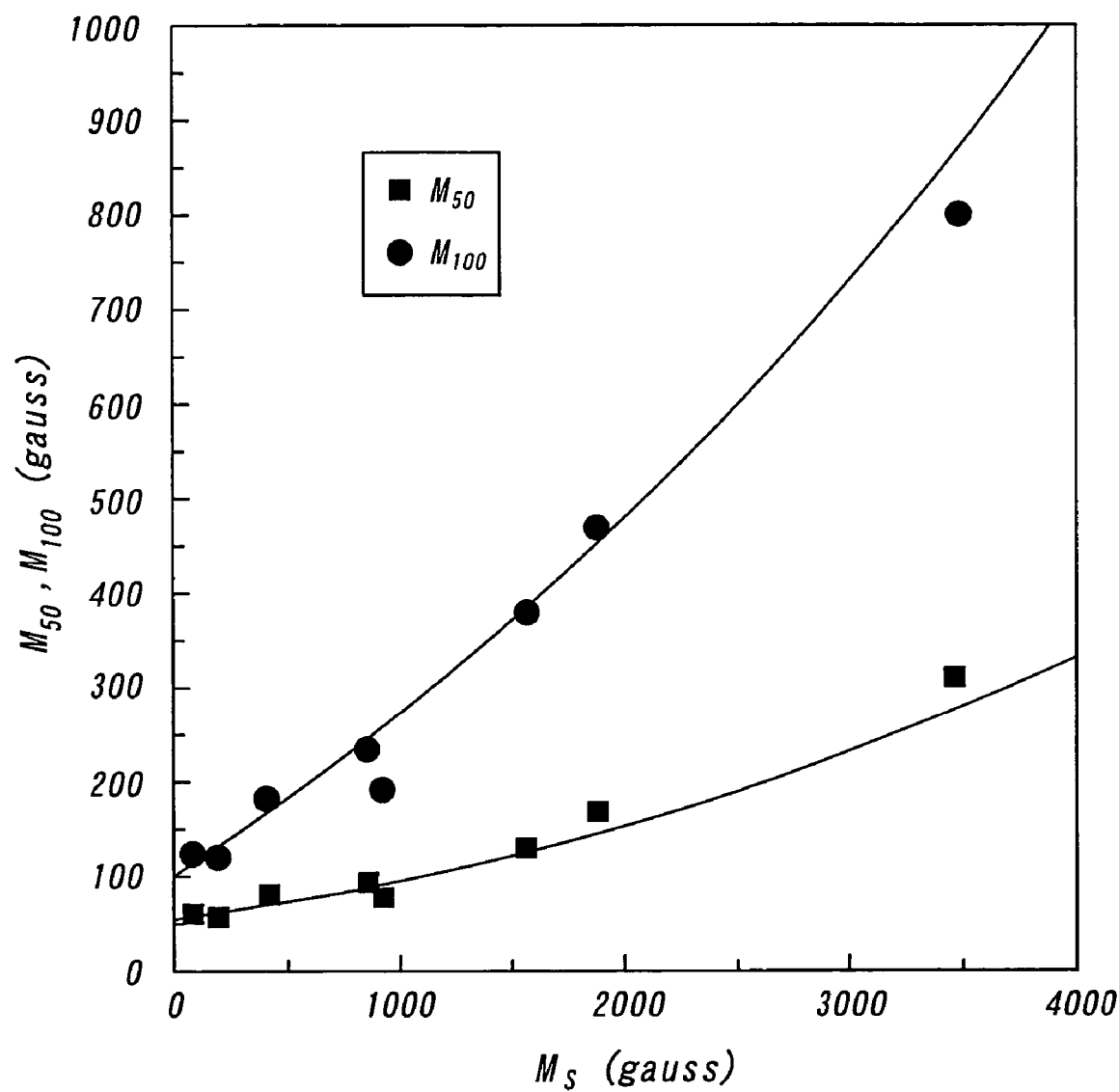
FIG. 14 is an explanatory view showing a relationship between: magnetization $M_{100}$ [gauss] and magnetization $M_{50}$ [gauss] obtained by measurement at magnetic field intensities H of 100 [Oe] and 50[Oe]; and a saturation magnetization Ms [gauss] obtained by measurement at the high magnetic field intensity H of 3T (=3×10⁴ [Oe]); for specimens of austenitic stainless steels H-SUS304 and S-SUS304 caused with plastic deformation.

FIG. 14 shows a relationship between a saturation magnetization Ms [gauss] obtained by measurement at the high magnetic field intensity H of 3T ($=3\times10^4$ [Oe]) and a magnetization $M_{100}$ [gauss] obtained by measurement at 100 [Oe], concerning the specimens of austenitic stainless steels S-SUS304 and H-SUS304 applied with plastic deformation.

In FIG. 14, the relationship between the saturation magnetization Ms and the magnetization $M_{100}$ is plotted by a black circle, and the relationship between the saturation magnetization Ms and the magnetization $M_{50}$ [gauss] to be described later is plotted by a black square. Here, the measurement is conducted by setting the magnetic field amplitude $H_a$ to be 100 [Oe] upon measuring the minor hysteresis loop characteristic, and the value of the magnetization at the magnetic field amplitude $H_a$ is obtained as the magnetization $M_{100}$.

From the relationship between the saturation magnetization Ms and the magnetization $M_{100}$, it is understood that, even without measurement at the high magnetic field intensity H of 3T, there can be obtained the values of saturation magnetization Ms similar to those of the saturation magnetization Ms which are obtained upon measurement at the high magnetic field intensity H of 3T, by conducting the measurement while setting the magnetic field amplitude $H_a$ to be 100 [Oe] to thereby obtain the magnetization $M_{100}$.

Also shown in FIG. 14 is a relationship between the saturation magnetization Ms obtained by the measurement at the high magnetic field intensity H of 3T, and a magnetization $M_{50}$ obtained by measurement at the magnetic field intensity H of 50 [Oe].

It is understood from the result shown in FIG. 14 that the values of saturation magnetization Ms can be obtained also from the minor hysteresis loop characteristics obtained by measurement while setting the values of the magnetic field amplitude $H_a$ at 50 [Oe], though the relationship obtained by the measurement while setting the magnetic field amplitude $H_a$ at 50 [Oe] has a slightly lower sensitivity as compared with the relationship obtained by the measurement while setting the value of the magnetic field amplitude $H_a$ at 100 [Oe].

Note, even when the whole relationship between the pseudo coercive force Hc* and the first ratio Ms/$\chi_H$* shown in FIG. 10 through FIG. 13 are not obtained by measurement, the progressing state of aged deterioration of austenitic stainless steel is obtained from the relationship at a portion where the value of the pseudo coercive force Hc* is small, thereby making it possible to evaluate the aged deterioration in a manner to be described hereinafter.

Namely, although the relationships shown in FIG. 10 through FIG. 13 are obtained by applying the magnetic field amplitude $H_a$ up to 100 [Oe], for example, there can be obtained the relationship between the first ratio Ms/$\chi_H$* and the pseudo coercive force Hc* where pseudo coercive force Hc*=4 [Oe] or less in FIG. 12 and FIG. 13 (i.e., those regions at the left of broken lines in FIG. 12 and FIG. 13, respectively), even by the result where the magnetic field amplitude $H_a$ is applied up to 100 [Oe]. It is thus possible to sufficiently evaluate the aged deterioration in austenitic stainless steel, based on these relationships.

Figure 15:
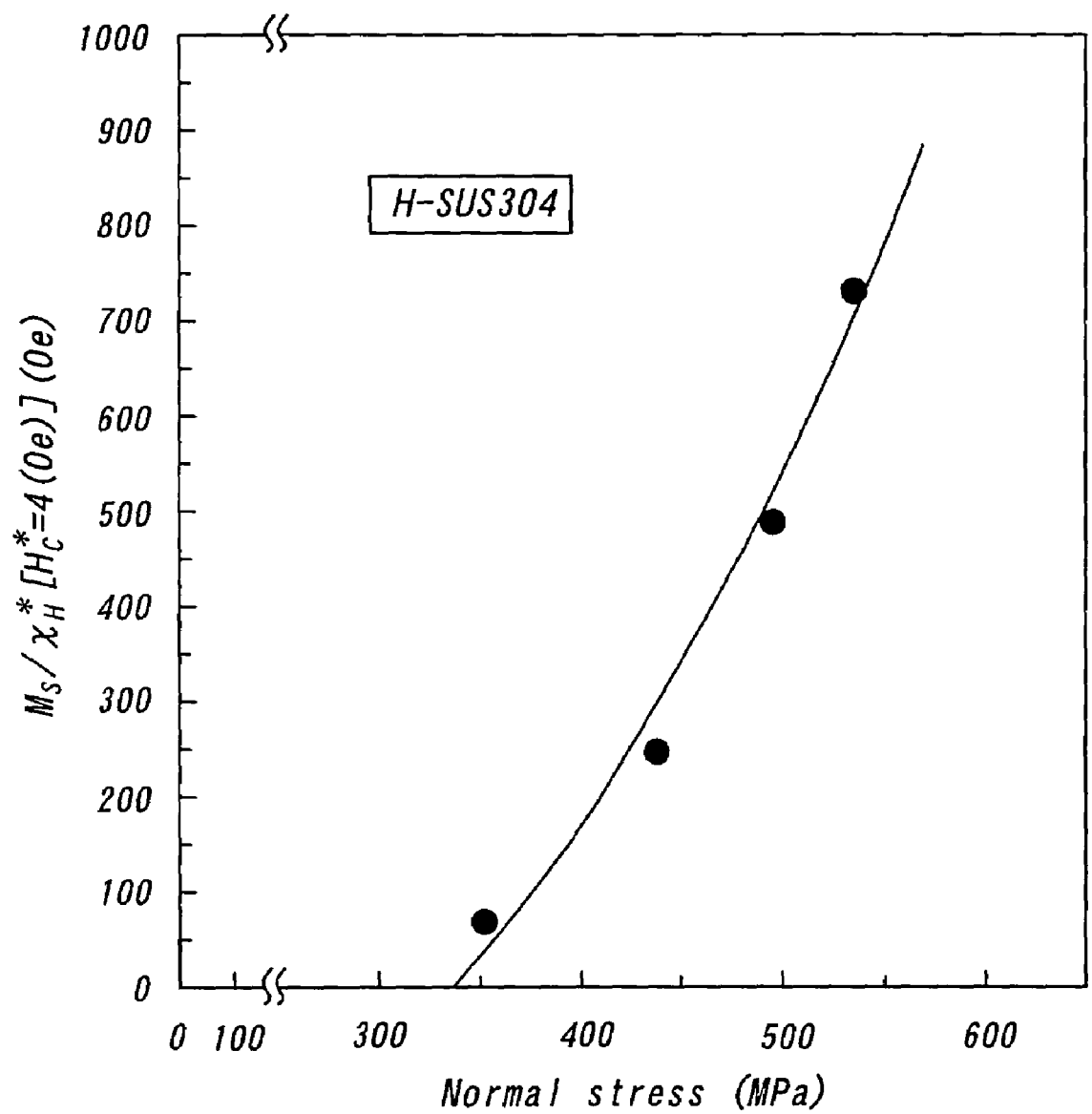
FIG. 15 is an explanatory view showing a relationship between the first ratio Ms/$\chi_H^*$ and a nominal stress (applied stress σ) for the H-SUS304 at the pseudo coercive force Hc*=4 [Oe] shown in FIG. 12.
Figure 16:
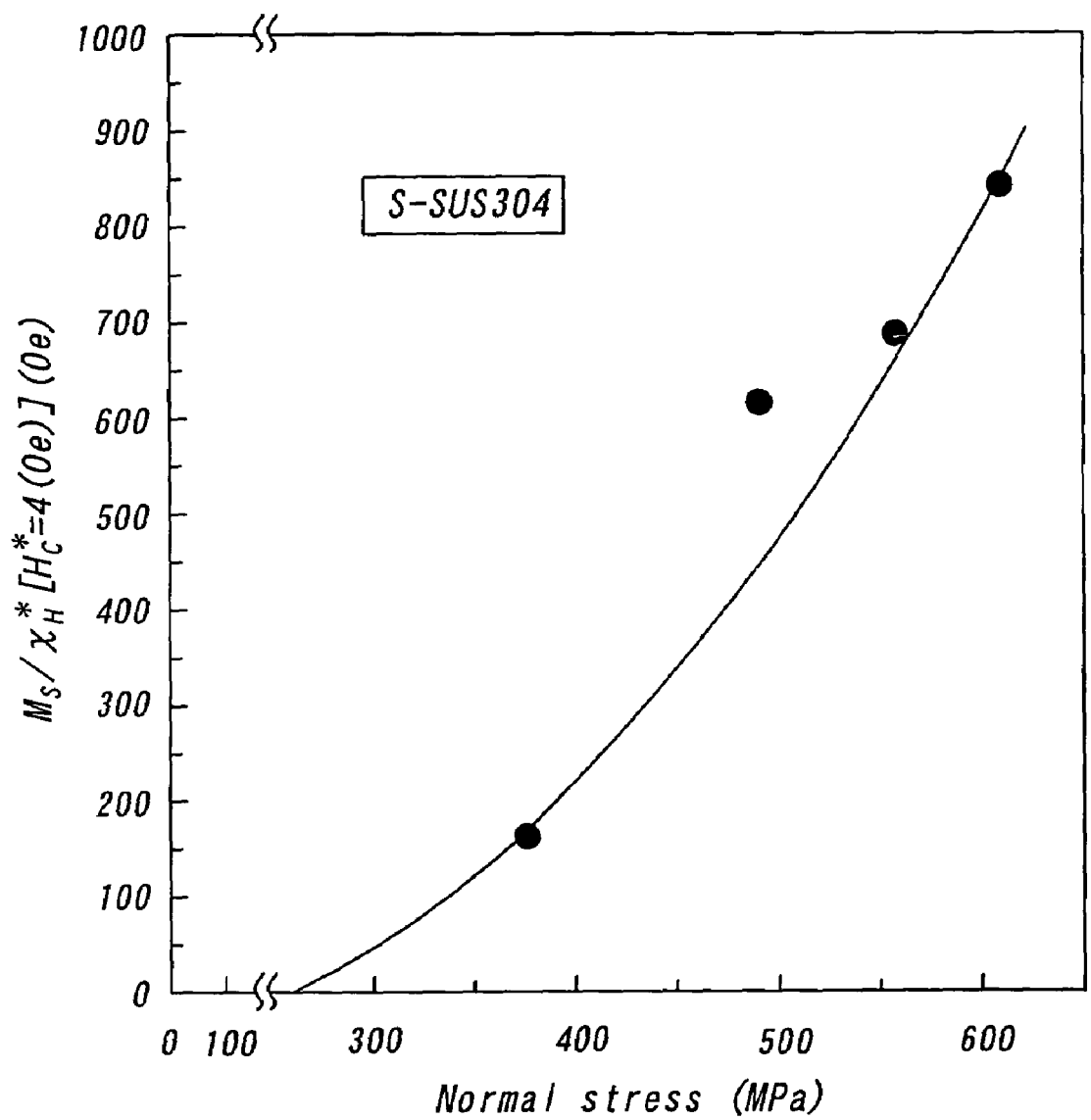
FIG. 16 is an explanatory view showing a relationship between the first ratio Ms/$\chi_H^*$ and a nominal stress (applied stress σ) for the S-SUS304 at the pseudo coercive force Hc*=4 [Oe] shown in FIG. 13.

Further, FIG. 15 shows a relationship between a nominal stress (applied stress σ) and the first ratio Ms/$\chi_H$* at the pseudo coercive force Hc*=4 [Oe] concerning the H-SUS304 shown in FIG. 12, and FIG. 16 shows a relationship between a nominal stress (applied stress σ) and the first ratio Ms/$\chi_H$* at the pseudo coercive force Hc*=4 [Oe] concerning the S-SUS304 shown in FIG. 13.

As shown in these FIG. 15 and FIG. 16, it is possible to know an extent of aged deterioration or a change of dislocation density as described later even from a relational diagram obtained by measurement based on a weak magnetic field, by conducting measurement by a minor hysteresis loop test concerning an austenitic stainless steel as an evaluation target so as to obtain the values of the first ratio Ms/$\chi_H$*. Namely, this means that it is possible to sufficiently evaluate aged deterioration in austenitic stainless steel, even based on the information derived from measurement at a weak magnetic field.

Incidentally, although austenitic stainless steel is paramagnetic, the martensitic phase introduced thereinto by plastic deformation is ferromagnetic. Within this martensitic phase, the progressed metal fatigue leads to a higher dislocation density. Further, the domain walls within the martensitic phase become difficult to move as the dislocation density is increased.

The value of the first ratio Ms/$\chi_H$* represents a resistance of the domain walls movement, and is increased as the dislocation density is increased. Further, the pseudo coercive force Hc* is the magnetic field intensity where the pseudo susceptibility $\chi_H$* becomes maximum within the magnetic field amplitude $H_a$. Thus, changing the magnetic field amplitude $H_a$ enables to grasp the whole image of the potential energy of the domain wall movements.

Thus, according to the evaluating method of the present invention having the above constitution, there can be obtained magnitudes of forces exerted on domain walls in the martensitic phase as well as the distribution of the magnitudes, based on the correlations between physical quantities obtained in an information obtaining step, such as the first relationship of the relationship between the pseudo coercive force Hc* and the magnetic field amplitude $H_a$ (shown in FIG. 6 and FIG. 7, for example) and the second relationship of the relationship between the first ratio Ms/$\chi_H$* and the magnetic field amplitude $H_a$ (shown in FIG. 8 and FIG. 9, for example). This enables to recognize the forms of various lattice defects acting as causes of aged deterioration of strength, and to quantify the amounts of lattice defects.

In this way, by evaluating the relationship between the first ratio Ms/$\chi_H$* and pseudo coercive force Hc* and the first relationship and the second relationship of an austenitic stainless steel as an evaluation target which relationships are obtained in the measuring step, it becomes possible to more detailedly measure the kinds and amounts of lattice defects which act as causes of aged deterioration in austenitic stainless steel and which are important in evaluating the state of such aged deterioration.

In the evaluating method of the present invention, it is also possible, in the information obtaining step, to obtain the third relationship of the relationship between the first ratio Ms/$\chi_H$* and the pseudo coercive force Hc* as shown in FIG. 10 through FIG. 13 from the first relationship and the second relationship, and to evaluate the state of the aged deterioration in the austenitic stainless steel based on the third relationship in the evaluating step.

In this way, those relational diagrams (such as shown in FIG. 10 through FIG. 13) represented by these relationships are to show the forms and magnitudes of potential energies of domain wall movements, thereby allowing to more precisely and readily evaluate the aged deterioration in the austenitic stainless steel as the evaluation target, based on these relational diagrams.

Note, since both of the first ratio Ms/$\chi_H$* and the pseudo coercive force Hc* are magnetic quantities concerning characteristics of a material, the relationship represented by the first ratio Ms/$\chi_H$* and pseudo coercive force Hc* does not explicitly (directly) include external variables such as the magnetic field amplitude $H_a$, and includes only internal factors of the material. Thus, the relationship represented by the first ratio Ms/$\chi_H$* and pseudo coercive force Hc* is to give information of physical properties within the material inclusive of lattice defects, without depending on external variables.

In the evaluating method of the present invention, it is also possible to obtain the fourth relationship of the relationship between the first ratio Ms/$\chi_H$* and the applied stress σ (such as relational diagrams shown in FIG. 15 and FIG. 16) in the information obtaining step from the first relationship and the second relationship or from the third relationship, and to evaluate the state of aged deterioration of the austenitic stainless steel based on the fourth relationship in the evaluating step.

In this way, it becomes possible to quantitatively obtain the values of applied stress σ during a period of time from a state before aged deterioration to a state upon the crack initiation by measuring and obtaining the value of the first ratio $Ms/\chi_H^*$ of the evaluation target, thereby more precisely predicting an extent of progress of aged deterioration, an expected life and the like of the evaluation target. Further, it is possible to know the dislocation density from the value of applied stress σ, by the above-explained information obtaining step.

Incidentally, those physical quantities other than the pseudo coercive force Hc* depend on the amount of the martensitic phase. Further, the amount of the martensitic phase is proportional to the saturation magnetization Ms, and does not necessarily depend on the amount of lattice defects such as dislocation. Thus, to evaluate aged deterioration by adopting such physical quantities, it is necessary that the physical quantities other than the pseudo coercive force Hc* are normalized by the saturation magnetization Ms.

However, there are required magnetic field intensities H of $10^4$ [Oe] or more to directly obtain the saturation magnetization Ms due to martensitic phase as described above, and this is a difficult condition upon utilizing a nondestructive inspection.

Further, those physical quantities other than the pseudo coercive force Hc*, i.e., the $W_F^*$, $W_R^*$, Br*, Bm*, $\chi_r^*$, $\chi_H^*$, $\chi_b^*$, $\chi_a^*$ are proportional to the amount of the martensitic phase. By obtaining ratios among these physical quantities instead of normalizing these physical quantities by the saturation magnetization, it becomes possible to establish quantities independent of the amount of the martensitic phase. This will be concretely explained hereinafter.

Figure 17:
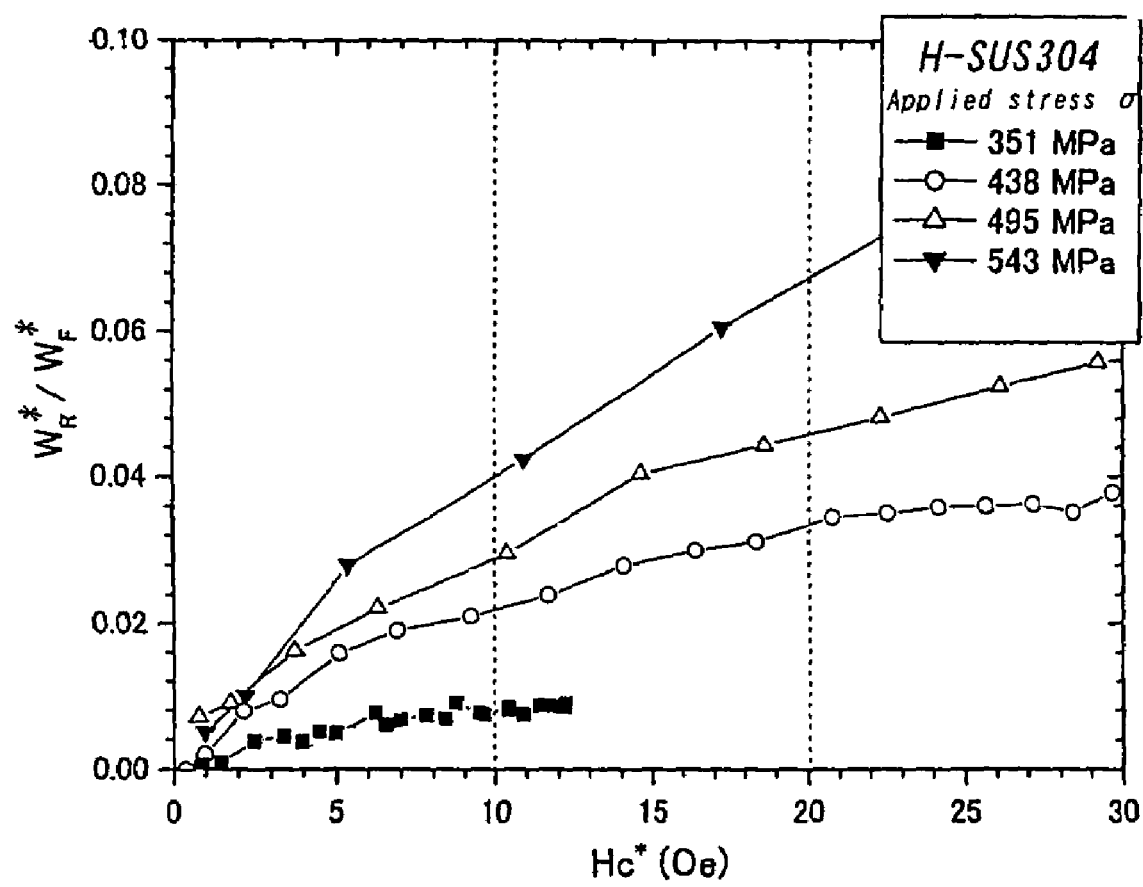
FIG. 17 is a relational diagram showing an applied-stress dependency of a relationship between the second ratio $W_R^*/W_F^*$ and the pseudo coercive force Hc* for austenitic stainless steel H-SUS304.
Figure 18:
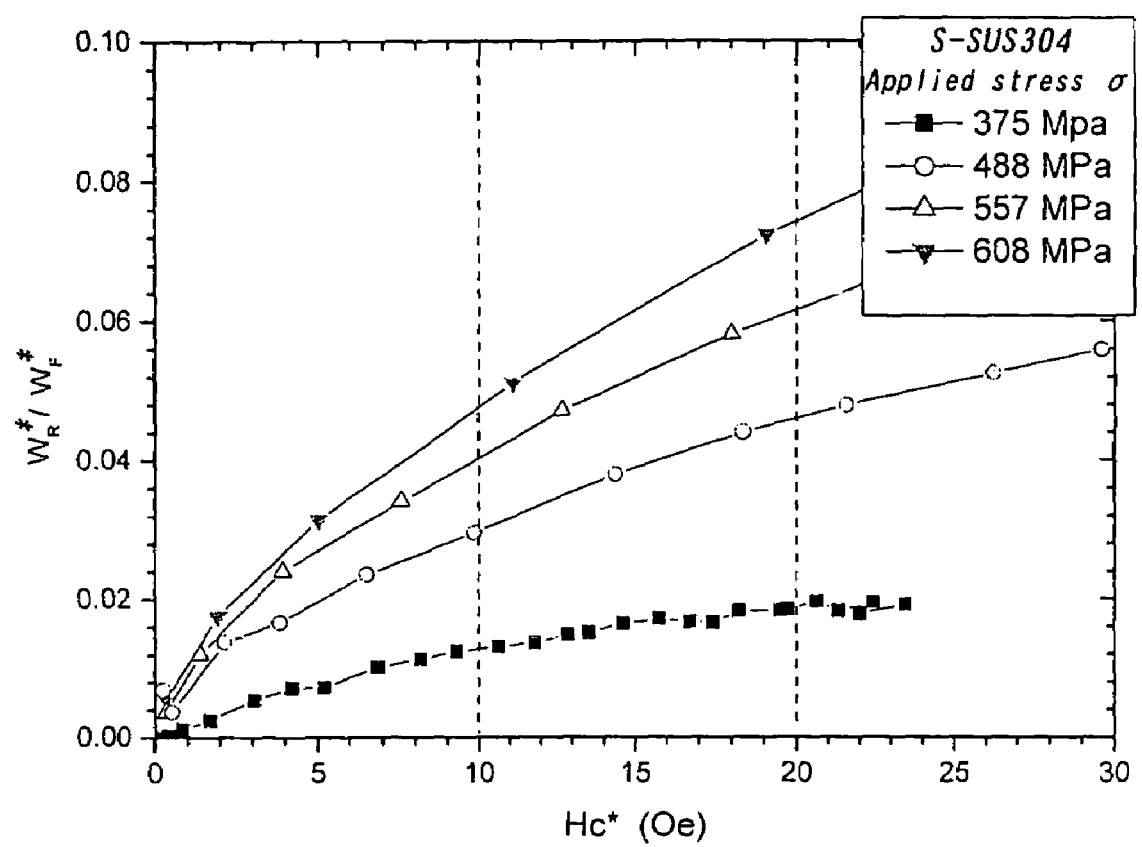
FIG. 18 is a relational diagram showing an applied-stress dependency of a relationship between the second ratio $W_R^*/W_F^*$ and the pseudo coercive force Hc* for austenitic stainless steel S-SUS304.
Figure 19:
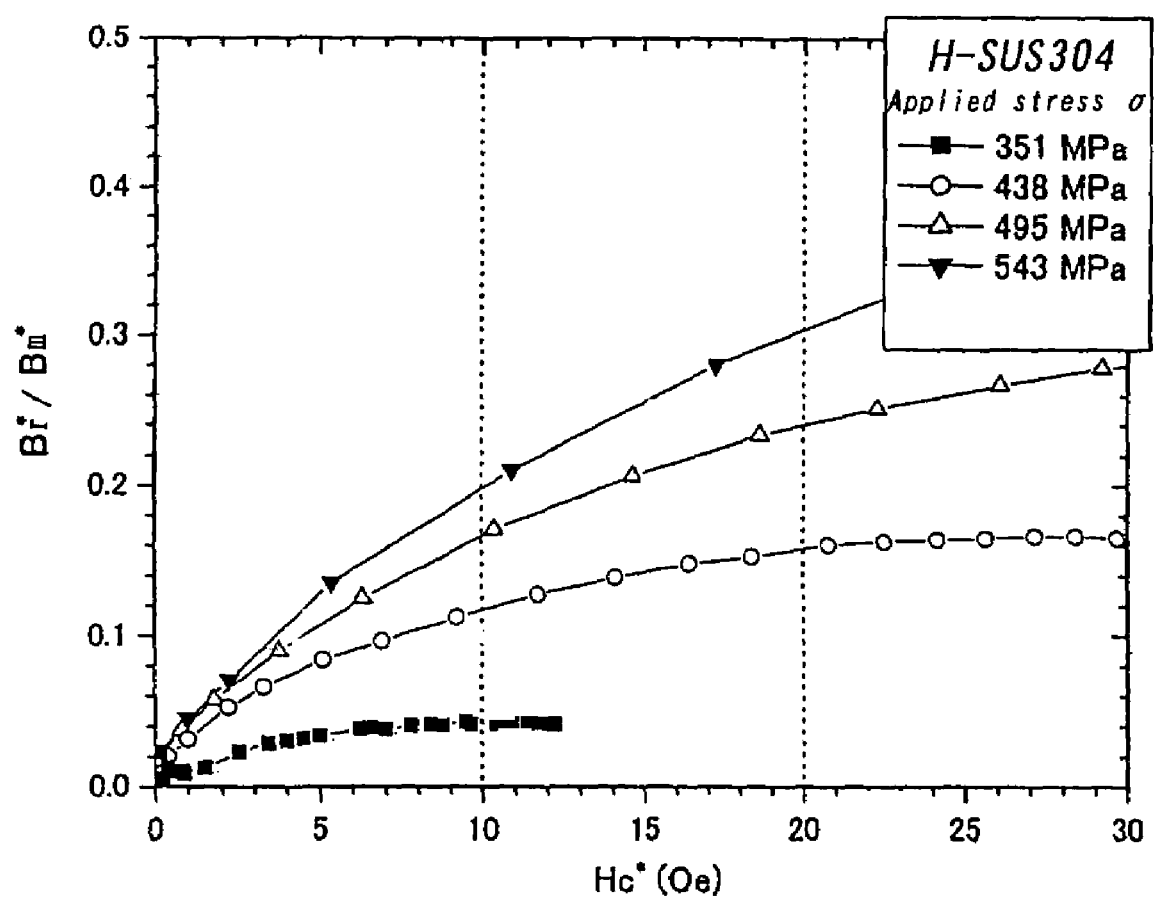
FIG. 19 is a relational diagram showing an applied-stress dependency of a relationship between the third ratio Br*/Bm* and the pseudo coercive force Hc* for austenitic stainless steel H-SUS304.
Figure 20:
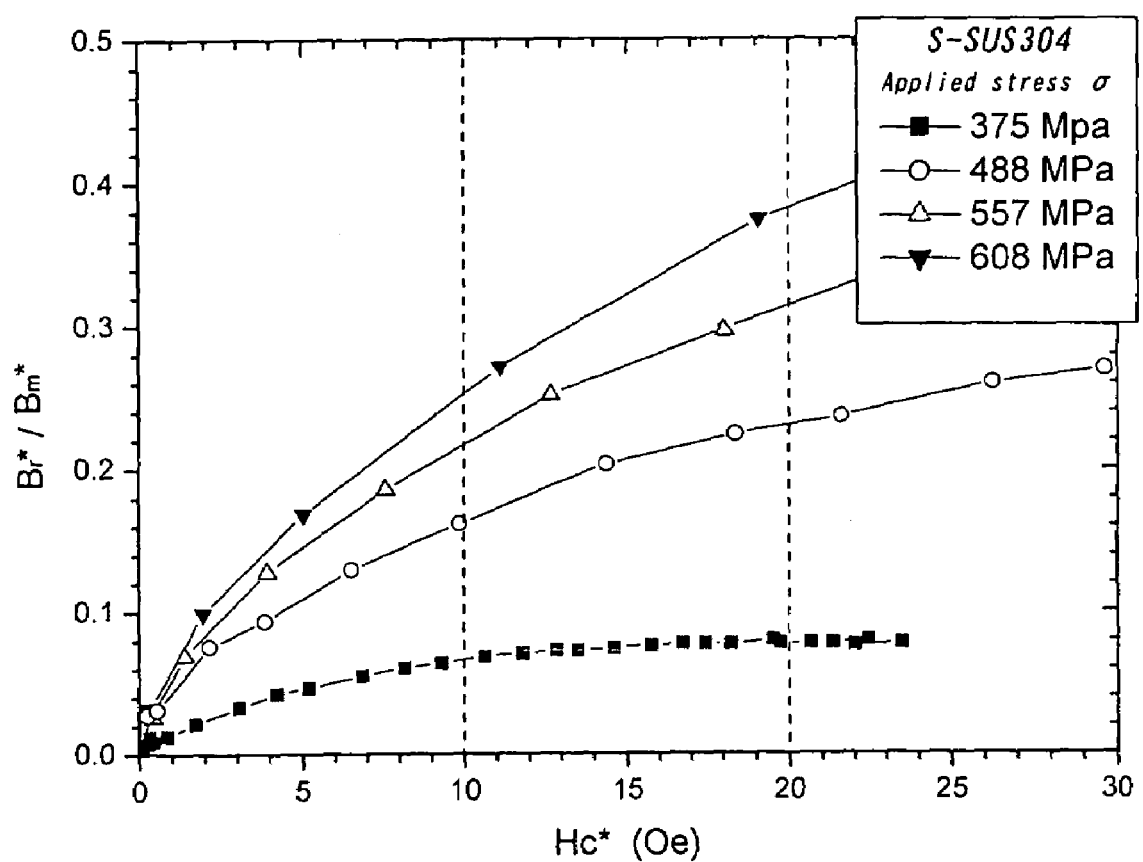
FIG. 20 is a relational diagram showing an applied-stress dependency of a relationship between the third ratio Br*/Bm* and the pseudo coercive force Hc* for austenitic stainless steel S-SUS304.

FIG. 17 and FIG. 18 show applied-stress dependencies concerning the fifth relationship of the correlation between the second ratio $W_R^*/W_F^*$ and the pseudo coercive force Hc*, in H-SUS304 and S-SUS304 respectively, and FIG. 19 and FIG. 20 show applied-stress dependencies concerning the sixth relationship of the correlation between the pseudo coercive force Hc* and the third ratio Br*/Bm*, in H-SUS304 and S-SUS304 respectively.

Figure 21:
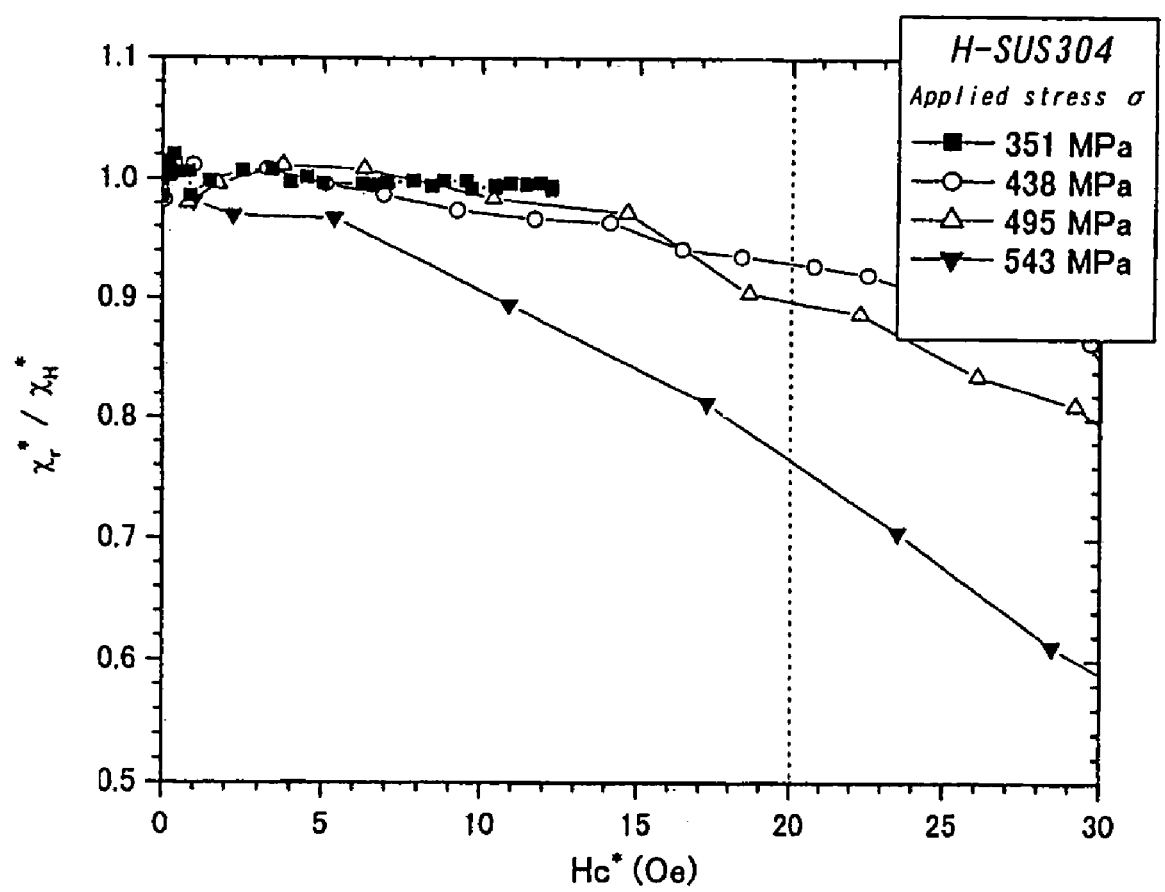
FIG. 21 is a relational diagram showing an applied-stress dependency of a relationship between the fourth ratio $\chi_r^*/\chi_H^*$ and the pseudo coercive force Hc* for austenitic stainless steel H-SUS304.
Figure 22:
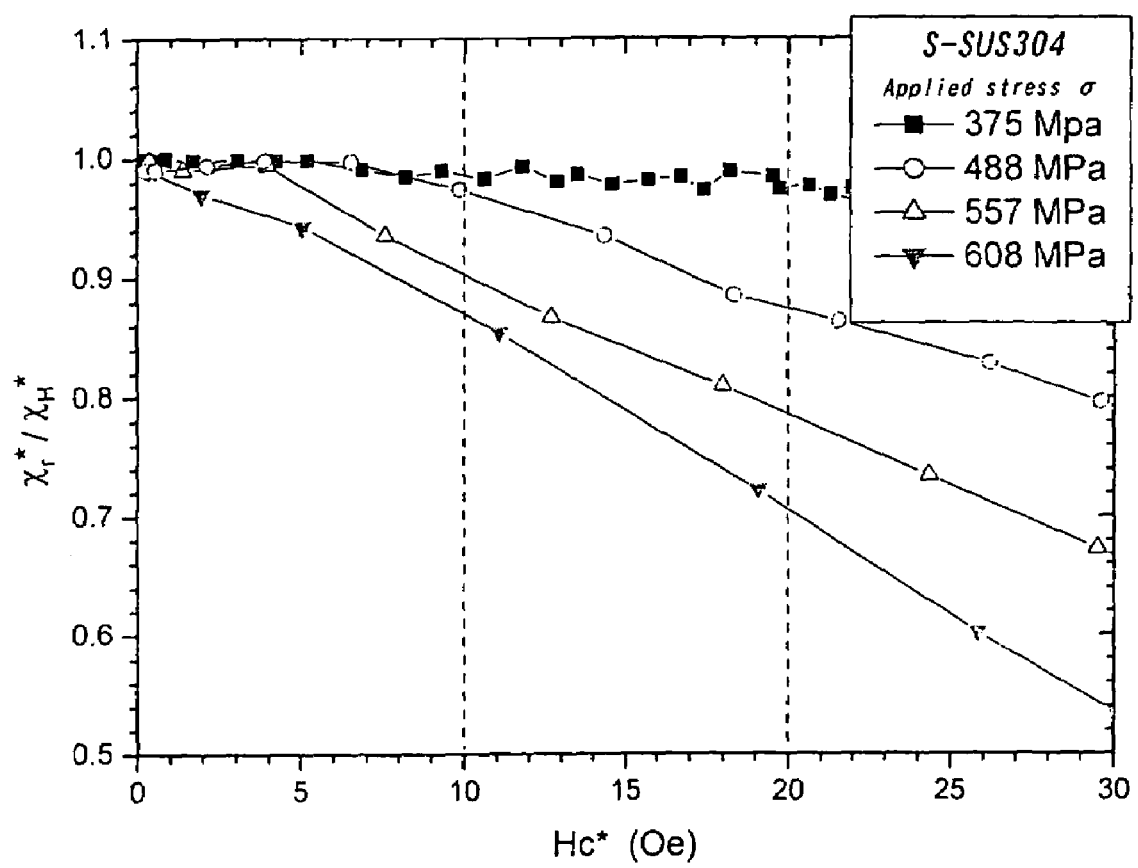
FIG. 22 is a relational diagram showing an applied-stress dependency of a relationship between the fourth ratio $\chi_r^*/\chi_H^*$ and the pseudo coercive force Hc* for austenitic stainless steel S-SUS304.
Figure 23:
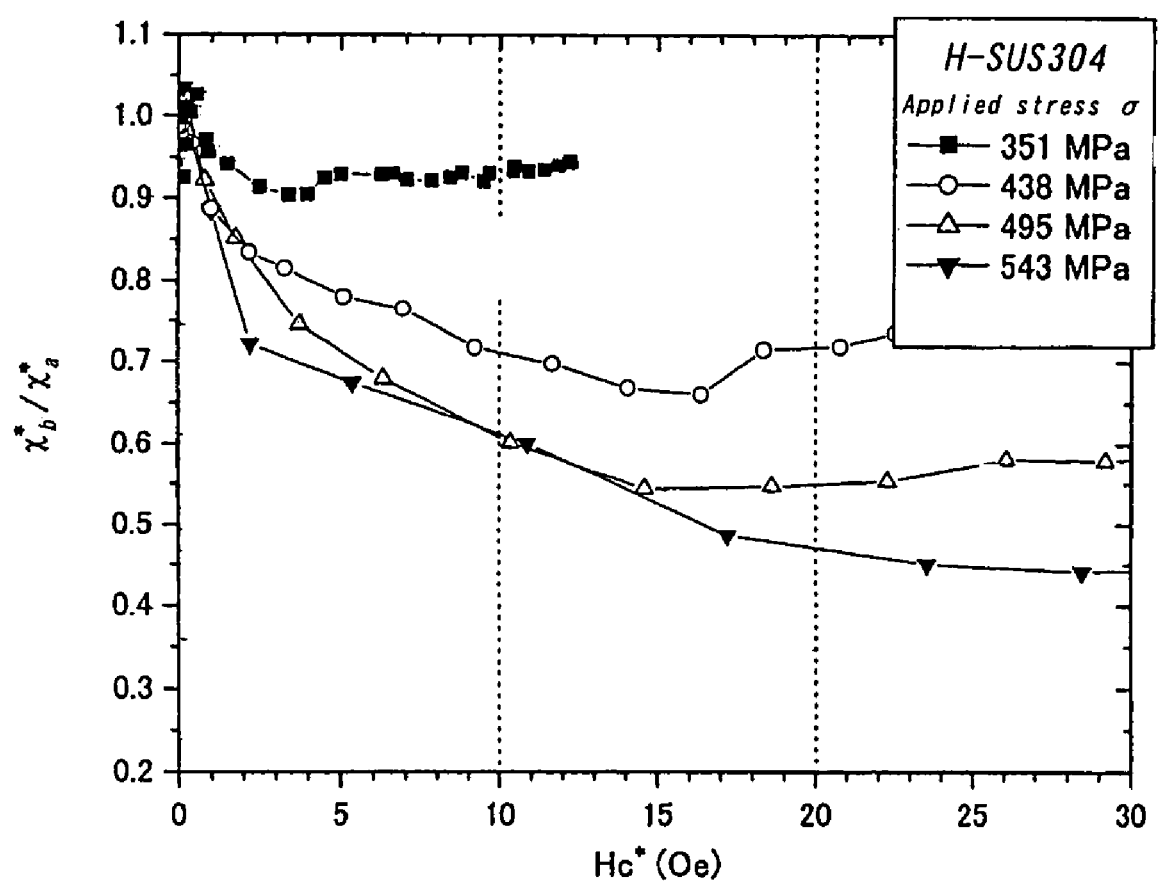
FIG. 23 is a relational diagram showing an applied-stress dependency of a relationship between the fifth ratio $\chi_b^*/\chi_a^*$ and the pseudo coercive force Hc* for austenitic stainless steel H-SUS304.
Figure 24:
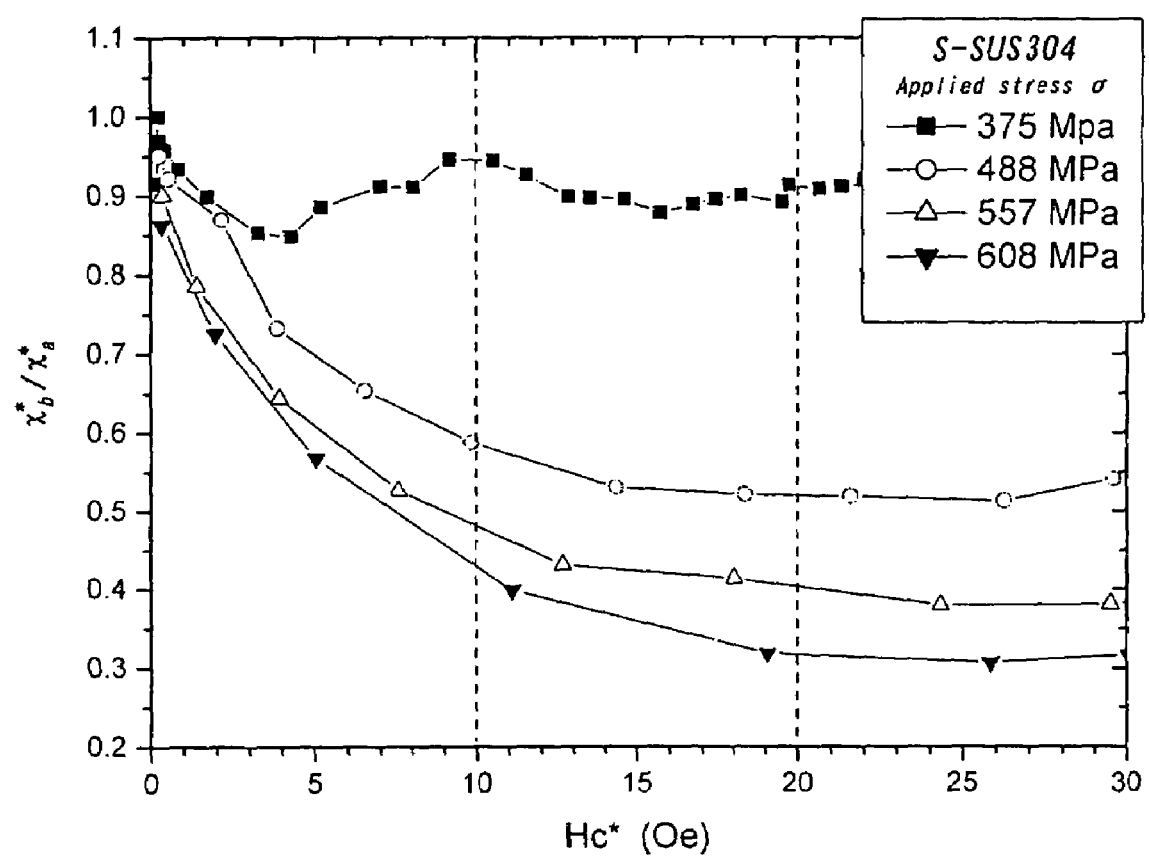
FIG. 24 is a relational diagram showing an applied-stress dependency of a relationship between the fifth ratio $\chi_b^*/\chi_a^*$ and the pseudo coercive force Hc* for austenitic stainless steel S-SUS304.

Further, FIG. 21 and FIG. 22 show applied-stress dependencies concerning the seventh relationship of the correlation between the fourth ratio $\chi_r^*/\chi_H^*$ and the pseudo coercive force Hc*, in H-SUS304 and S-SUS304 respectively, and FIG. 23 and FIG. 24 show applied-stress dependencies concerning the eighth relationship of the correlation between the fifth ratio $\chi_b^*/\chi_a^*$ and the pseudo coercive force Hc*, in H-SUS304 and S-SUS304 respectively.

As shown in FIG. 17 through FIG. 24, it is understood that each of the fifth relationship of the correlation between the second ratio $W_R^*/W_F^*$ and the pseudo coercive force Hc*, the sixth relationship of the correlation between the pseudo coercive force Hc* and the third ratio Br*/Bm*, the seventh relationship of the correlation between the fourth ratio $\chi_r^*/\chi_H^*$ and the pseudo coercive force Hc*, and the eighth relationship of the correlation between the fifth ratio $\chi_b^*/\chi_a^*$ and the pseudo coercive force Hc*, is sensitive to the applied stress σ, and the aged deterioration of austenitic stainless steel can be evaluated based on these correlations.

Moreover, the ratios of physical quantities such as the second ratio $W_R^*/W_F^*$, the third ratio Br*/Bm*, the fourth ratio $\chi_r^*/\chi_H^*$ and the fifth ratio $\chi_b^*/\chi_a^*$ do not depend on the amount of the martensitic phase. Thus, there are not required magnetic field intensities H of $10^4$ [Oe] or more for directly obtaining the saturation magnetization Ms due to the martensitic phase, so that any difficulty is not caused upon conducting a nondestructive inspection even without relying on the above-mentioned expedient method.

Further, as understood from the fifth relationship of the relationship between the second ratio $W_R^*/W_F^*$ and the pseudo coercive force Hc*, the sixth relationship of the relationship between the third ratio Br*/Bm* and the pseudo coercive force Hc*, the seventh relationship of the relationship between the fourth ratio $\chi_r^*/\chi_H^*$ and the pseudo coercive force Hc*, and the eighth relationship of the relationship between the fifth ratio $\chi_b^*/\chi_a^*$ and the pseudo coercive force Hc* shown in FIG. 17 through FIG. 24, respectively, the aged deterioration can be evaluated as shown hereinafter even without obtaining the whole of relational diagrams by measurement.

Figure 25:
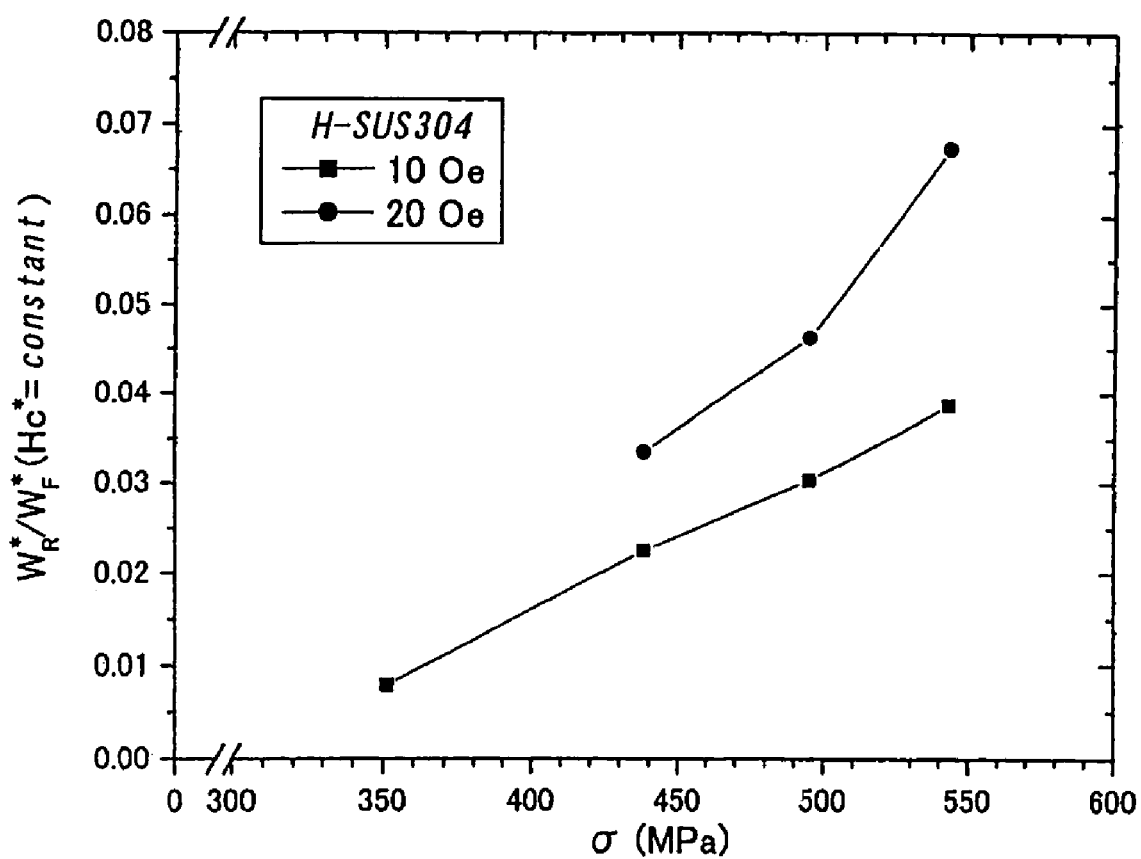
FIG. 25 is a relational diagram showing a relationship between the second ratio $W_R^*/W_F^*$ and the applied stress σ at the pseudo coercive forces Hc*=10 and 20 [Oe] for austenitic stainless steel H-SUS304.
Figure 26:
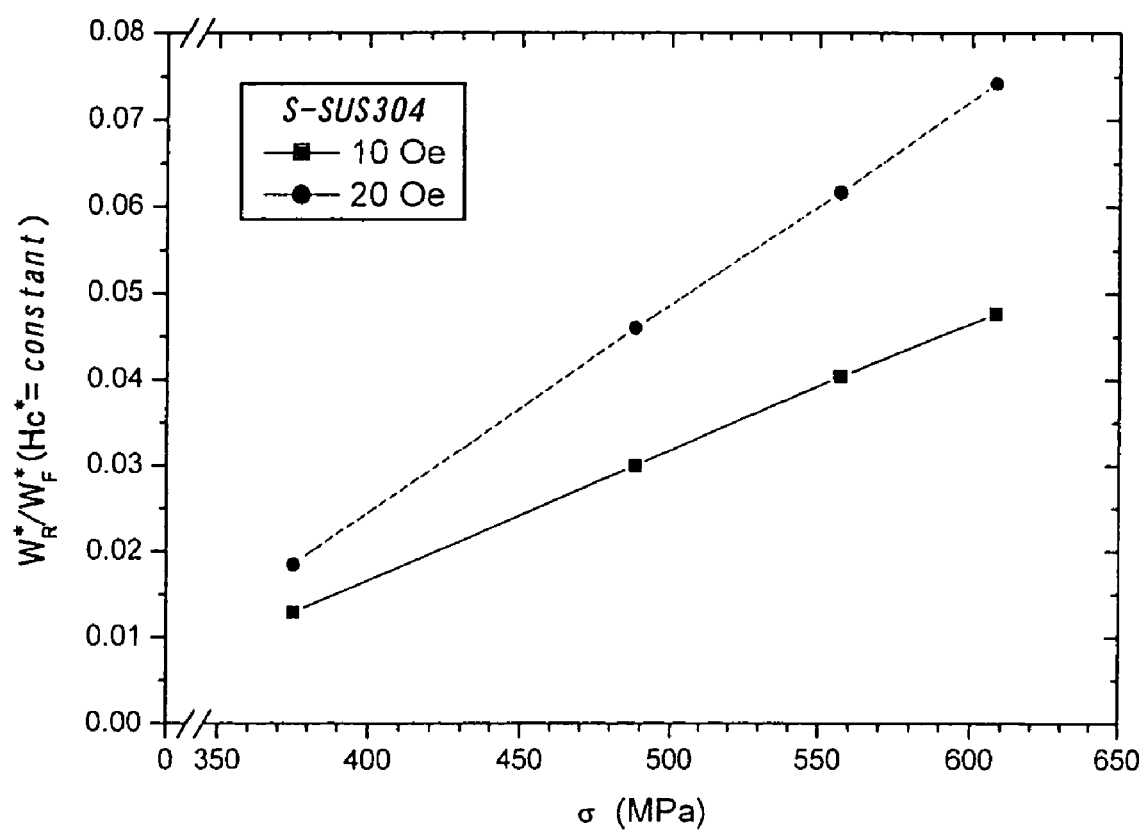
FIG. 26 is a relational diagram showing a relationship between the second ratio $W_R^*/W_F^*$ and the applied stress σ at the pseudo coercive forces Hc*=10 and 20 [Oe] for austenitic stainless steel S-SUS304.
Figure 27:
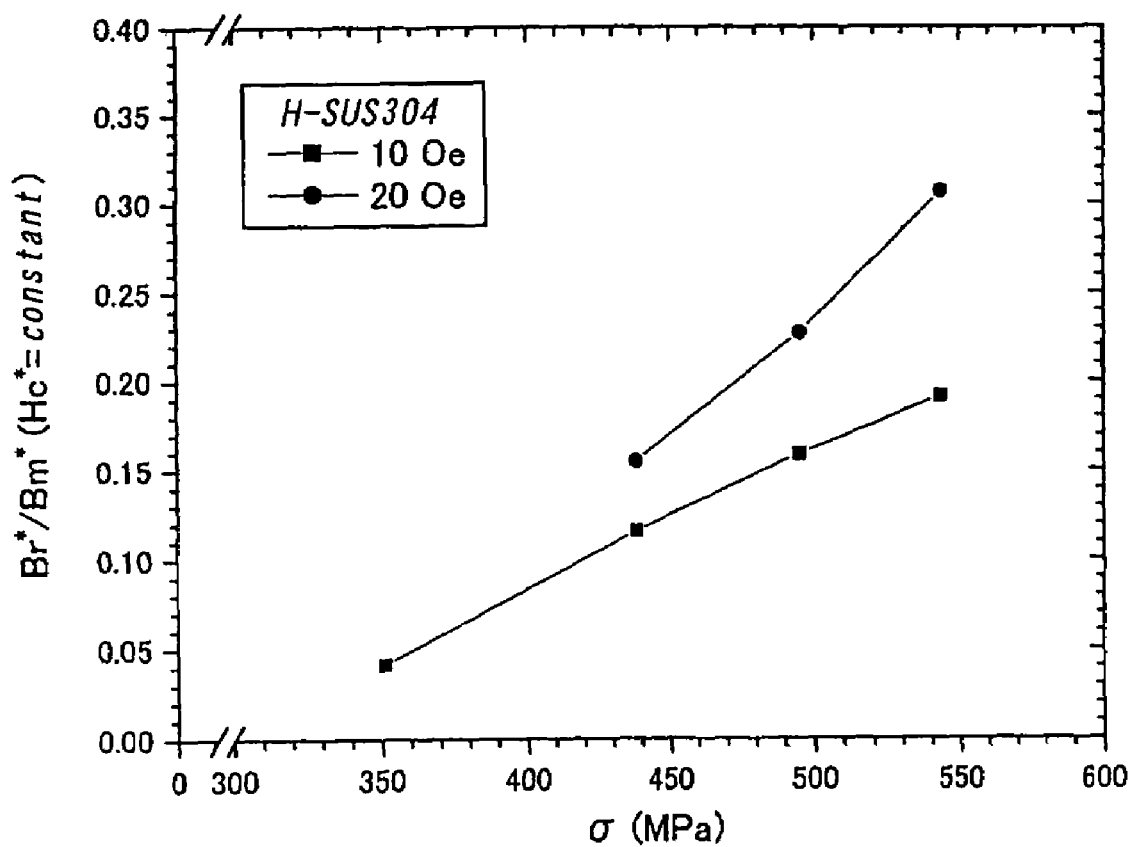
FIG. 27 is a relational diagram showing a relationship between the third ratio Br*/Bm* and the applied stress σ at the pseudo coercive forces Hc*=10 and 20 [Oe] for austenitic stainless steel H-SUS304.
Figure 28:
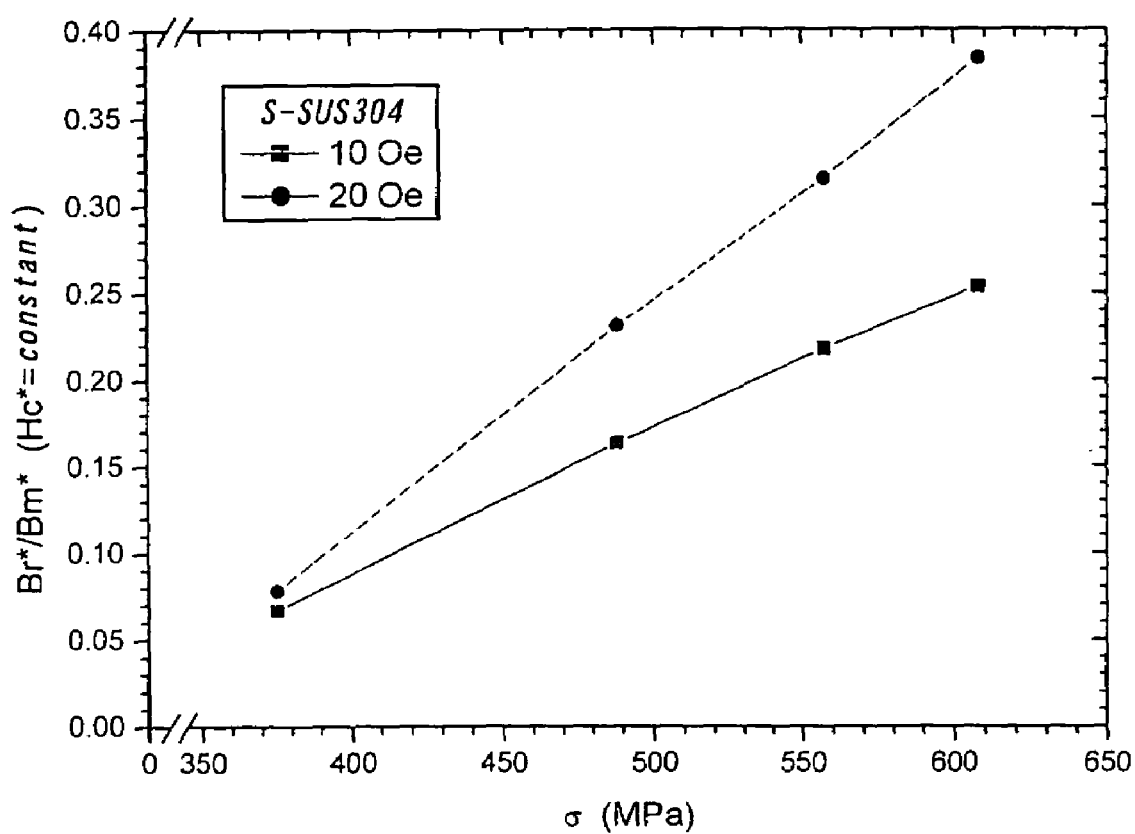
FIG. 28 is a relational diagram showing a relationship between the third ratio Br*/Bm* and the applied stress σ at the pseudo coercive forces Hc*=10 and 20 [Oe] for austenitic stainless steel S-SUS304.
Figure 29:
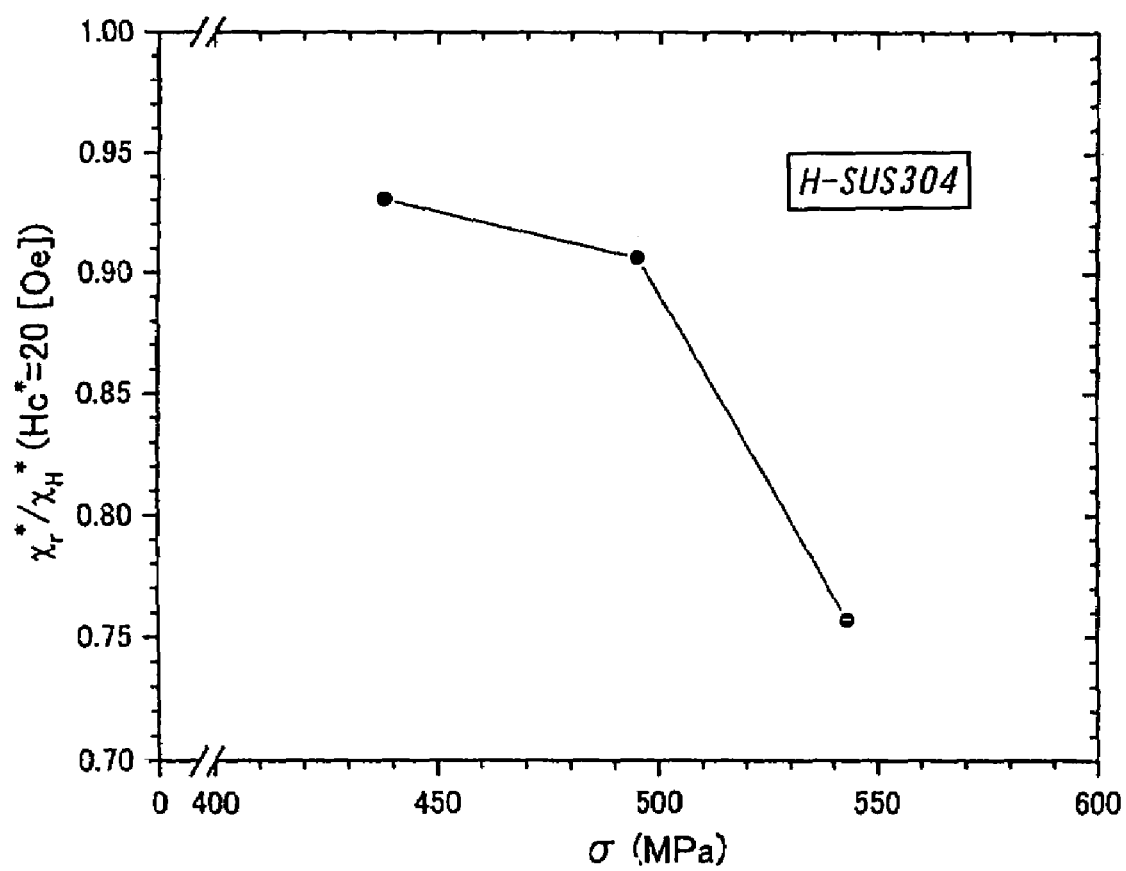
FIG. 29 is a relational diagram showing a relationship between the fourth ratio $\chi_r^*/\chi_H^*$ and the applied stress σ at the pseudo coercive force Hc*=20 [Oe] for austenitic stainless steel H-SUS304.
Figure 30:
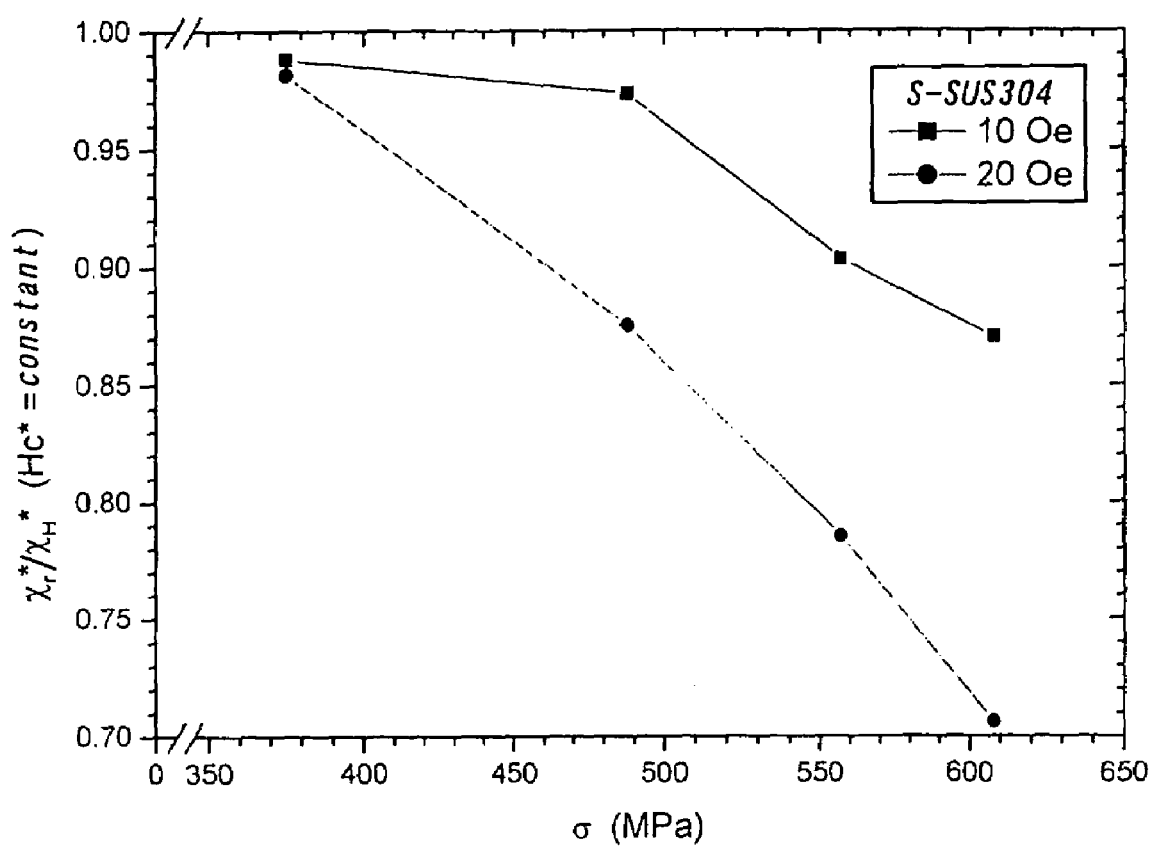
FIG. 30 is a relational diagram showing a relationship between the fourth ratio $\chi_r^*/\chi_H^*$ and the applied stress σ at the pseudo coercive forces Hc*=10 and 20 [Oe] for austenitic stainless steel S-SUS304.

Namely, each of FIG. 25 and FIG. 26 shows the ninth relationship of the relationship between the second ratio $W_R^*/W_F^*$ and the applied stress σ where the pseudo coercive force Hc*=constant. Each of FIG. 27 and FIG. 28 shows the tenth relationship of the relationship between the third ratio Br*/Bm* and the applied stress σ where the pseudo coercive force Hc*=constant. Each of FIG. 29 and FIG. 30 shows the eleventh relationship of the relationship between the fourth ratio $\chi_r^*/\chi_H^*$ and the applied stress σ where the pseudo coercive force Hc*=constant. Each of FIG. 31 and FIG. 32 shows the twelfth relationship of the relationship between the fifth ratio $\chi_b^*/\chi_a^*$ and the applied stress σ where the pseudo coercive force Hc*=constant.

Concerning FIG. 25 and FIG. 26, it is possible to know the state of aged deterioration of an austenitic stainless steel as an evaluation target based on the relational diagram where the pseudo coercive force Hc*=10 or 20 [Oe], such as by comparing the value of the second ratio $W_R^*/W_F^*$ at the applied stress σ (σ=543 [MPa] in FIG. 25, and σ=608 [MPa] in FIG. 26) just before the breaking, with the value of the second ratio $W_R^*/W_F^*$ obtained by measurement of the evaluation target.

Figure 31:
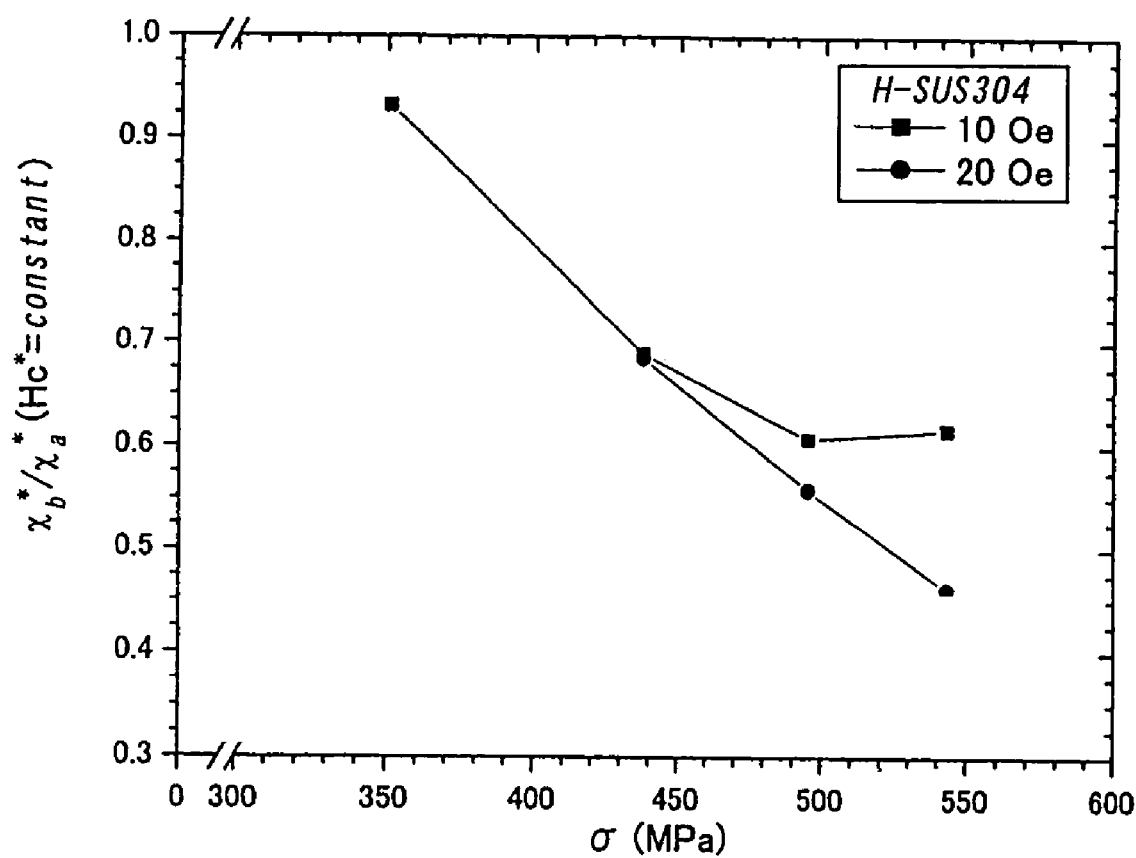
FIG. 31 is a relational diagram showing a relationship between the fifth ratio $\chi_b^*/\chi_a^*$ and the applied stress σ at the pseudo coercive forces Hc*=10 and 20 [Oe] for austenitic stainless steel H-SUS304.
Figure 32:
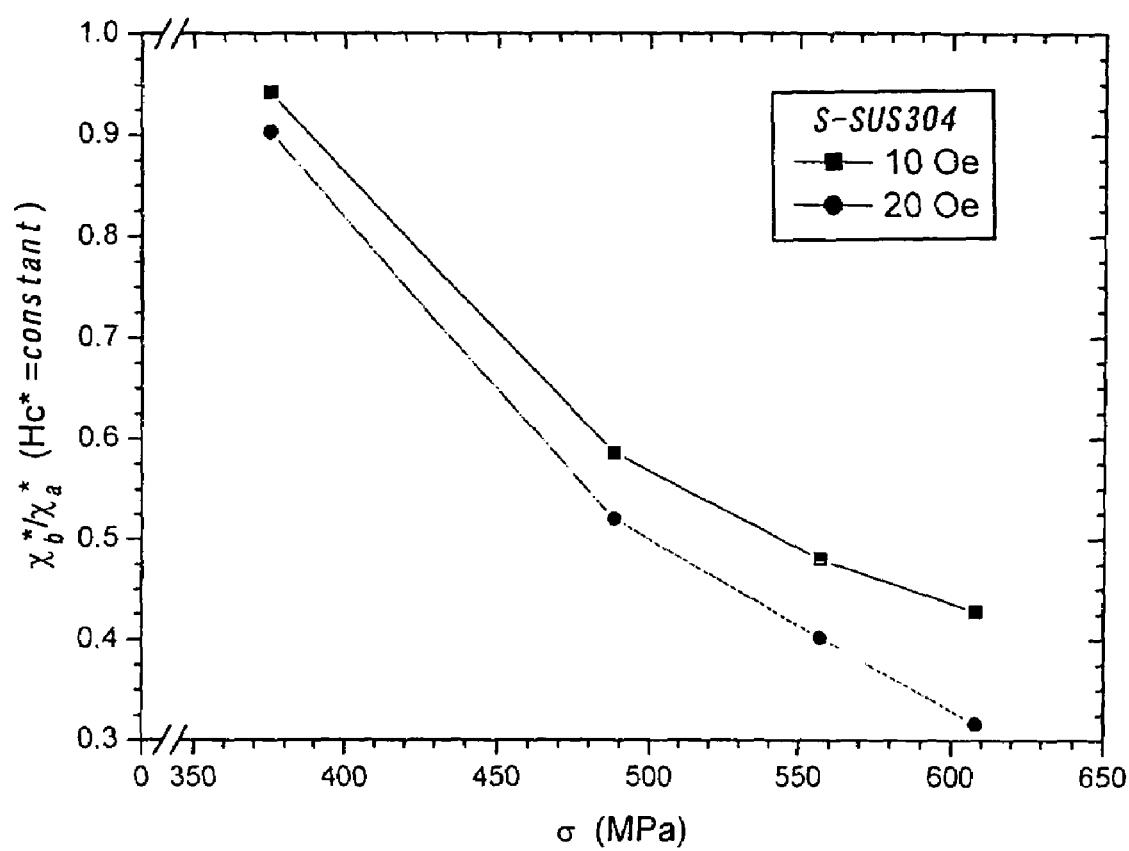
FIG. 32 is a relational diagram showing a relationship between the fifth ratio $\chi_b^*/\chi_a^*$ and the applied stress σ at the pseudo coercive forces Hc*=10 and 20 [Oe] for austenitic stainless steel S-SUS304.

Similarly to the second ratio $W_R^*/W_F^*$, it is also possible to know the state of aged deterioration of an austenitic stainless steel, by mutually comparing the values of the third ratio Br*/Bm* based on the relational diagrams shown in FIG. 27 and FIG. 28, the values of the fourth ratio $\chi_r^*/\chi_H^*$ based on the relational diagrams shown in FIG. 29 and FIG. 30, or the values of the fifth ratio $\chi_b^*/\chi_a^*$ based on the relational diagrams shown in FIG. 31 and FIG. 32.

Based on the above and similarly to the previously explained first ratio $Ms/\chi_H^*$, it has become apparent from the study of the present inventor that the correlation between the pseudo coercive force Hc* and the second ratio $W_R^*/W_F^*$, the correlation between the pseudo coercive force Hc* and the third ratio Br*/Bm*, the correlation between the pseudo coercive force Hc* and the fourth ratio $\chi_r^*/\chi_H^*$, and the correlation between the pseudo coercive force Hc* and the fifth ratio $\chi_b^*/\chi_a^*$ have intimate correlations with the internal factor (internal stress) which transforms the austenite phase to the martensitic phase, because the above applied stress σ can be substituted for the internal factor.

Further, the correlation between the second ratio $W_R^*/W_F^*$ and the pseudo coercive force Hc*, the correlation between the third ratio Br*/Bm* and the pseudo coercive force Hc*, the correlation between the pseudo coercive force Hc* and the fourth ratio $\chi_r^*/\chi_H^*$, and the correlation between the pseudo coercive force Hc* and the fifth ratio $\chi_b^*/\chi_a^*$ are different depending on the chemical compositions of materials, thereby making it possible to identify the kind of materials based on such correlations.

Moreover, as described above, the dislocation density is increased by a progressed metal fatigue within the martensitic phase introduced by plastic deformation of austenitic stainless steel, so that domain walls within the martensitic phase are difficult to move by the increased dislocation density. Then, all of the physical quantities to be obtained by analyzing minor hysteresis loops are quantities related to domain wall movements, thereby making it possible to obtain information of an extent of metal fatigue such as the dislocation density from these physical quantities.

Here, the pseudo hysteresis loss $W_F^*$, which is an area of portion surrounded by the minor hysteresis loop, represents an amount of "work" which has been transformed into thermal energy when domain wall movements are irreversibly caused, and the pseudo hysteresis loss $W_F^*$ is a quantity related to dislocations acting as an obstacle against domain wall movements similarly to the previous first ratio $Ms/\chi_H^*$.

Further, the pseudo remanence work $W_R^*$, which is an area of the portion where the magnetic flux density B>0 and the magnetic field intensity H<0 within the area of the portion surrounded by the minor hysteresis loop, represents an amount of "work" which has been transformed into thermal energy when domain walls have moved in the region of the magnetic field intensity H from zero to the pseudo coercive force Hc*.

Therefore, the whole image of the potential energy of domain wall movements can be grasped, based on the correlation obtained by the value of the second ratio $W_R^*/W_F^*$ by changing the magnetic field amplitude $H_a$.

Further, the pseudo remanence Br* represents a remnant magnetization caused by stoppage of domain walls by obstacles when the magnetic field intensity H is zero where the domain walls move within the magnetic field amplitude $H_a$, and the reciprocal of pseudo remanence susceptibility $1/\chi_r^*$ represents a force which stops the domain walls at that pseudo remanence Br*.

Moreover, the former $\chi_b^*$ of the two susceptibilities $\chi_b^*$ and $\chi_a^*$ at the magnetic field amplitude $H_a$ is called "reversible susceptibility" and represents a susceptibility where the magnetic field is decreased, and the latter $\chi_a^*$ represents a susceptibility where the magnetic field is increased. These reciprocal susceptibilities $1/\chi_b^*$ and $1/\chi_a^*$ represent forces exerted on the domain walls near the magnetic field amplitude $H_a$, such that the pseudo susceptibility $\chi_a^*$ corresponds to a force for strengthening the magnetic field intensity H and the reciprocal of pseudo susceptibility $1/\chi_b^*$ corresponds to a force for weakening the magnetic field intensity H.

Thus, in the information obtaining step, there is obtained at least one of the fifth relationship of the relationship between the second ratio $W_R^*/W_F^*$ and the pseudo coercive force Hc* (see FIG. 17 and FIG. 18), the sixth relationship of the relationship between the third ratio Br*/Bm* and the pseudo coercive force Hc* (see FIG. 19 and FIG. 20), the seventh relationship of the relationship between the fourth ratio $\chi_r^*/\chi_H^*$ and the pseudo coercive force Hc* (see FIG. 21 and FIG. 22) and the eighth relationship of the relationship between the fifth ratio $\chi_b^*/\chi_a^*$ and the pseudo coercive force Hc* (see FIG. 23 and FIG. 24).

Then, based on the correlations obtained in the information obtaining step, to be obtained as measured values of physical quantities at the measuring step are: the value of pseudo coercive force Hc*; and the values of the each physical quantity of the second ratio $W_R^*/W_F^*$, the third ratio Br*/Bm*, the fourth ratio $\chi_r^*/\chi_H^*$ and the fifth ratio $\chi_b^*/\chi_a^*$, which are used for the correlation between physical quantities obtained in the information obtaining step.

Then, the aged deterioration in the austenitic stainless steel as an evaluation target is evaluated from the measured values of physical quantities obtained in the measuring step and based on the correlation between physical quantities obtained in the information obtaining step, thereby making it possible to obtain magnitudes of forces exerted on domain walls in the martensitic phase as well as the distribution of the magnitudes. This enables to recognize the forms of various lattice defects acting as causes of aged deterioration, and to quantify the amounts of lattice defects.

Thus, according to such an evaluating method, it is possible, based on the relational diagram of the correlation between the physical quantities, to more detailedly measure the kinds and amounts of lattice defects which act as causes of aged deterioration in an austenitic stainless steel structural material, as the state of aged deterioration of the structural material, thereby allowing to precisely and thoroughly evaluate the aged deterioration of the material in a more detailed manner.

Note, all of the pseudo coercive force Hc*, the pseudo hysteresis loss $W_F^*$, the pseudo remanence work $W_R^*$, the pseudo susceptibility $\chi_H^*$ at the pseudo coercive force Hc*, the pseudo remanence Br*, the pseudo remanence susceptibility $\chi_r^*$ at the pseudo remanence Br*, the pseudo susceptibility $\chi_H^*$ at the pseudo coercive force Hc*, and the two susceptibilities $\chi_b^*$ and $\chi_a^*$ at the magnetic field amplitude $H_a$ are magnetic quantities concerning characteristics of a material.

Thus, the relationships represented by these physical quantities do not explicitly include external variables such as the magnetic field amplitude $H_a$, and include only internal factors of the material. Therefore, the relationships represented by the physical quantities are to give information of physical properties within the material inclusive of lattice defects, without depending on external variables.

Further, based on the evaluating method and on at least one of the correlations of the fifth relationship, the sixth relationship, the seventh relationship and the eighth relationship, there is obtained at least one of the following relationships, the ninth relationship of the relationship between the second ratio $W_R^*/W_F^*$ and the applied stress σ at a certain constant pseudo coercive force Hc*, the tenth relationship of the relationship between the third ratio Br*/Bm* and the applied stress σ at a certain constant pseudo coercive force Hc*, the eleventh relationship of the relationship between the fourth ratio $\chi_r^*/\chi_H^*$ and the applied stress σ at a certain constant pseudo coercive force Hc*, and the twelfth relationship of the relationship between the fifth ratio $\chi_b^*/\chi_a^*$ and the applied stress σ at a certain constant pseudo coercive force Hc*, as shown in FIG. 25 through FIG. 32, respectively.

In the evaluating step thereafter, it is possible to evaluate the aged deterioration in the austenitic stainless steel based on the relationship obtained in the information obtaining step.

In this way, it becomes possible to quantitatively obtain the values of applied stress σ during a period of time from a state before aged deterioration to a state upon the crack initiation by measuring and obtaining the values of the second ratio $W_R^*/W_F^*$, the third ratio Br*/Bm*, the fourth ratio $\chi_r^*/\chi_H^*$ and the fifth ratio $\chi_b^*/\chi_a^*$ of the evaluation target in the measuring step, thereby more precisely predicting an extent of progress of aged deterioration, an expected life and the like of the evaluation target. Further, it is possible to know the change of the dislocation density from the value of applied stress σ, by the above-explained information obtaining step.

Additionally, all of the pseudo coercive force Hc*, the pseudo hysteresis loss $W_F^*$, the pseudo remanence work $W_R^*$, the pseudo susceptibility $\chi_H^*$ at the pseudo coercive force Hc*, the pseudo remanence Br*, the pseudo remanence susceptibility $\chi_r{}^*$ at the pseudo remanence Br*, the pseudo susceptibility $\chi_H{}^*$ at the pseudo coercive force Hc*, and the two susceptibilities $\chi_b{}^*$ and $\chi_a{}^*$ at the magnetic field amplitude $H_a$ are physical quantities sensitive to lattice defects such as dislocations, and all of these physical quantities can be obtained from the minor hysteresis loop by the measurement.

Simultaneously, although these physical quantities also depend on the amount of the martensitic phase, the effects concerning the amount of the martensitic phase can be removed by obtaining ratios among these physical quantities.

Thus, contrary to that the conventionally and typically conducted major hysteresis loop requires to apply a magnetic field from the exterior until the magnetization is perfectly saturated, it is unnecessary to apply a magnetic field from the exterior until the magnetization is perfectly saturated in the measurement to be conducted in accordance with the nondestructive evaluating method for aged deterioration in austenitic stainless steel of the present invention, thereby allowing to obtain the minor hysteresis loop with a lower external magnetic field.

Also from a standpoint of constitution of a measuring apparatus, the evaluating method of the present invention for conducting the minor hysteresis loop test is capable of constituting the measuring apparatus in a more simple manner and thus more advantageous, than the conventional typical evaluating method for conducting a major hysteresis loop test.

Note, to obtain the major hysteresis loop, there is applied a magnetic field from the exterior until the magnetization is perfectly saturated, so that the physical quantities to be obtained thereby are quantities independent of an external magnetic field. Contrary, the evaluating method of the present invention is to obtain a minor hysteresis loop which varies with a change of strength of an external magnetic field.

Thus, those physical quantities (the pseudo coercive force Hc*, the pseudo hysteresis loss $W_F{}^*$, the pseudo remanence work $W_R{}^*$, the pseudo susceptibility $\chi_H{}^*$ at the pseudo coercive force Hc*, the pseudo remanence Br*, the pseudo remanence susceptibility $\chi_r{}^*$ at the pseudo remanence Br*, the pseudo susceptibility $\chi_H{}^*$ at the pseudo coercive force Hc*, and the two susceptibilities $\chi_b{}^*$ and $\chi_a{}^*$ at the magnetic field amplitude $H_a$) obtained from the minor hysteresis loop are varied depending on an external magnetic field.

Therefore, it is necessary to precisely obtain the value of an internal magnetic field upon measuring the minor hysteresis loop, taking account of effects of diamagnetic field, leakage field and the like.

However, the fifth relationship of the relationship between the second ratio $W_R{}^*/W_F{}^*$ and the pseudo coercive force Hc* (see FIG. 17 and FIG. 18), the sixth relationship of the relationship between the third ratio Br*/Bm* and the pseudo coercive force Hc* (see FIG. 19 and FIG. 20), the seventh relationship of the relationship between the fourth ratio $\chi_r{}^*/\chi_H{}^*$ and the pseudo coercive force Hc* (see FIG. 21 and FIG. 22) and the eighth relationship of the relationship between the fifth ratio $\chi_b{}^*/\chi_a{}^*$ and the pseudo coercive force Hc* (see FIG. 23 and FIG. 24), all of which are the correlations among the physical quantities, do not directly include the strength H of the exterior magnetic field and the magnetic field amplitude $H_a$ as described above and are specific to the material. Thus, there is not necessarily required a value of an internal magnetic field upon application of the present invention to the nondestructive inspection.

The saturation magnetization, coercive force, remanent flux density and susceptibility to be obtained from the conventional major hysteresis loop largely depend on the amount and shape of the martensitic phase, thereby making it impossible to extract an information concerning lattice defects within the material.

Contrary, it has been found from the study by the present inventor that the evaluating method of the present invention utilizing the fifth relationship of the relationship between the second ratio $W_R{}^*/W_F{}^*$ and the pseudo coercive force Hc*, the sixth relationship of the relationship between the third ratio Br*/Bm* and the pseudo coercive force Hc*, the seventh relationship of the relationship between the fourth ratio $\chi_r{}^*/\chi_H{}^*$ and the pseudo coercive force Hc*, and the eighth relationship of the relationship between the fifth ratio $\chi_b{}^*/\chi_a{}^*$ and the pseudo coercive force Hc*, is superior in information quality, sensitivity, precision and the like, to a conventional evaluating method for mutually comparing values of saturation magnetization and the like.

In this way, the fifth relationship of the relationship between the second ratio $W_R{}^*/W_F{}^*$ and the pseudo coercive force Hc*, the sixth relationship of the relationship between the third ratio Br*/Bm* and the pseudo coercive force Hc*, the seventh relationship of the relationship between the fourth ratio $\chi_r{}^*/\chi_H{}^*$ and the pseudo coercive force Hc*, and the eighth relationship of the relationship between the fifth ratio $\chi_b{}^*/\chi_a{}^*$ and the pseudo coercive force Hc* do not require the value of the saturation magnetization Ms, thereby excluding difficulty upon conducting the nondestructive inspection, as previously explained, even without relying on the expedient method as explained in the first ratio $Ms/\chi_H{}^*$.

Embodiments of the Invention

Figure 33:
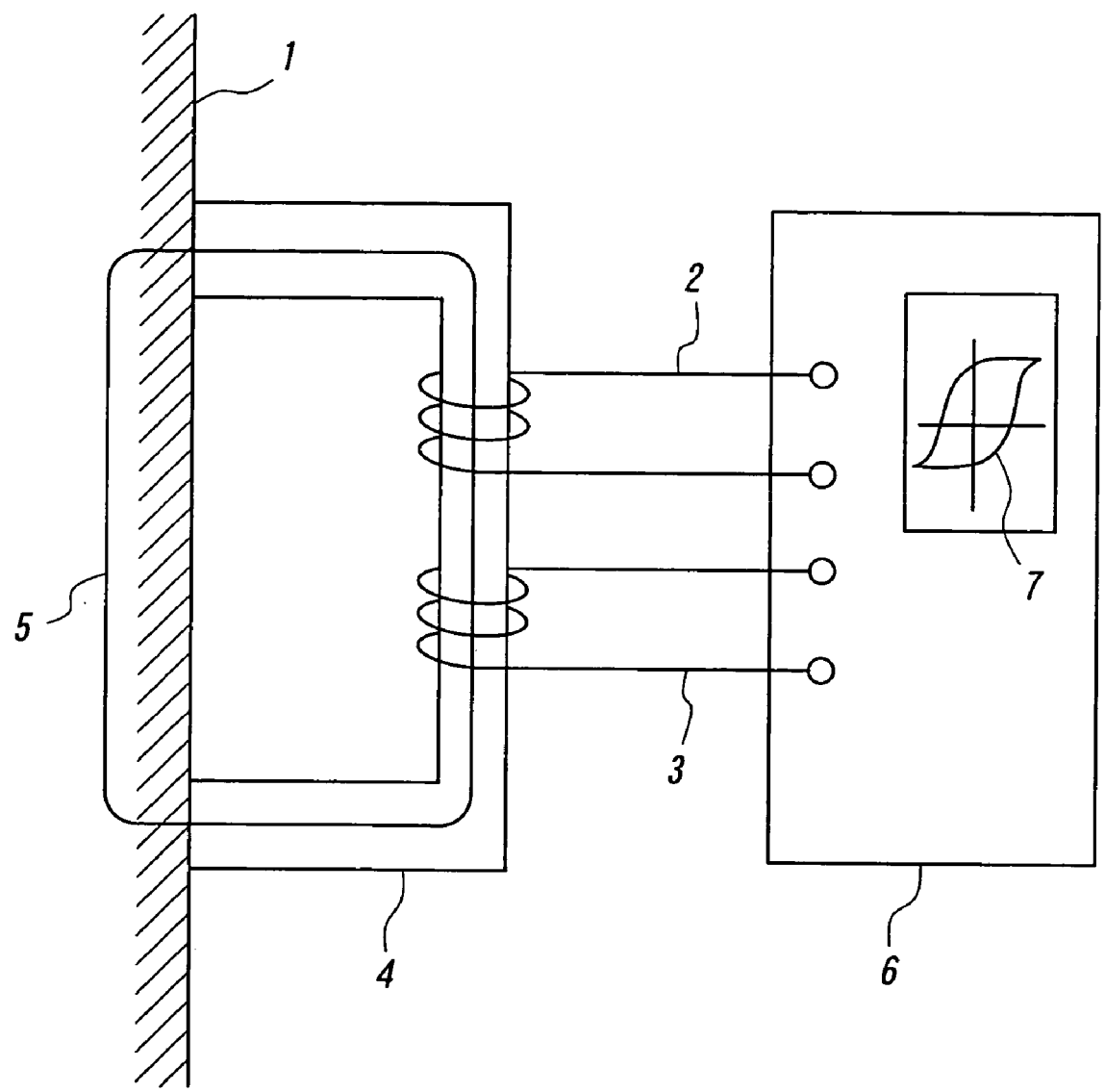
FIG. 33 is an explanatory view showing a nondestructive evaluating method according to a first embodiment of the present invention, for aged deterioration in austenitic stainless steel.

There will be described hereinafter the embodiments according to the present invention in detail, with reference to the accompanying drawings. FIG. 33 is an explanatory view showing a nondestructive evaluating method according to a first embodiment of the present invention, for aged deterioration in austenitic stainless steel.

In this figure, reference numeral 1 designates an evaluation target austenitic stainless steel structure (hereinafter called "evaluation target structure") constituted of an austenitic stainless steel structural material in which some deterioration of material is existent, 2 an exciting coil, 3 a magnetic flux detecting coil, and 4 a magnetic yoke wound with these coils.

Herein, as shown in FIG. 33, the magnetic yoke 4 having the exciting coil 2 and the magnetic flux detecting coil 3 is closely contacted with the evaluation target structure 1 in the shape incapable of being directly wound with the exciting coil 2 and the magnetic flux detecting coil 3, to thereby form the closed magnetic circuit 5.

Reference numeral 6 designates a minor hysteresis loop characteristic measuring apparatus connected with the exciting coil 2 and the magnetic flux detecting coil 3, and it is possible to adopt a general commercial product as the minor hysteresis loop measuring apparatus 6.

Further, reference numeral 7 designates a minor hysteresis loop characteristic of the evaluation target structure 1 which is displayed on the minor hysteresis loop measuring apparatus 6 as a result of carrying out this embodiment.

Note, the evaluation target structure 1 to be evaluated in this embodiment has aged deterioration due to usage under temperatures below 200° C., and the aged deterioration has caused the martensitic transformation so that a part of the austenite phase has transformed into the martensitic phase.

According to the minor hysteresis loop measuring apparatus 6, the exciting coil 2 is supplied with an exciting current upon measuring the evaluation target structure 1 in the measuring step, and the voltage induced in the magnetic flux detecting coil 3 at this time is conducted to the minor hysteresis loop characteristic measuring apparatus 6, thereby resultingly obtain the minor hysteresis loop characteristic 7.

From the minor hysteresis loop characteristic 7 to be used as a subject minor hysteresis loop, there can be obtained the pseudo coercive force Hc*, as well as the pseudo susceptibility $\chi_H^*$ at that point (see FIG. 4).

The minor hysteresis loop characteristic 7 obtained by the above-mentioned measurement includes errors such as due to a 3-dimensional spread of magnetic paths within the evaluation target structure 1 and due to affection of a demagnetizing factor. Although it is thus necessary to obtain a compensation coefficient for obtaining the minor hysteresis loop characteristic excluding such errors, this compensation coefficient can be previously obtained by a computer experiment using a known static magnetic field analyzing method or by a mock-up experiment for simulating an actual measurement system.

In case of evaluating the aged deterioration in the evaluation target structure 1 based on the pseudo coercive force Hc* and the first ratio Ms/$\chi_H^*$ obtained in the measuring step, there shall be previously performed a tensile test at temperatures of 200° C. or lower for a test piece of the same material as the evaluation target structure 1 in the information obtaining step, to thereby obtain a relationship between the stress and strain.

The test piece is applied with a stress σ of a value to be varied correspondingly to the obtained relationship between the stress and strain, and the magnetic field amplitude $H_a$ is stepwise varied in steps of 1 [Oe] between a range of the magnetic field intensity H from 5 [Oe] to 100 [Oe].

Based on the reference minor hysteresis loops obtained at respective measurements, there are obtained the first relationship of the relationship between the pseudo coercive force Hc* and the magnetic field amplitude $H_a$ (see FIG. 6 and FIG. 7) and the second relationship of the relationship between the first ratio Ms/$\chi_H^*$ and the magnetic field amplitude $H_a$ (see FIG. 8 and FIG. 9). Further, by plotting these relationships, there is obtained the third relationship of the relationship between the first ratio Ms/$\chi_H^*$ and the pseudo coercive force Hc* such shown in FIG. 34.

Figure 34:
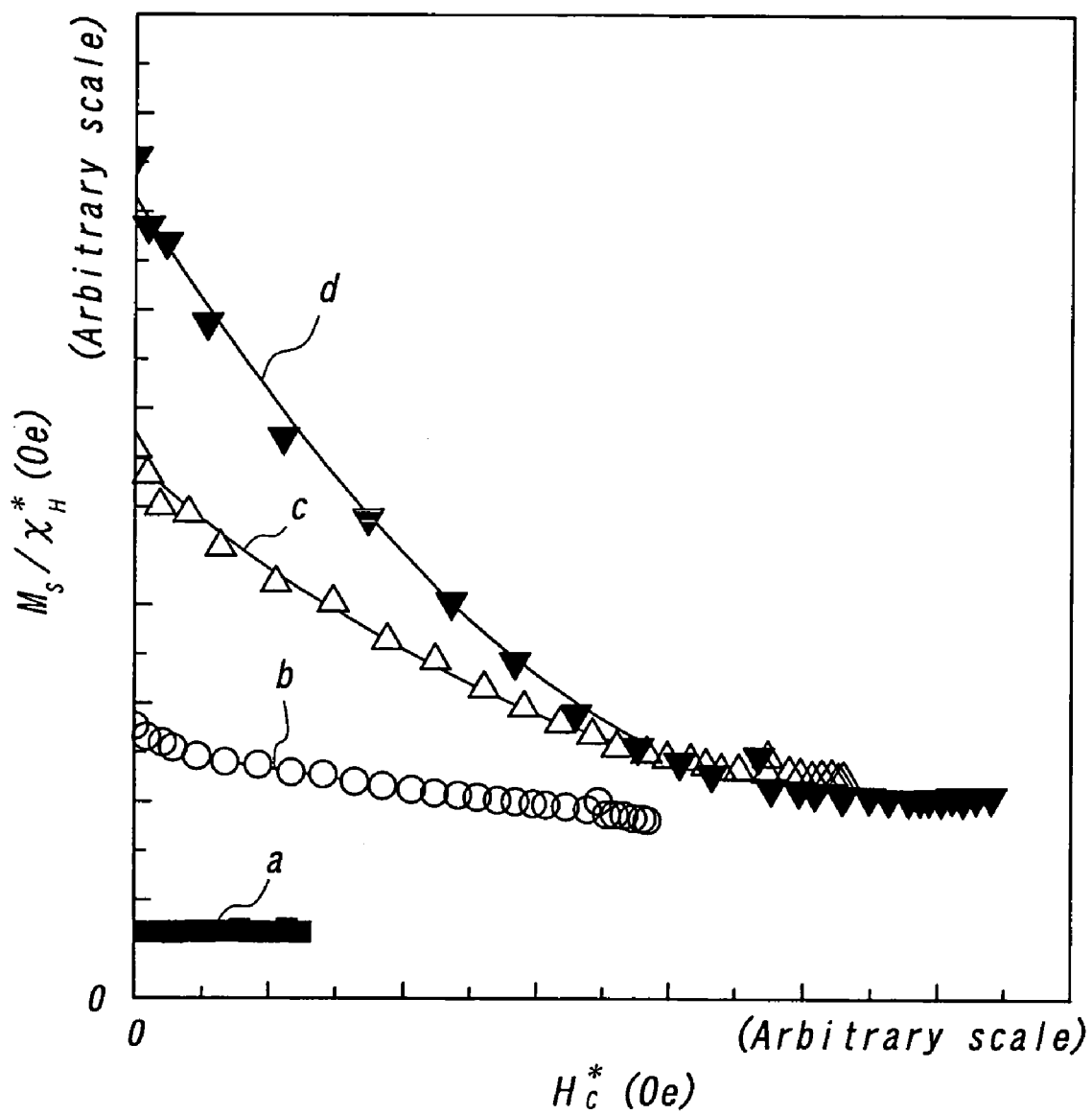
FIG. 34 is an explanatory view exemplifying a relationship between the pseudo coercive force Hc* and the first ratio Ms/$\chi_H^*$, obtained in the first embodiment.

Then, in the evaluating step, the values of the pseudo coercive force Hc* and the first ratio Ms/$\chi_H^*$ of the evaluation target structure 1 are compared with the third relationship shown in FIG. 34, thereby making it possible to quantitatively inspecting the state of aged deterioration in the evaluation target structure 1. Note, the relationships shown in FIG. 34 are changed in the order of the curve a→curve b→curve c→curve d as the applied stress σ is increased, and the breaking is finally caused at the curved.

Figure 35:
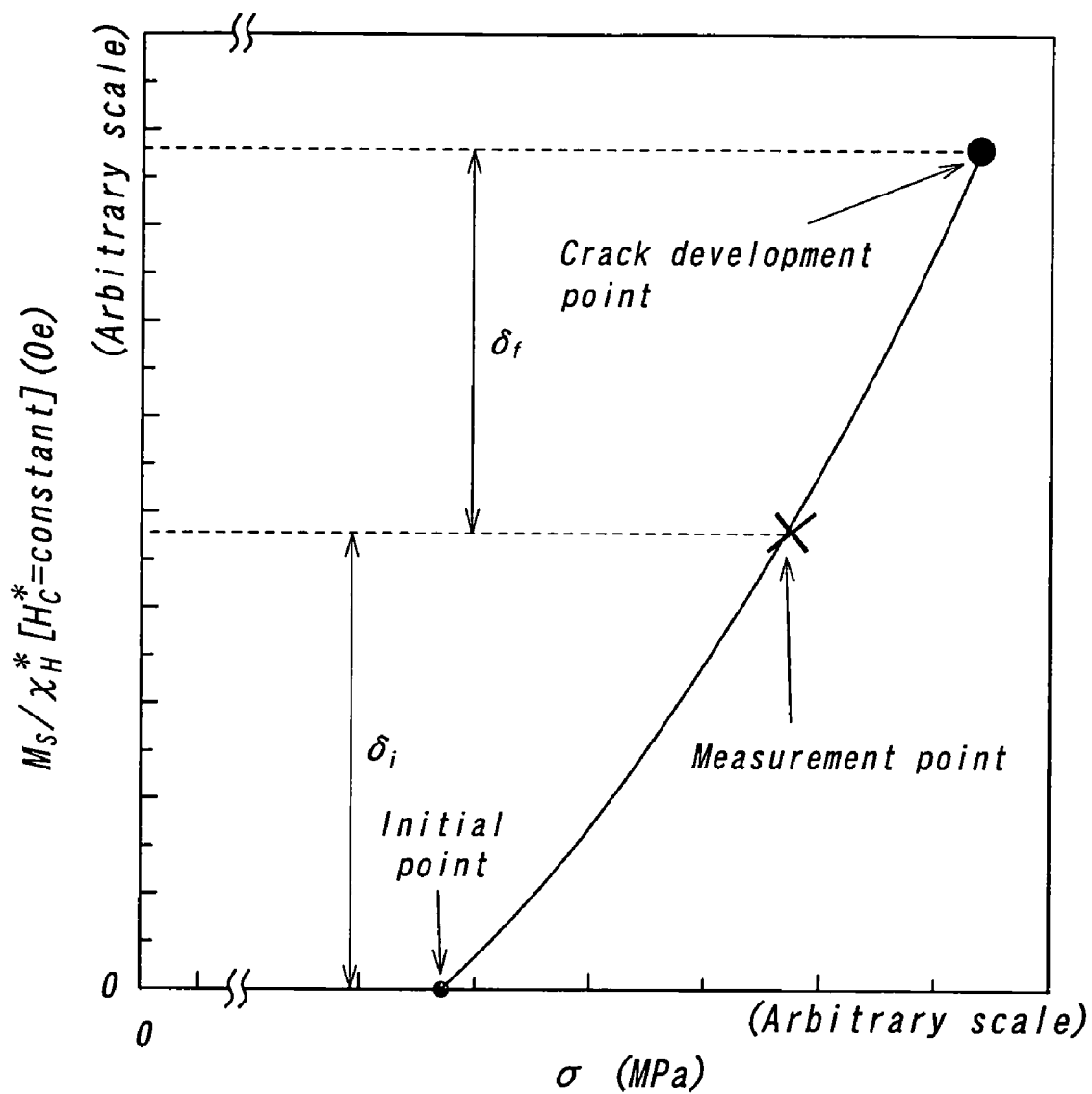
FIG. 35 is an explanatory view exemplifying the fourth relationship of the relationship between the first ratio Ms/$\chi_H^*$ and the applied stress σ where Hc*=constant, obtained in the first embodiment.

Further, to compare the above obtained relationship between the pseudo coercive force Hc* and the first ratio Ms/$\chi_H^*$ of the evaluation target structure 1 with the relationship between the pseudo coercive force Hc* and the first ratio Ms/$\chi_H^*$ in the initial state, upon the crack initiation and upon breaking of the evaluation target structure 1, there is obtained the relationship between the applied stress σ and the first ratio Ms/$\chi_H^*$ at Hc*=constant as shown in FIG. 35 in a manner similar to the obtainment by setting Hc*=4 [Oe] in FIG. 15 and FIG. 16, for example. Then, those values of the first ratio Ms/$\chi_H^*$ at a predetermined pseudo coercive force Hc* which have been obtained by conducting the minor hysteresis loop test for the evaluation target structure 1 are plotted as measured values in FIG. 35, thereby making it possible to obtain the substantial internal stress (applied stress σ) of the evaluation target structure 1 subjected to the aged deterioration.

Namely, plotting the measured values into the relational diagram of FIG. 35 enables to obtain differences $\delta_i$, $\delta_f$ of the first ratio Ms/$\chi_H^*$ between the measurement point and the initial point (initial state) and crack development point, respectively. The $\delta_i$ herein is a changed amount of the first ratio Ms/$\chi_H^*$ from the initial state to the measurement point, and represents an extent of aged deterioration exerted to the material.

Further, the $\delta_f$ herein is a changed amount of the first ratio Ms/$\chi_H^*$ which is estimated for a period of time from the measurement point to the crack development point, and represents an expected life, i.e., a period of time from the present state (measurement point) to the point of crack development in the material. Since the $\delta_i$, $\delta_f$ are parameters representing the extent of aged deterioration in the evaluation target structure 1, the values thereof allow to nondestructively evaluate the extent of aged deterioration in the evaluation target structure 1.

As described above, in the information obtaining step of the nondestructive evaluating method for aged deterioration in austenitic stainless steel in this embodiment, the third relationship of the relationship between the first ratio Ms/$\chi_H^*$ and the pseudo coercive force Hc* shown in FIG. 17 is obtained from the first relationship of the relationship between the pseudo coercive force Hc* and the magnetic field amplitude $H_a$ (for example, the relationships shown in FIG. 6 and FIG. 7) and the second relationship of the relationship between the first ratio Ms/$\chi_H^*$ and the magnetic field amplitude $H_a$ (for example, relationships shown in FIG. 8 and FIG. 9), obtained for the specimen of austenitic stainless steel of the same kind as the evaluation target structure 1.

Then, the fourth relationship of the relationship between the first ratio Ms/$\chi_H^*$ and the applied stress σ shown in FIG. 35 is obtained from the third relationship in the evaluating step, and the state of aged deterioration of the evaluation target structure 1 is evaluated based on the thus obtained fourth relationship.

In this way, by evaluating the relationship between the first ratio Ms/$\chi_H^*$ and pseudo coercive force Hc* and the first relationship and the second relationship of an austenitic stainless steel structural material as an evaluation target which relationships are obtained in the measuring step, it becomes possible to more detailedly measure the kinds and amounts of lattice defects which act as causes of aged deterioration in austenitic stainless steel and which are important in evaluating the state of such aged deterioration.

Thus, according to the nondestructive evaluating method for aged deterioration in austenitic stainless steel of this embodiment, by measuring the minor hysteresis loop characteristics 7 obtained by the minor hysteresis loop test for conducting measurement within a narrow range of the magnetic field intensity H, it becomes possible: to nondestructively and precisely inspect the extent of aged deterioration in all structures constituted of austenitic stainless steel structural material such as in an atomic reactor piping and a chemical plant, based on dislocation densities and a change of distribution thereof at a stage before the initiation of crack; and to evaluate the specimens and the evaluation target structure 1, by constituting a simple apparatus provided with a small-sized magnetic yoke and an exciting power source.

Further, in the evaluating method of this embodiment, the third relationship of the relationship between the first ratio $Ms/\chi_H^*$ and the pseudo coercive force $Hc^*$ shown in FIG. 34 is obtained from the first relationship and the second relationship in the information obtaining step as described above.

In this way, the relational diagram represented by the third relationship shown in FIG. 34 show the form and magnitude of potential energy of domain wall movements, thereby allowing to more precisely and readily evaluate the aged deterioration in the evaluation target, based on this relational diagram.

Note, since both of the first ratio $Ms/\chi_H^*$ and the pseudo coercive force $Hc^*$ are magnetic quantities concerning characteristics of a material, the relationship represented by the first ratio $Ms/\chi_H^*$ and pseudo coercive force $Hc^*$ does not include external variables such as the magnetic field amplitude $H_a$, and includes only internal factors of the material.

Thus, the relationship represented by the first ratio $Ms/\chi_H^*$ and pseudo coercive force $Hc^*$ is to give information of physical properties within the material inclusive of lattice defects, without depending on external variables, the amount of the martensitic phase, and the like.

Further, in the evaluating method of this embodiment, the fourth relationship of the relationship between the first ratio $Ms/\chi_H^*$ and the applied stress σ shown in FIG. 35 is obtained in the information obtaining step as described above from the third relationship shown in FIG. 34, and the state of aged deterioration of the evaluation target structure 1 is evaluated in the evaluating step based on the fourth relationship.

In this way, it becomes possible to quantitatively obtain the values of applied stress σ during a period of time from a state before aged deterioration to a state upon the crack initiation by measuring and obtaining the value of the first ratio $Ms/\chi_H^*$, thereby more precisely predicting an extent of progress of aged deterioration, an expected life and the like of the evaluation target. Further, it is possible to know the dislocation density from the value of applied stress σ, by previously obtaining the correlation between the applied stress σ and the dislocation density.

Figure 36:
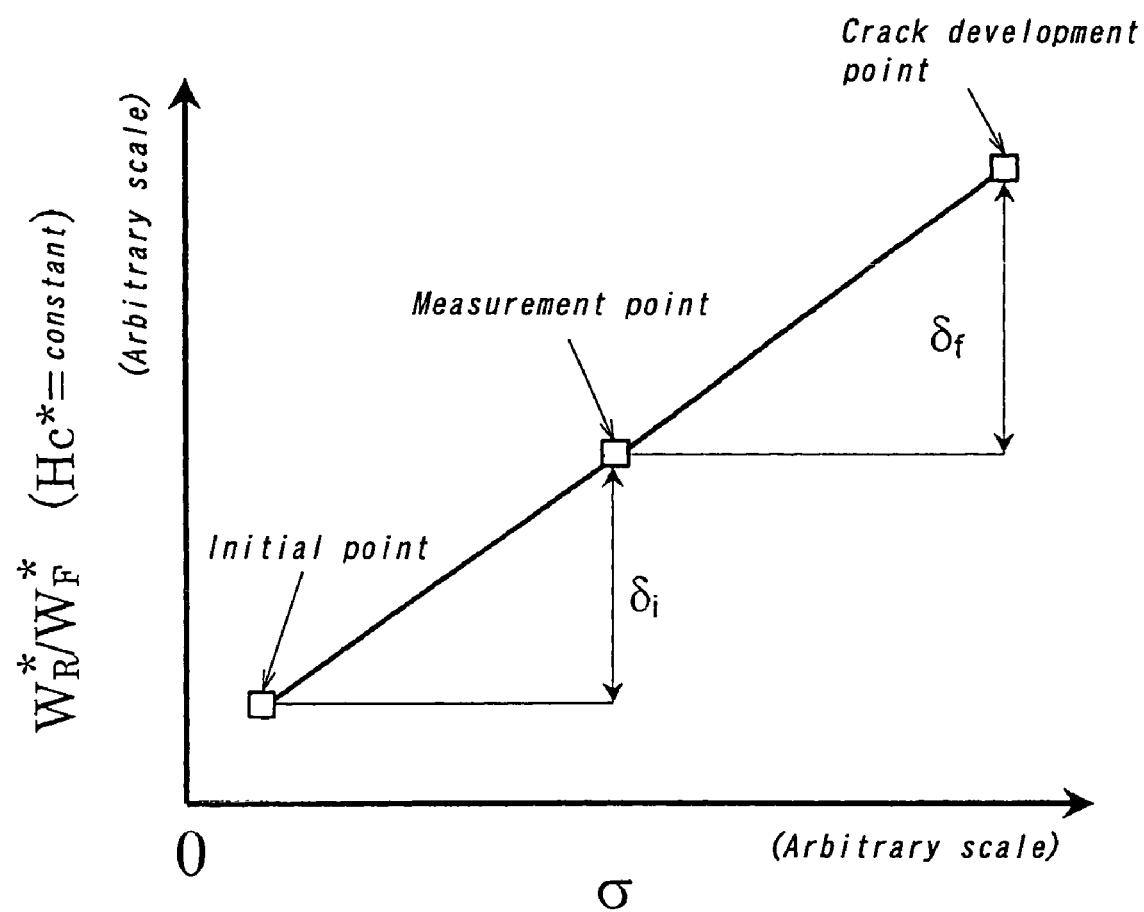
FIG. 36 is an explanatory view exemplifying the ninth relationship of the relationship between the second ratio $W_R^*/W_F^*$ and the applied stress σ where Hc*=constant, obtained in the first modified embodiment.

FIG. 36 is an explanatory view exemplifying the ninth relationship of the relationship between the second ratio $W_R^*/W_F^*$ and the applied stress σ where $Hc^*$=constant, obtained in a first modified embodiment.

In this modified embodiment, instead of the correlations between physical quantities in the first embodiment, there is adopted the fifth relationship of the relationship between: the second ratio $W_R^*/W_F^*$ between, the pseudo hysteresis loss $W_F^*$ which is an area of portion surrounded by the reference minor hysteresis loop, and the pseudo remanence work $W_R^*$ obtained from the area of portion surrounded by the reference minor hysteresis loop; and the pseudo coercive force $Hc^*$ which is a value of a magnetic field intensity H where a value of a magnetic flux density B is zero.

Further, the measured values of physical quantities to be measured in the measuring step are selected to be the values of the pseudo coercive force $Hc^*$ and the second ratio $W_R^*/W_F^*$. Moreover, there is obtained the ninth relationship of the relationship between the second ratio $W_R^*/W_F^*$ and the applied stress σ at a certain constant pseudo coercive force $Hc^*$, such as shown in FIG. 36. Then, based on the relational diagram, it becomes possible to evaluate the information of aged deterioration in the evaluation target structure 1, in the manner similar to the situation adopting the previous diagram shown in FIG. 35.

Figure 37:
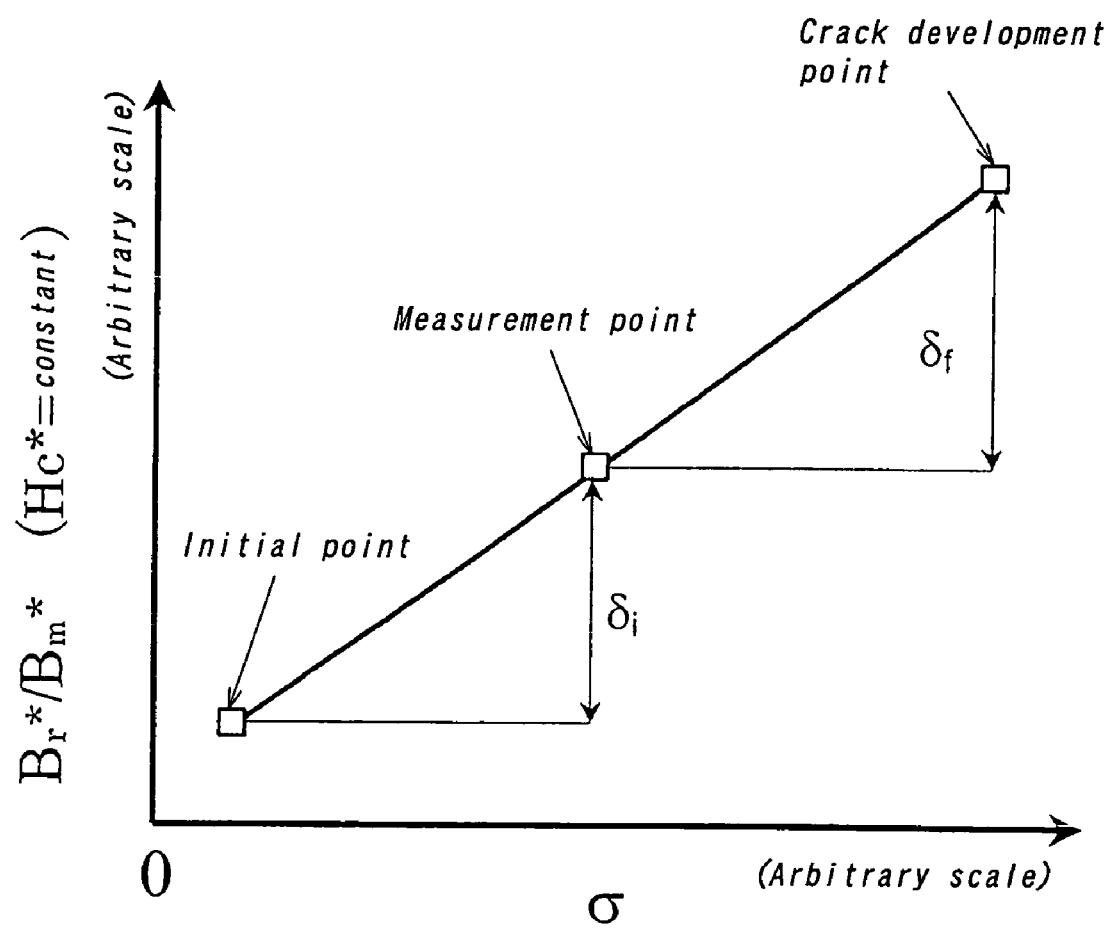
FIG. 37 is an explanatory view exemplifying the tenth relationship of the relationship between the third ratio Br*/Bm* and the applied stress σ where Hc*=constant, obtained in the second modified embodiment.

FIG. 37 is an explanatory view exemplifying the tenth relationship of the relationship between the third ratio $Br^*/Bm^*$ and the applied stress σ where $Hc^*$=constant, obtained in a second modified embodiment.

In this modified embodiment, instead of the correlations between physical quantities in the first embodiment, there is adopted the sixth relationship of the relationship between: the third ratio $Br^*/Bm^*$ between, the pseudo remanence $Br^*$ which is a value of magnetic flux density B where the value of magnetic field intensity H is zero, and the pseudo magnetization $Bm^*$ which is a value of the magnetic flux density B at the magnetic field amplitude $H_a$; and the pseudo coercive force $Hc^*$.

Further, the measured values of physical quantities to be obtained in the measuring step are selected to be the values of the pseudo coercive force $Hc^*$ and the third ratio $Br^*/Bm^*$. Moreover, there is obtained the tenth relationship of the relationship between the third ratio $Br^*/Bm^*$ and the applied stress σ at a certain constant pseudo coercive force $Hc^*$, such as shown in FIG. 37.

Then, based on the relational diagram, it becomes possible to evaluate the information of aged deterioration in the evaluation target structure 1, in the manner similar to the situation adopting the previous diagram shown in FIG. 35.

Figure 38:
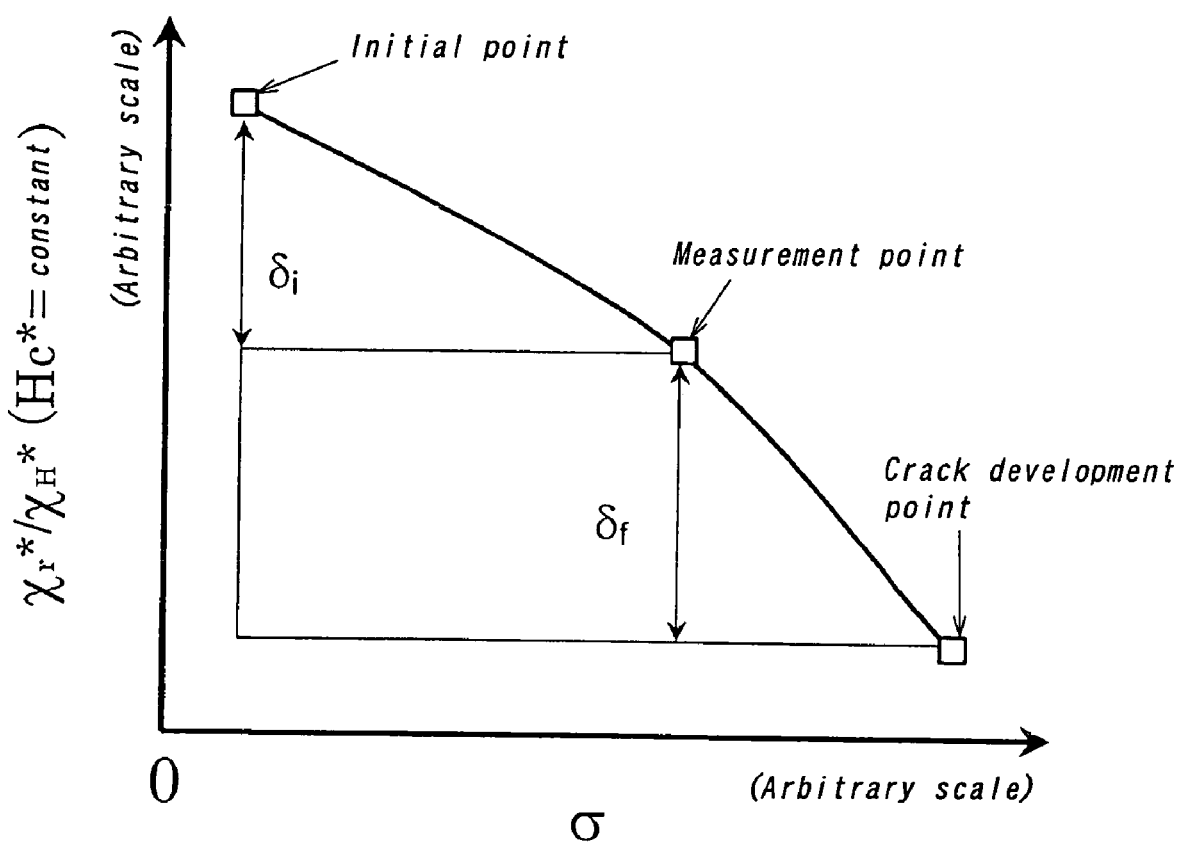
FIG. 38 is an explanatory view exemplifying the eleventh relationship of the relationship between the fourth ratio $\chi_r^*/\chi_H^*$ and the applied stress σ where Hc*=constant, obtained in the third modified embodiment.

FIG. 38 is an explanatory view exemplifying the eleventh relationship of the relationship between the fourth ratio $\chi_r^*/\chi_H^*$ and the applied stress σ where $Hc^*$=constant, obtained in the third modified embodiment.

In this modified embodiment, instead of the correlations between physical quantities in the first embodiment, there is adopted the seventh relationship of the relationship between: the fourth ratio $\chi_r^*/\chi_H^*$ between, the pseudo remanence susceptibility $\chi_r^*$ at the pseudo remanence $Br^*$ which is a value of magnetic flux density B where the value of magnetic field intensity H is zero, and the pseudo susceptibility $\chi_H^*$ at the pseudo coercive force $Hc^*$. Further, the measured values of physical quantities to be obtained in the measuring step are selected to be the values of the pseudo coercive force $Hc^*$ and the fourth ratio $\chi_r^*/\chi_H^*$. Moreover, there is obtained the eleventh relationship of the relationship between the fourth ratio $\chi_r^*/\chi_H^*$ and the applied stress σ at a certain constant value of pseudo coercive force $Hc^*$, such as shown in FIG. 38. Then, based on the relational diagram, it becomes possible to evaluate the information of aged deterioration in the evaluation target structure 1, in the manner similar to the situation adopting the previous diagram shown in FIG. 35.

Figure 39:
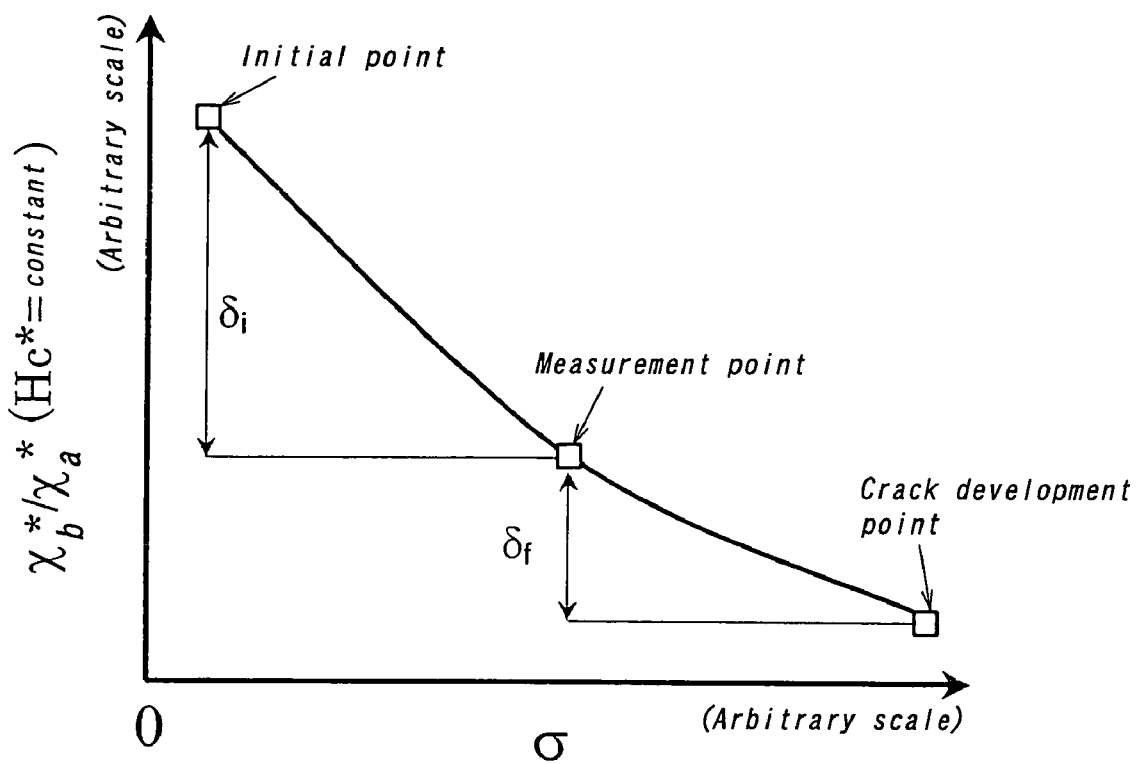
FIG. 39 is an explanatory view exemplifying the twelfth relationship of the relationship between the fifth ratio $\chi_b^*/\chi_a^*$ and the applied stress σ, obtained in the fourth modified embodiment.

FIG. 39 is an explanatory view exemplifying the twelfth relationship of the relationship between the fifth ratio $\chi_b^*/\chi_a^*$ and the applied stress σ, obtained in the fourth modified embodiment. In this modified embodiment, instead of the correlations between physical quantities in the first embodiment, there is adopted the eighth relationship of the relationship between: the fifth ratio $\chi_b^*/\chi_a^*$ between, the smaller pseudo susceptibility $\chi_b^*$ and the larger pseudo susceptibility $\chi_a^*$ at the magnetic field amplitude $H_a$; and the pseudo coercive force $Hc^*$.

Further, the measured values of physical quantities to be obtained in the measuring step are selected to be the values of the pseudo coercive force $Hc^*$ and the fifth ratio $\chi_b^*/\chi_a^*$. Moreover, there is obtained the twelfth relationship of the relationship between the fifth ratio $\chi_b^*/\chi_a^*$ and the applied stress σ at a certain constant value of pseudo coercive force $Hc^*$, such as shown in FIG. 39. Then, based on the relational diagram, it becomes possible to evaluate the information of aged deterioration in the evaluation target structure 1, in the manner similar to the situation adopting the previous diagram shown in FIG. 35.

According to the first modified embodiment, the second modified embodiment, the third modified embodiment and the fourth modified embodiment, the ratios of physical quantities such as the second ratio $W_R*/W_F*$, the third ratio $Br*/Bm*$, the fourth ratio $\chi_r*/\chi_H*$ and the fifth ratio $\chi_b*/\chi_a*$ do not depend on the amount of the martensitic phase. Thus, there are not required magnetic field intensities H of $10^4$ [Oe] or more for directly obtaining the saturation magnetization Ms due to the martensitic phase, so that any difficulty is not caused upon conducting a nondestructive inspection even without relying on the above-mentioned expedient method.

Further, all of the pseudo coercive force Hc*, the pseudo hysteresis loss $W_F*$, the pseudo remanence work $W_R*$, the pseudo susceptibility $\chi_H*$ at the pseudo coercive force Hc*, the pseudo remanence Br*, the pseudo remanence susceptibility $\chi_r*$ at the pseudo remanence Br*, the pseudo susceptibility $\chi_H*$ at the pseudo coercive force Hc*, and the two susceptibilities $\chi_b*$ and $\chi_a*$ at the magnetic field amplitude $H_a$ are magnetic quantities concerning characteristics of a material. Thus, the relationships represented by these physical quantities do not explicitly include external variables such as the magnetic field amplitude $H_a$, and includes only internal factors of the material.

Thus, the relationships represented by the physical quantities are to give information of physical properties within the material inclusive of lattice defects, without depending on external variables. Further, by obtaining ratios among these physical quantities, it becomes possible to exclude the affection of the amount of the martensitic phase on these physical quantities and to obtain the information concerning only the interior of the material.

Moreover, by utilizing the relational diagrams of FIG. 36 through FIG. 39, it becomes possible to quantitatively obtain the values of applied stress σ during a period of time from a state before aged deterioration to a state upon the crack initiation by measuring and obtaining the values of the second ratio $W_R*/W_F*$, the third ratio $Br*/Bm*$, the fourth ratio $\chi_r*/\chi_H*$ and the fifth ratio $\chi_b*/\chi_a*$ of the evaluation target in the measuring step, thereby more precisely predicting an extent of progress of aged deterioration, an expected life and the like of the evaluation target. Further, it is possible to know the change of dislocation density from the value of applied stress σ, by the above-explained information obtaining step.

Additionally, all of the pseudo coercive force Hc*, the pseudo hysteresis loss $W_F*$, the pseudo remanence work $W_R*$, the pseudo susceptibility $\chi_H*$ at the pseudo coercive force Hc*, the pseudo remanence Br*, the pseudo remanence susceptibility $\chi_r*$ at the pseudo remanence Br*, the pseudo susceptibility $\chi_H*$ at the pseudo coercive force Hc*, and the two susceptibilities $\chi_b*$ and $\chi_a*$ at the magnetic field amplitude $H_a$ are physical quantities sensitive to lattice defects such as dislocation, and all of these physical quantities can be obtained from the minor hysteresis loop to be obtained by measurement.

Incidentally, in the conventional method for measuring saturation magnetization based on a change of the amount of the martensitic phase, it has been difficult to evaluate aged deterioration in a material due to lattice defects such as dislocations, because the amount of the martensitic phase caused by transformation is steeply reduced with elevation of temperature even in a temperature range of 200° C. or lower.

Contrary, according to the nondestructive evaluating method for aged deterioration in austenitic stainless steel of this embodiment, it is possible to conduct the evaluation utilizing the first ratio $Ms/\chi_H*$, the second ratio $W_R*/W_F*$, the third ratio $Br*/Bm*$, the fourth ratio $\chi_r*/\chi_H*$ and the fifth ratio $\chi_b*/\chi_a*$, which are not based on the amount of the martensitic phase caused by transformation. Thus, the evaluation of a material based on the evaluating method of this embodiment is indispensable, when the martensitic transformation is affected by temperature.

Figure 40:
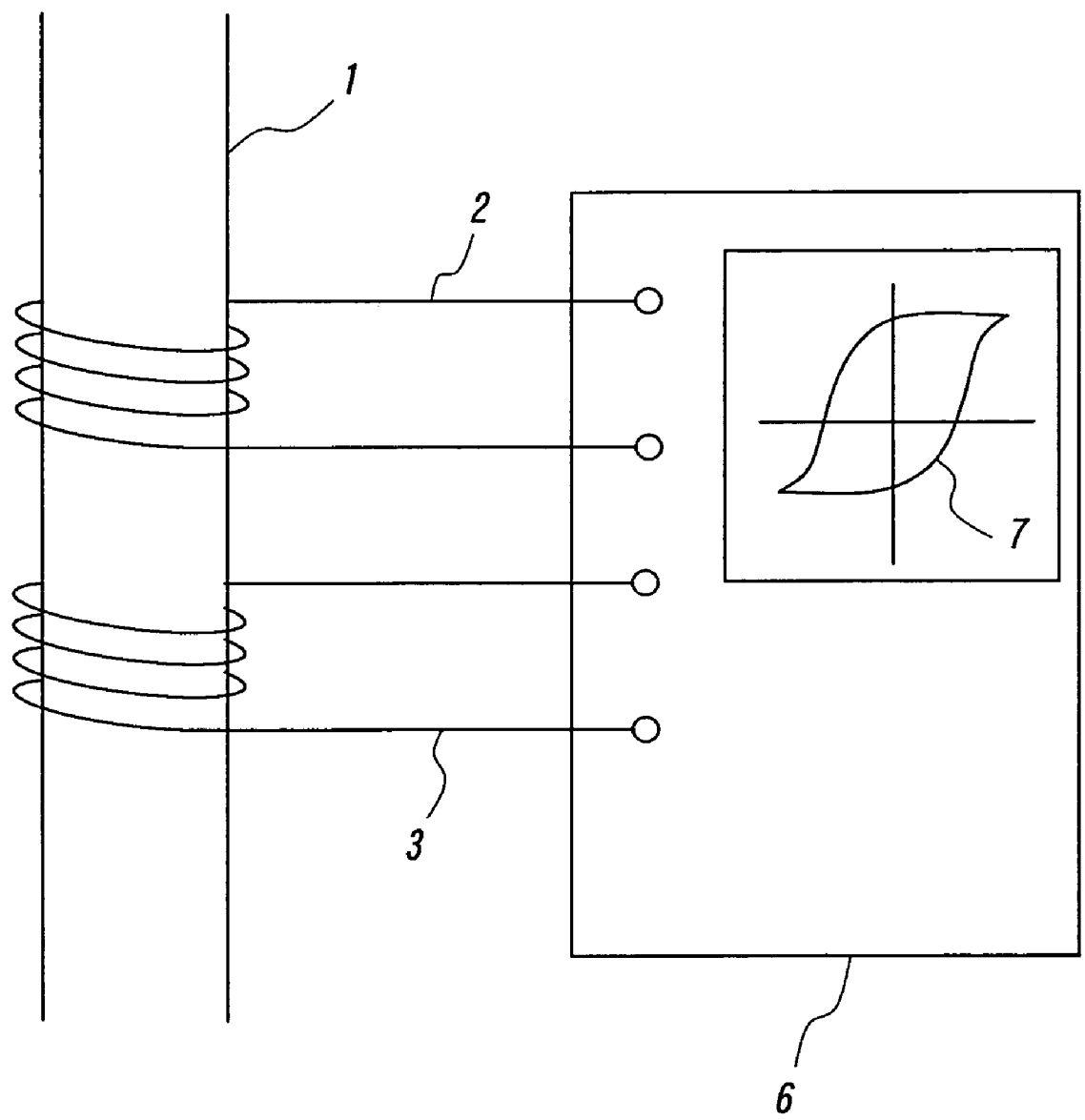
FIG. 40 is an explanatory view showing a nondestructive evaluating method according to a second embodiment of the present invention, for aged deterioration in austenitic stainless steel.

FIG. 40 is an explanatory view showing a nondestructive evaluating method according to the second embodiment of the present invention, for aged deterioration in austenitic stainless steel. Unlike the first embodiment, the evaluation target structure 1 subjected to some aged deterioration has a shape capable of being directly wound with the exciting coil 2 and the magnetic flux detecting coil 3 in this embodiment, so that the exciting coil 2 and the magnetic flux detecting coil 3 are directly wound onto the evaluation target structure 1.

It is possible also here to adopt a general commercial product as the minor hysteresis loop measuring apparatus 6, similarly to the first embodiment. Further, reference numeral 7 designates a minor hysteresis loop characteristic which is displayed on the minor hysteresis loop measuring apparatus 6 as a result of carrying out this embodiment.

In the measuring step of this embodiment, the minor hysteresis loop characteristics 7 obtained by measurement are adopted as subject minor hysteresis loops, and the values of pseudo coercive force Hc* and the first ratio $Ms/\chi_H*$ are obtained therefrom, similarly to the previous first embodiment. In the information obtaining step, there are obtained the first relationship of the relationship between the pseudo coercive force Hc* and the magnetic field amplitude $H_a$ and the second relationship of the relationship between the first ratio $Ms/\chi_H*$ and the magnetic field amplitude $H_a$ from reference minor hysteresis loops previously obtained concerning a test piece of the same material as the evaluation target structure 1 in the manner similar to the first embodiment, and there is further obtained, from the thus obtained relationships, the third relationship of the relationship between the first ratio $Ms/\chi_H*$ and the pseudo coercive force Hc* (see FIG. 34 concerning the previous first embodiment).

In the evaluating step, the values of pseudo coercive force Hc* and the first ratio $Ms/\chi_H*$ having been obtained in the information obtaining step are compared with the values of pseudo coercive force Hc* and the first ratio $Ms/\chi_H*$ of the evaluation target structure 1, thereby making it possible to evaluate the substantial extent of aged deterioration of the evaluation target structure 1.

Further, similarly to what is shown in FIG. 35 concerning the previous first embodiment, there is obtained a relationship between the first ratio $Ms/\chi_H*$ and the applied stress σ where Hc*=constant, so as to obtain the aged deterioration level $\delta_i$ and the expected life $\delta_f$, thereby making it possible to nondestructively evaluate the extent of aged deterioration in the evaluation target structure 1.

Thus, according to the nondestructive evaluating method for aged deterioration in austenitic stainless steel of the second embodiment, it becomes possible to exclude the usage of magnetic yoke thereby making it possible to attain the simplified and light-weighted measuring apparatus, in addition to the same effect as the previous first embodiment.

Incidentally, the present inventor has found out, in the study process, that dislocations, grain boundaries and the like obstruct the martensitic transformation. This means that, the martensitic transformation is hardly caused where the dislocation density is high unless a larger stress is applied from the exterior, while the martensitic transformation is likely to be caused where the dislocation density is relatively low even without applying a larger stress from the exterior.

Further, it has been found that the dislocation density is increased also within the martensitic phase as the plastic deformation progresses. As such, it has been impossible to precisely evaluate aged deterioration in the conventional method for evaluating aged deterioration based on the amount of the martensitic phase such as by measuring saturation magnetization, because the internal factor of aged deterioration such as the dislocation density does not correspond to the amount of the martensitic phase so that it is difficult to measure the dislocation density and the like within the martensitic phase.

Contrary, according to the nondestructive evaluating method for aged deterioration in austenitic stainless steel of the above embodiments of the present invention, the obtained information does not depend on the amount of the martensitic phase and enables to measure the internal factor such as the dislocation density at portions other than martensitic phase while measuring lattice defects such as dislocation density within the martensitic phase, thereby allowing to more precisely evaluate the aged deterioration in austenitic stainless steel.

Further, as described above, it is known that austenitic stainless steel transforms into martensite due to plastic deformation, and transits from paramagnetic to ferromagnetic. However, it has been found in the study process by the present inventor that the martensitic transformation is not caused even by applying plastic deformation to a material at 200° C. or higher. For example, in case that an austenitic stainless steel has been hot rolled at 200° C. or higher, the martensitic transformation is not caused even if a state of higher dislocation density is existent within the material, thereby failing to distinguish the resultant state of the material from the state before application of the plastic deformation.

Therefore, by the conventional evaluating method such as based on saturation magnetization, it is impossible to evaluate the deterioration in a material having been used at 200° C. or higher. Also, it is conceivable that the evaluation is impossible even by the methods according to the above embodiments of the present invention, if the martensitic phase is fully absent.

There will be thus explained hereinafter a method for allowing to apply the evaluating methods of the above embodiments to the evaluation of aged deterioration in an austenitic stainless steel having been used at temperatures of 200° C. or higher.

The martensitic transformation of austenitic stainless steel is also caused, such as by quenching it from a room temperature down to a liquid nitrogen temperature (77K). At that time, there is hardly found an increase of dislocation density both in the austenite phase and in the martensitic phase caused by martensitic transformation.

Thus, although the saturation magnetization is increased with the amount of the martensitic phase caused by the transformation, the relationship of the first ratio $Ms/\chi_H^*$ in the above embodiment is unchanged. On the other hand, the amount of the martensitic phase caused by the transformation due to quenching from the room temperature down to the liquid nitrogen temperature (77K) is largely related to the dislocation density within the austenite phase before the occurrence of the martensitic transformation.

Figure 41:
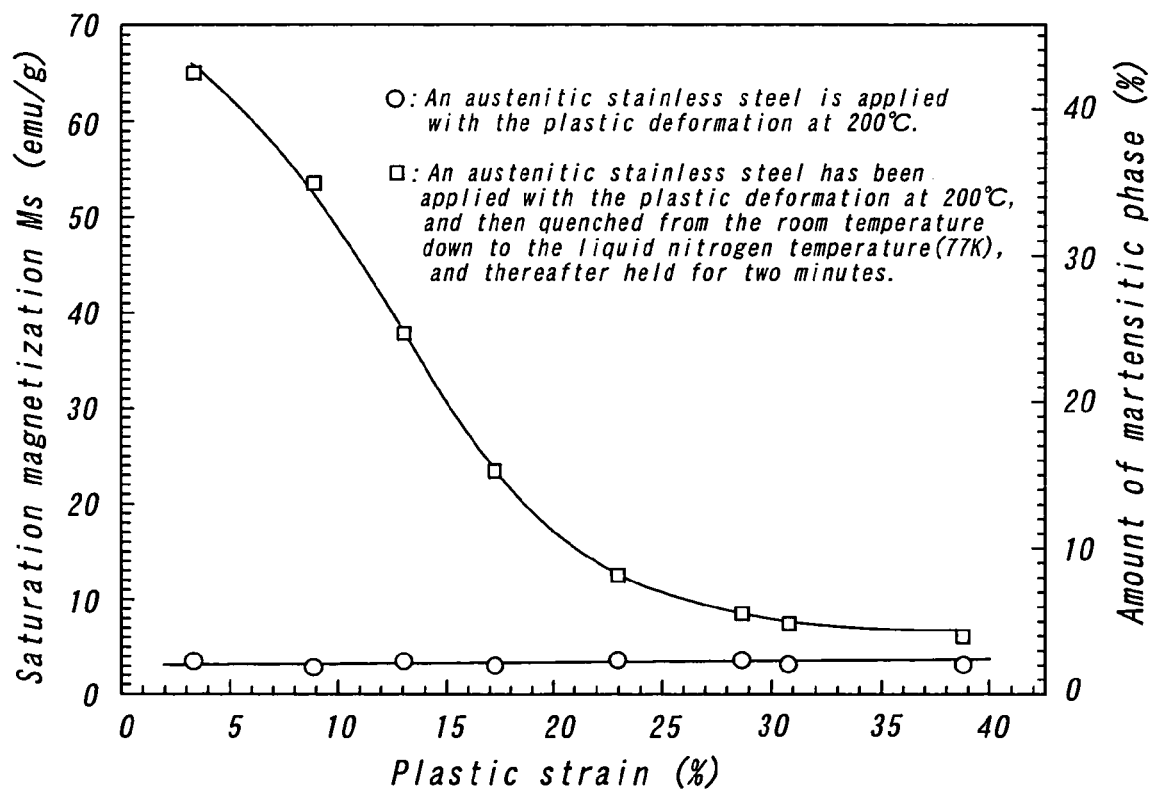
FIG. 41 is an explanatory view showing a relationship among plastic strain [%], saturation magnetization Ms [emu/g], and amount of martensitic phase [%], concerning an austenitic stainless steel applied with the plastic deformation at 200° C., and an austenitic stainless steel which has been applied with plastic deformation at 200° C. and then quenched from the room temperature down to a liquid nitrogen temperature (77K) and thereafter held for two minutes.

Then, FIG. 41 shows values of the amount of the martensitic phase of an austenitic stainless steel which has been applied with plastic deformation at 200° C., then quenched from room temperature down to a liquid nitrogen temperature (77K), and thereafter held for two minutes. The abscissa represents a deformed amount (strain) at 200° C. In FIG. 41, white circle plots represent the austenitic stainless steel applied with the plastic deformation at 200° C., and white square plots represent the austenitic stainless steel which has been applied with plastic deformation at 200° C., then quenched from room temperature down to a liquid nitrogen temperature (77K), and thereafter held for two minutes. Further, in FIG. 41, the saturation magnetization Ms is shown in a unit of [emu/g], and the plastic strain and the amount of the martensitic phase are shown in a unit of [%].

As shown in FIG. 41, the austenitic stainless steel, which is applied with plastic deformation at 200° C. or higher and is not quenched, rarely causes martensitic transformation (see white circles in FIG. 41). Contrary, concerning the austenitic stainless steel which has been applied with plastic deformation at 200° C. or higher, then quenched from room temperature down to a liquid nitrogen temperature (77K), and thereafter held for two minutes, this austenitic stainless steel causes the martensitic transformation in a manner that the amount of the martensitic phase to be caused by transformation is steeply reduced as the plastic deformation is progressed and the dislocation density is increased (see white squares in FIG. 41). This is because, the dislocation acts to obstruct the martensitic transformation.

As such, it is possible to conduct a nondestructive inspection for aged deterioration of an austenitic stainless steel structural material used at 200° C. or higher as well as a structure adopting it, by utilizing the relationship shown in FIG. 41. Concretely, there is conducted such a quenching step that the evaluating portion of the evaluation target structure 1 used at 200° C. or higher is quenched down to a liquid nitrogen temperature (77K), before conducting the measuring step.

Similarly to the previous first and second embodiments, there is conducted a minor hysteresis loop test for the evaluation target structure 1 in the measuring step so as to appropriately obtain the first through the fourth relationship from the obtained subject minor hysteresis loops and so as to measure the amount of the martensitic phase caused by the transformation due to quenching in the quenching step, to thereby calculate the dislocation density within the austenite phase based on the amount of the martensitic phase.

Note, although the amount of the martensitic phase caused by the transformation due to quenching is relatively large when the dislocation density is relatively small, the amount of the martensitic phase caused by the transformation due to quenching is reduced when the plastic deformation is progressed and thus the dislocation density is increased.

Note, it is also possible to obtain an internal stress (dislocation density), by conducting the quenching step to quench the evaluating portion of the evaluation target structure 1 down to the liquid nitrogen temperature, and by measuring the saturation magnetization Ms from the relationship of FIG. 41. In that case, the saturation magnetization Ms can be simply obtained from the relationship of FIG. 14, even without applying the magnetic field of $10^4$ [Oe].

Based on the above, in case of measuring aged deterioration of the evaluation target structure 1 having been used at 200° C. or higher in the evaluating methods of the above embodiments, the evaluating portion of the evaluation target structure 1 is quenched from a room temperature down to a liquid nitrogen temperature (77K) to thereby cause the martensitic phase by martensitic transformation, and the minor hysteresis loop measuring test is then conducted for the martensitic phase. This enables to obtain the relationships between the applied stress σ and the first ratio Ms/$\chi_H$* and the like based on the thus obtained subject minor hysteresis loops, and to evaluate the aged deterioration of the material based on the obtained relationships, similarly to the previous first and second embodiments.

Note, the amount of the martensitic phase caused by transformation due to quenching depends on lattice defects such as the dislocation density, grain boundaries, as well as on chemical components such as nickel and chromium. Thus, in conducting this method, it is necessary to previously obtain a database of the relationship between the amount of martensitic phase caused by the transformation due to quenching and the strain (or stress), by using the same kind of test piece as the evaluation target structure 1.

Meanwhile, it might be outside the concept of nondestructive inspecting method in a strict sense, to quench an austenitic stainless steel so as to cause a martensitic phase by martensitic transformation. Nonetheless, it is possible to restore the martensitic phase to the austenite phase, by conducting a heat treatment for the martensitic phase at a temperature on the order of 600° C. to 700° C. for a short time (several minutes) after evaluation of aged deterioration. Thus, the evaluating methods of the previous first and second embodiments are applicable and extremely effective even in evaluating aged deterioration of an austenitic stainless steel used at 200° C. or higher, if the affection due to the heat treatment of the material is negligible.

Note, aged deterioration of a structural material is generally considered to uniformly progress as a whole of the material in a macroscopic sense. As such, it is generally unnecessary to evaluate the aged deterioration of the whole of the evaluation target structure 1, and it is enough to partially or locally evaluate the aged deterioration. Thus, it is sufficient to partially conduct the quench, evaluation and restoration, in the evaluation of aged deterioration in the evaluation target structure 1 used at 200° C. or higher.

However, applied stresses may be locally increased. In order to be applicable even to such a situation, several observing points are to be determined and locally quenched to conduct the evaluation to thereby allow obtaining the information of aged deterioration of the whole of the structural material such that those quenched portions are restored after evaluation.

Thus, according to the constitutions of the first and the second embodiments in the nondestructive evaluating method for aged deterioration in austenitic stainless steel of the present invention, it is possible to conduct the nondestructive evaluation by the magnetic yoke and exciting current, and to conduct a nondestructive evaluation of high sensitivity for aged deterioration in an austenitic stainless steel structural material.

Also in this embodiment, it is possible to apply the relational diagrams in the first modified embodiment, the second modified embodiment, the third modified embodiment and the fourth modified embodiment as explained in the first embodiment.

Although the present invention has been explained based on those embodiments shown in the drawings, the present invention is not limited to such embodiments. For example, although the SUS304 has been used as the austenitic stainless steels in the above embodiments, the austenitic stainless steel the aged deterioration of which can be evaluated by the evaluating method of the present invention is not limited to the SUS304. For example, it has been confirmed that aged deterioration of SUS316 can be evaluated by the evaluating method of the present invention as a result of experiment for the SUS316 conducted in the same manner as the SUS304.

Further, although the embodiments have conducted the evaluation of the structure, it is of course possible to evaluate a structural material for the structure. Moreover, it is of course possible to constitute an aged deterioration evaluating apparatus, by mutually combining those means for performing the respective steps of the methods of the present invention.

What is claimed is:

1. A nondestructive evaluating method for quantitatively and nondestructively evaluating aged deterioration in austenitic stainless steel, comprising:
an information obtaining step for previously conducting a tensile test for the same kind of austenitic stainless steel as an evaluation target austenitic stainless steel, so as to obtain a relationship between stress and strain, and to apply a stress (σ) having a value changed correspondingly to the relationship between stress and strain to the same kind of austenitic stainless steel to thereby obtain reference minor hysteresis loops, thereby obtaining the correlations between physical quantities as evaluating information for aged deterioration of the evaluation target austenitic stainless steel;
a measuring step for measuring the evaluation target austenitic stainless steel to obtain subject minor hysteresis loops, thereby obtaining measured values of the physical quantities from the subject minor hysteresis loops; and
an evaluating step for evaluating the aged deterioration in the evaluation target austenitic stainless steel from the measured values obtained in the measuring step and based on the correlations between physical quantities obtained in the information obtaining step;
wherein each of the minor hysteresis loops is obtained for each magnetic field amplitude ($H_a$) to be applied to the material, based on a relationship between the magnetic field intensity (H) and a magnetic flux density (B) of the austenitic stainless steel obtained by measuring the magnetic flux density (B) while stepwise changing the magnetic field amplitude ($H_a$) within a range of the magnetic field intensity (H) lower than a saturation magnetic field intensity.

2. The nondestructive evaluating method for evaluating aged deterioration in austenitic stainless steel of claim 1,
wherein the correlations between physical quantities comprise: a first relationship of the relationship between a pseudo coercive force (Hc*) which is a value of the magnetic field intensity (H) where the value of magnetic flux density (B) is zero and the magnetic field amplitude ($H_a$) to be applied to the material; and a second relationship of the relationship between, a first ratio (Ms/$\chi_H$*) between a saturation magnetization (Ms) and a pseudo susceptibility ($\chi_H$*) which is a gradient of the reference minor hysteresis loop at the pseudo coercive force (Hc*), and the magnetic field amplitude ($H_a$); and
wherein the measured values of physical quantities to be measured in the measuring step are the pseudo coercive force (Hc*) which is a value of the magnetic field intensity (H) where the value of the magnetic flux density (B) is zero, and the values of the first ratio (Ms/$\chi_H$*).

3. The nondestructive evaluating method for evaluating aged deterioration in austenitic stainless steel of claim 2,
wherein the information obtaining step obtains a third relationship of the relationship between the first ratio ($Ms/\chi_H^*$) and the pseudo coercive force ($Hc^*$), from the first relationship and the second relationship, and wherein the evaluating step evaluates a state of aged deterioration in the evaluation target austenitic stainless steel, based on the third relationship.

4. The nondestructive evaluating method for evaluating aged deterioration in austenitic stainless steel of claim 2 or 3, wherein the information obtaining step obtains a fourth relationship of the relationship between the first ratio ($Ms/\chi_H^*$) and the applied stress ($\sigma$) at a certain constant value of pseudo coercive force ($Hc^*$), from the first relationship and second relationship, or from the third relationship; and wherein the evaluating step evaluates a state of aged deterioration in the evaluation target austenitic stainless steel, based on the third relationship.

5. The nondestructive evaluating method for evaluating aged deterioration in austenitic stainless steel of claim 1, wherein the correlations between physical quantities comprise at least one of:

a fifth relationship of the relationship between: a second ratio ($W_R^*/W_F^*$) between, a pseudo hysteresis loss ($W_F^*$) which is an area of portion surrounded by the reference minor hysteresis loop, and a pseudo remanence work ($W_R^*$) obtained from the area of portion surrounded by the reference minor hysteresis loop; and a pseudo coercive force ($Hc^*$) which is a value of the magnetic field intensity ($H$) where a value of the magnetic flux density ($B$) is zero, a sixth relationship of the relationship between: a third ratio ($Br^*/Bm^*$) between, a pseudo remanence ($Br^*$) which is a value of the magnetic flux density ($B$) where the value of the magnetic field intensity ($H$) is zero, and a pseudo magnetization ($Bm^*$) which is a value of the magnetic flux density ($B$) at the magnetic field amplitude ($H_a$); and the pseudo coercive force ($Hc^*$), a seventh relationship of the relationship between: a fourth ratio ($\chi_r^*/\chi_H^*$) between, a pseudo remanence susceptibility ($\chi_r^*$) at the pseudo remanence ($Br^*$) which is a value of the magnetic flux density ($B$) where the value of the magnetic field intensity ($H$) is zero, and a pseudo susceptibility ($\chi_H^*$) at the pseudo coercive force ($Hc^*$); and the pseudo coercive force ($Hc^*$), and an eighth relationship of the relationship between: a fifth ratio ($\chi_b^*/\chi_a^*$) between, a smaller pseudo susceptibility ($\chi_b^*$), and a larger pseudo susceptibility ($\chi_a^*$) at the magnetic field amplitude ($H_a$); and the pseudo coercive force ($Hc^*$); and wherein the measured values of physical quantities to be measured in the measuring step are the values of the pseudo coercive force ($Hc^*$), and at least one of the following ratios: the second ratio ($W_R^*/W_F^*$), the third ratio ($Br^*/Bm^*$), the fourth ratio ($\chi_r^*/\chi_H^*$) and the fifth ratio ($\chi_b^*/\chi_a^*$), which corresponds to the correlation between the physical quantities.

6. The nondestructive evaluating method for evaluating aged deterioration in austenitic stainless steel of claim 5, wherein the information obtaining step obtains, based on the correlation between physical quantities, at least one of: a ninth relationship of the relationship between the second ratio ($W_R^*/W_F^*$) and the applied stress ($\sigma$) at a certain constant value of pseudo coercive force ($Hc^*$), a tenth relationship of the relationship between the third ratio ($Br^*/Bm^*$) and the applied stress ($\sigma$) at a certain constant value of pseudo coercive force ($Hc^*$), an eleventh relationship of the relationship between the fourth ratio ($\chi_r^*/\chi_H^*$) and the applied stress ($\sigma$) at a certain constant value of pseudo coercive force ($Hc^*$), and a twelfth relationship of the relationship between the fifth ratio ($\chi_b^*/\chi_a^*$) and the applied stress ($\sigma$) at a certain constant value of pseudo coercive force ($Hc^*$); and wherein the evaluating step evaluates a state of aged deterioration in the evaluation target austenitic stainless steel, based on the relationship obtained in the information obtaining step.

* * * * *